(12) United States Patent
Vieira et al.

(10) Patent No.: US 9,725,416 B2
(45) Date of Patent: Aug. 8, 2017

(54) ETHYNYL DERIVATIVES

(71) Applicant: Hoffmann-La Roche Inc., Little Falls, NJ (US)

(72) Inventors: Eric Vieira, Frenkendorf (CH); Georg Jaeschke, Basel (CH); Wolfgang Guba, Mueliheim (DE); Antonio Ricci, Birsfelden (CH); Daniel Rueher, Raedersdorf (FR); Barbara Biemans, Basel (CH); Jean-Marc Plancher, Hagenthal-le-Bas (FR); Fionn O'Hara, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/245,955

(22) Filed: Aug. 24, 2016

(65) Prior Publication Data
US 2016/0362383 A1   Dec. 15, 2016

Related U.S. Application Data

(63) Continuation of application No. PCT/EP2015/053785, filed on Feb. 24, 2015.

(30) Foreign Application Priority Data

Feb. 25, 2014  (EP) ..................... 14156461

(51) Int. Cl.
*C07D 239/22* (2006.01)
*C07D 239/70* (2006.01)
*C07D 491/107* (2006.01)
*C07D 401/04* (2006.01)
*C07D 487/04* (2006.01)
*C07D 401/14* (2006.01)
*C07D 403/04* (2006.01)
*C07D 471/04* (2006.01)
*C07D 401/10* (2006.01)
*C07D 498/04* (2006.01)

(52) U.S. Cl.
CPC ......... *C07D 239/22* (2013.01); *C07D 239/70* (2013.01); *C07D 401/04* (2013.01); *C07D 401/10* (2013.01); *C07D 401/14* (2013.01); *C07D 403/04* (2013.01); *C07D 471/04* (2013.01); *C07D 487/04* (2013.01); *C07D 491/107* (2013.01); *C07D 498/04* (2013.01)

(58) Field of Classification Search
CPC  C07D 239/22; C07D 239/70; C07D 491/107; C07D 401/04; C07D 487/04; C07D 401/14; C07D 403/04; C07D 471/04
See application file for complete search history.

(56) References Cited

U.S. PATENT DOCUMENTS

2011/0124663 A1   5/2011   Conn

FOREIGN PATENT DOCUMENTS

WO   2011/029104 A1   3/2011
WO   2011/128279 A1   10/2011

OTHER PUBLICATIONS

IPER on PCT/EP2015/053785.

*Primary Examiner* — Kahsay Habte
(74) *Attorney, Agent, or Firm* — Tamara A. Kale

(57) ABSTRACT

The present invention relates to compounds that may be used in the treatment or prevention of disorders relating to allosteric modulation of the mGluR4 receptor. Such compounds may be used for the treatment of Parkinson's disease, anxiety, emesis, obsessive compulsive disorder, autism, neuroprotection, cancer, depression and diabetes type 2.

12 Claims, 1 Drawing Sheet

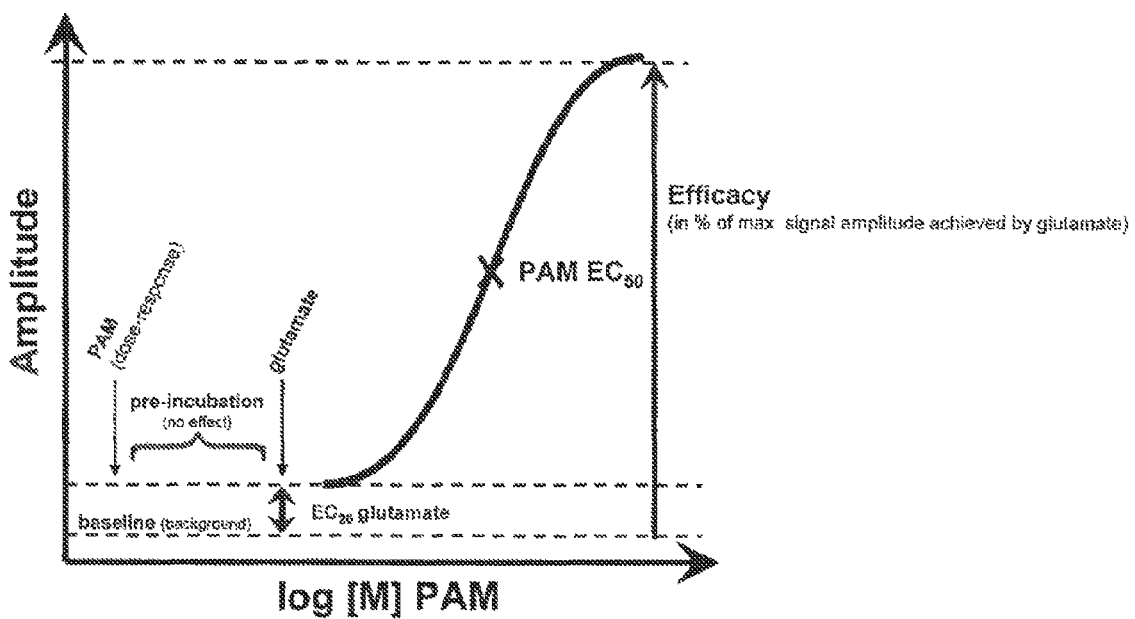

ETHYNYL DERIVATIVES

This application is a continuation of International Application PCT/EP2015/053785, filed Feb. 24, 2015, which claims benefit of priority to European Application 14156461.7, filed Feb. 25, 2014, each of which is incorporated herein by reference in its entirety.

The present invention relates to compounds of formula I

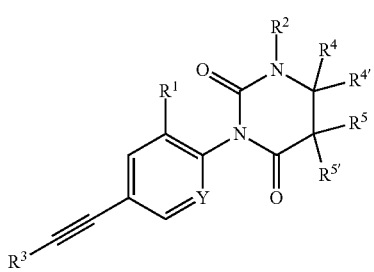

wherein
Y is N or C—$R^{1'}$;
$R^{1'}$ is hydrogen or F;
$R^1$ is hydrogen, halogen or lower alkyl substituted by halogen;
$R^2$ is hydrogen or lower alkyl;
or $R^2$ forms together with $R^4$ a 6 membered heterocyclic ring containing —$CH_2$—$CH_2$—O—$CH_2$— or —$CH_2$—$CH_2$—NR—C(O)—;
R is hydrogen, lower alkyl, phenyl or benzyl;
$R^3$ is phenyl or pyridinyl, wherein the N atom in the pyridinyl group may be in different positions;
$R^{4'}$ is hydrogen, lower alkyl or lower alkoxyalkyl;
$R^4$ is hydrogen, lower alkyl, phenyl optionally substituted by halogen or lower alkoxy, or is cycloalkyl, or is pyridinyl optionally substituted by halogen, lower alkyl, lower alkoxy or =O, or is pyrimidinyl optionally substituted by lower alkyl, lower alkoxy or =O, or is 1-lower alkyl-pyridinyl, or is pyrazinyl, or is pyridazinyl optionally substituted by lower alkyl, lower alkoxy or =O, or is 1-methylpyrrolo[2,3-b]pyridine-5-yl, or is 6-imidazo[1,2-b]pyridazin-6-yl;
or $R^4$ forms together with $R^{4'}$ a 4, 5 or 6 membered heterocyclic ring containing —$(CH_2)_5$—, —$CH_2$—$CH_2$—O—$CH_2$—$CH_2$—, —$CH_2$—$CH_2$—$CH_2$—, —$CH_2$—$CH_2$—$CH_2$—$CH_2$—, —$CH_2$—O—$CH_2$—$CH_2$— or $CH_2$—$CH_2$—$CH_2$—O—$CH_2$;
$R^5$ and $R^{5'}$ are hydrogen or lower alkyl;
or $R^4$ forms together with $R^5$ a saturated 5-membered ring containing —$CH_2$—$CH_2$—$CH_2$—;
or to a pharmaceutically acceptable salt or acid addition salt, to a racemic mixture, or to its corresponding enantiomer and/or optical isomer and/or stereoisomer thereof.

BACKGROUND

It has been surprisingly been found that the compounds of general formula I are positive allosteric modulators (PAMs) of metabotropic glutamate receptor 4 (mGluR4).

Metabotropic glutamate receptor 4 is a protein that in humans is encoded by the GRM4 gene. Together with GRM6, GRM7 and GRM8 it belongs to group III of the Metabotropic glutamate receptor family, and is negatively coupled to adenylate cyclase via activation of the Gαi/o protein. It is expressed primarily on presynaptic terminals, functioning as an autoreceptor or heteroreceptor and its activation leads to decreases in transmitter release from presynaptic terminals. mGluR4 is currently receiving much attention based primarily upon its unique distribution and the recent evidence that activation of this receptor plays key modulatory role in many CNS and non-CNS pathways (*Celanire S, Campo B, Expert Opinion in Drug Discovery*, 2012)

The similarity in the ligand binding domains of group III mGluRs creates a challenge for identifying selective orthosteric agonists of this receptor, although some progress has been made in this area. However, targeting positive allosteric modulators (PAMs) rather than orthosteric agonists provides a broader opportunity to identify molecules that are exclusively selective between mGluRs.

mGluR4 PAMs are emerging as promising therapeutic agents for the treatment of motor (and non motor) symptoms as well as a disease-modifying agent in Parkinson's disease through a non-dopaminergic approach.

Parkinson's disease is a progressive neurodegenerative disease that results in the loss of dopaminergic neurons in the substantia nigra (SN). One consequence of the depletion of dopamine in this disease is a series of movement disorders, including bradykinesia, akinesia, tremor, gait disorders and problems with balance. These motor disturbances form the hallmark of PD, although there are many other non-motor symptoms that are associated with the disease. Early in the course of the disease, PD symptoms are effectively treated by dopamine replacement or augmentation, with the use of dopamine D2 receptor agonists, levodopa or monoamine oxidase B inhibitors. However, as the disease progresses these agents become less effective in controlling motor symptoms. Additionally, their use is limited by the emergence of adverse effects including dopamine agonist-induced dyskinesias. Consequently, there remains a need for new approaches to the treatment of PD that improve the effectiveness of the control of motor symptoms.

Activation of metabotropic glutamate receptor 4 (mGluR4) has been proposed as a potential therapeutic approach to Parkinson's disease. A member of the group III mGluRs, mGluR4 is predominantly a presynaptic glutamate receptor that is expressed in several key locations in the basal ganglia circuits that control movement. Activation of mGluR4 with group III-preferring agonists decreases inhibitory and excitatory post synaptic potentials, presumably by decreasing the release of GABA and glutamate respectively.

The search for novel drugs that relieve motor symptoms of Parkinsonism whilst attenuating the ongoing degeneration of nigrostriatal neurons is of particular interest. Orthosteric mGluR4 agonist L-AP4 has demonstrated neuroprotective effects in a 6-OHDA rodent model of PD and first positive allosteric modulator (–)-PHCCC reduced nigrostriatal degeneration in mice treated with 1-Methyl-4-Phenyl-1,2,3,6-Tetrahydropyridine (MPTP). These studies provide convincing preclinical evidence suggesting that mGluR4 activators constitute a valid approach not only for symptomatic treatments of PD, but also potentially as disease modifiers for this indication.

The neuroprotective effects of selective mGluR4 modulators was also described in *Neuroreport*, 19(4), 475-8, 2008, *Proc.Natl. Acad. Sci, USA*, 100(23), 13668-73, 2003 and *J.Neurosci.* 26(27), 7222-9, 2006 and Mol. Pharmacol. 74(5), 1345-58, 2008.

Anxiety disorders are among the most prevalent psychiatric disorders in the world, and are co-morbid with Parkinson's disease (*Prediger R, et al. Neuropharmacology* 2012; 62: 115-24). Excessive glutamatergic neurotransmission is one important feature of anxiety pathophysiology. Based on presynaptic localization of mGluR4 in brain areas involved in anxiety and mood disorders, and dampening excessive brain excitability, the mGluR4 activators may represent a new generation of anxiolytic therapeutics (*Eur. J. Pharmacol.,* 498(1-3), 153-6, 2004).

Addex has reported in 2010 that ADX88178 was active in two preclinical rodent models of anxiety: the marble burying test in mice and EPM in mice and rats. ADX88178 also displayed an anxiolytic-like profile in the rat EPM test after oral dosing.

mGluR4 modulators were also shown to exert anti-depressive actions (*Neuropharmacology,* 46(2), 151-9, 2004).

In addition, mGluR4 modulators were also shown to be involved in glucagon secretion inhibition (*Diabetes,* 53(4), 998-1006, 2004). Therefore, orthosteric or positive allosteric modulators of mGluR4 have potential for the treatment of type 2 diabetes through its hypoglycemic effect.

Moreover, mGluR4 was shown to be expressed in prostate cancer cell-line (*Anticancer Res.* 29(1), 371-7, 2009) or colorectal carcinoma (*Cli. Cancer Research,* 11(9)3288-95, 2005). mGluR4 modulators may therefore have also potential role for the treatment of cancers.

Other proposed effects of mGluR4 PAM's can be expected for the treatment of emesis, obsessive compulsive disorder, anorexia and autism.

SUMMARY OF THE INVENTION

Compounds of formula I are distinguished by having valuable therapeutic properties. They can be used in the treatment or prevention of disorders, relating to allosteric modulators for the mGluR4 receptor.

The most preferred indications for compounds which are allosteric modulators for the mGluR4 receptor are Parkinson's disease, anxiety, emesis, obsessive compulsive disorder, anorexia, autism, neuroprotection, cancer, depression and type 2 diabetes.

The present invention relates to compounds of formula I and to their pharmaceutically acceptable salts, to these compounds as pharmaceutically active substances, to the processes for their production as well as to their use in the treatment or prevention of disorders, relating to allosteric modulators for the mGluR4 receptor, such as Parkinson's disease, anxiety, emesis, obsessive compulsive disorder, autism, neuroprotection, cancer, depression and diabetes typ 2 and to pharmaceutical compositions containing the compounds of formula I.

A further object of the present invention is a method for the treatment or prophylaxis of Parkinson's disease, anxiety, emesis, obsessive compulsive disorder, anorexia, autism, neuroprotection, cancer, depression and type 2 diabetes , which method comprises administering an effective amount of a compound of formula I to a mammal in need.

Furthermore, the invention includes all racemic mixtures, all their corresponding enantiomers and/or optical isomers, or analogues containing isotopes of hydrogen, fluorine, carbon, oxygen or nitrogen.

BRIEF DESCRIPTION OF THE DRAWING

FIG. 1: Illustration of the experimental outline for mGlu4 PAM Ca2+ mobilization screening assay and the determination of $EC_{50}$ and % Emax values.

DETAILED DESCRIPTION OF THE INVENTION

The following definitions of the general terms used in the present description apply irrespective of whether the terms in question appear alone or in combination. As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is linked with an O atom.

As used herein, the term "lower alkoxyalkyl" denotes a lower alkoxy group as defined above, which is linked with a lower alkyl group.

The term "cycloalkyl" denotes a saturated ring containing from 3 to 7 carbon atoms, for example cyclopropyl, cyclobutyl, cyclopentyl, cyclopentenyl, cyclohexyl, cyclohexenyl, cycloheptyl or cycloheptenyl.

The term "halogen" denotes chlorine, iodine, fluorine and bromine.

The term "lower alkyl substituted by halogen" denotes a lower alkyl group as defined above, wherein at least one hydrogen atom is replaced by a halogen atom, for example the following groups: $CF_3$, $CHF_2$, $CH_2F$, $CH_2CF_3$, $CH_2CHF_2$, $CH_2CH_2F$, $CH_2CH_2CF_3$, $CH_2CH_2CH_2CF_3$, $CH_2CH_2Cl$, $CH_2CF_2CF_3$, $CH_2CF_2CHF_2$, $CF_2CHFCF_3$, $C(CH_3)_2CF_3$, $CH(CH_3)CF_3$ or $CH(CH_2F)CH_2F$. The preferred "lower alkyl substituted by halogen" group is $CF_3$.

The term "or $R^2$ forms together with $R^4$ a 6 membered heterocyclic ring containing —$CH_2$—$CH_2$—O—$CH_2$— or —$CH_2$—$CH_2$—NR—C(O)—" means

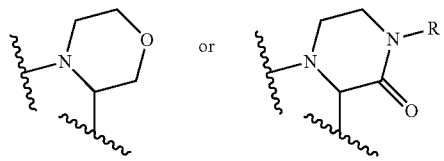

and R is as described above.

The term "or $R^4$ forms together with $R^{4'}$ a 4, 5 or 6 membered heterocyclic ring containing —$(CH_2)_5$—, —$CH_2$—$CH_2$—O—$CH_2$—$CH_2$—, —$CH_2$—$CH_2$—$CH_2$—, —$CH_2$—$CH_2$—$CH_2$—$CH_2$—, —$CH_2$—O—$CH_2$—$CH_2$— or $CH_2$—$CH_2$—$CH_2$—O—$CH_2$ means

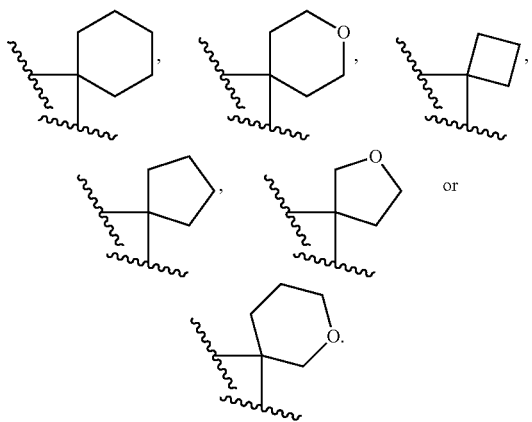

The term "or $R^4$ forms together with $R^5$ a saturated 5-membered ring containing —$CH_2$—$CH_2$—$CH_2$—" means

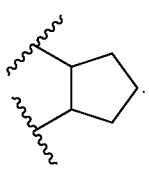

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention regards compounds of formula IA

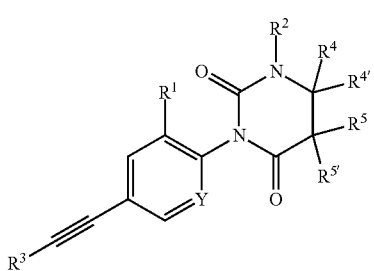

IA wherein
Y is N or C—$R^{1'}$;
$R^{1'}$ is hydrogen or F;
$R^1$ is hydrogen, halogen or lower alkyl substituted by halogen;
$R^2$ is hydrogen or lower alkyl;
$R^3$ is phenyl or pyridinyl, wherein the N atom in the pyridinyl group may be in different positions;
$R^{4'}$ is hydrogen, lower alkyl or lower alkoxyalkyl;
$R^4$ is hydrogen, lower alkyl, phenyl optionally substituted by halogen or lower alkoxy, or is cycloalkyl, or is pyridinyl optionally substituted by halogen, lower alkyl, lower alkoxy or =O, or is pyrimidinyl optionally substituted by lower alkyl, lower alkoxy or =O, or is 1-lower alkyl-pyridinyl, or is pyrazinyl, or is pyridazinyl optionally substituted by lower alkyl, lower alkoxy or =O, or is 1-methylpyrrolo[2,3-b]pyridine-5-yl, or is 6-imidazo[1,2-b]pyridazin-6-yl; $R^5$ and $R^{5'}$ are hydrogen or lower alkyl;
or a pharmaceutically acceptable salt or acid addition salt, a racemic mixture, or its corresponding enantiomer and/or optical isomer and/or stereoisomer thereof, for example the following compounds:
3-[2,6-difluoro-4-(2-phenylethynyl)phenyl]-1,6,6-trimethyl-hexahydropyrimidine-2,4-dione
3-[2-chloro-4-(2-phenylethynyl)phenyl]-1,6,6-trimethyl-hexahydropyrimidine-2,4-dione
(5RS)-3-[2,6-difluoro-4-(2-phenylethynyl)phenyl]-1,5,6,6-tetramethyl-hexahydropyrimidine-2,4-dione
3-[2-chloro-6-fluoro-4-[2-(3-pyridyl)ethynyl]phenyl]-1,6,6-trimethyl-hexahydropyrimidine-2,4-dione
3-[2-chloro-6-fluoro-4-[2-(3-pyridyl)ethynyl]phenyl]-1-ethyl-6,6-dimethyl-hexahydropyrimidine-2,4-dione
(6RS)-3-[2,6-difluoro-4-(2-phenylethynyl)phenyl]-1,6-dimethyl-6-phenyl-hexahydropyrimidine-2,4-dione
(6RS)-3-[2,6-difluoro-4-(2-phenylethynyl)phenyl]-1,6-dimethyl-6-phenyl-hexahydropyrimidine-2,4-dione
(6RS)-3-[2,6-difluoro-4-[2-(3-pyridyl)ethynyl]phenyl]-1-ethyl-6-methyl-6-phenyl-hexahydropyrimidine-2,4-dione
(6RS)-3-[2,6-difluoro-4-(2-phenylethynyl)phenyl]-6-ethyl-1,6-dimethyl-hexahydropyrimidine-2,4-dione
(6S)-3-[2,6-difluoro-4-(2-phenylethynyl)phenyl]-1,6-dimethyl-6-phenyl-hexahydropyrimidine-2,4-dione
(6R)-3-[2,6-difluoro-4-(2-phenylethynyl)phenyl]-1,6-dimethyl-6-phenyl-hexahydropyrimidine-2,4-dione
3-[2,6-difluoro-4-(2-phenylethynyl)phenyl]-6,6-diethyl-hexahydropyrimidine-2,4-dione
3-[2,6-difluoro-4-(2-phenylethynyl)phenyl]-6,6-diethyl-1-methyl-hexahydropyrimidine-2,4-dione
(6RS)-1,6-dimethyl-6-phenyl-3-[5-(2-phenylethynyl)-2-pyridyl]hexahydropyrimidine-2,4-dione
(6RS)-1,6-dimethyl-6-phenyl-3-[4-(2-phenylethynyl)phenyl]hexahydropyrimidine-2,4-dione
(6RS)-3-[2,6-difluoro-4-(2-phenylethynyl)phenyl]-6-isopropyl-1,6-dimethyl-hexahydropyrimidine-2,4-dione
(6RS)-3-[2,6-difluoro-4-(2-phenylethynyl)phenyl]-1,6-dimethyl-6-(2-pyridyl)hexahydropyrimidine-2,4-dione
(6RS)-3-[2,6-difluoro-4-(2-phenylethynyl)phenyl]-1,6-dimethyl-6-(4-pyridyl)hexahydropyrimidine-2,4-dione
(6RS)-3-[2,6-difluoro-4-(2-phenylethynyl)phenyl]-1,6-dimethyl-6-(3-pyridyl)hexahydropyrimidine-2,4-dione
(6RS)-3-[2,6-difluoro-4-(2-phenylethynyl)phenyl]-6-(methoxymethyl)-1,6-dimethyl-hexahydropyrimidine-2,4-dione
(6RS)-6-cyclohexyl-3-[2,6-difluoro-4-[2-(3-pyridyl)ethynyl]phenyl]-1,6-dimethyl-hexahydropyrimidine-2,4-dione
(6RS)-3-[3-chloro-5-(2-phenylethynyl)-2-pyridyl]-1,6-dimethyl-6-phenyl-hexahydropyrimidine-2,4-dione
(6RS)-3-[2-chloro-6-fluoro-4-[2-(3-pyridyl)ethynyl]phenyl]-1,6-dimethyl-6-(3-pyridyl)hexahydropyrimidine-2,4-dione
(6RS)-3-[2-chloro-6-fluoro-4-[2-(3-pyridyl)ethynyl]phenyl]-1,6-dimethyl-6-phenyl-hexahydropyrimidine-2,4-dione
(6RS)-6-(3-chlorophenyl)-3-[2,6-difluoro-4-[2-(3-pyridyl)ethynyl]phenyl]-1,6-dimethyl-hexahydropyrimidine-2,4-dione
(6RS)-6-(2-chlorophenyl)-3-[2,6-difluoro-4-[2-(3-pyridyl)ethynyl]phenyl]-1,6-dimethyl-hexahydropyrimidine-2,4-dione
(6RS)-6-(4-chlorophenyl)-3-[2,6-difluoro-4-[2-(3-pyridyl)ethynyl]phenyl]-1,6-dimethyl-hexahydropyrimidine-2,4-dione
(6RS)-3-[2,6-difluoro-4-[2-(3-pyridyl)ethynyl]phenyl]-6-(3-methoxyphenyl)-1,6-dimethyl-hexahydropyrimidine-2,4-dione
(6RS)-6-tert-butyl-3-[2,6-difluoro-4-(2-phenylethynyl)phenyl]-6-methyl-hexahydropyrimidine-2,4-dione
(6RS)-6-tert-butyl-3-[2,6-difluoro-4-(2-phenylethynyl)phenyl]-1,6-dimethyl-hexahydropyrimidine-2,4-dione
(6RS)-3-[3-fluoro-5-(2-phenylethynyl)-2-pyridyl]-1,6-dimethyl-6-phenyl-hexahydropyrimidine-2,4-dione
(6RS)-1,6-dimethyl-6-phenyl-3-[5-(2-phenylethynyl)-3-(trifluoromethyl)-2-pyridyl]hexahydropyrimidine-2,4-dione
(6RS)-3-[2-Chloro-4-(2-phenylethynyl)phenyl]-1,6-dimethyl-6-(3-pyridyl)hexahydropyrimidine-2,4-dione
(6RS)-3-[2,6-Difluoro-4-[2-(3-pyridyl)ethynyl]phenyl]-6-ethyl-1-methyl-6-phenyl-hexahydropyrimidine-2,4-dione
(6S)-3-[2,6-Difluoro-4-(2-phenylethynyl)phenyl]-1,6-dimethyl-6-(3-pyridyl)hexahydropyrimidine-2,4-dione
(6S)-3-[3-Fluoro-5-(2-phenylethynyl)-2-pyridyl]-1,6-dimethyl-6-(3-pyridyl)hexahydropyrimidine-2,4-dione (6RS)-6-(6-Chloro-3-pyridyl)-3-[2,6-difluoro-4-(2-phenylethynyl)phenyl]-1,6-dimethyl-hexahydropyrimidine-2,4-dione (6S)-3-[2,6-Difluoro-4-(2-phenylethynyl)phenyl]-1-ethyl-6-methyl-6-(3-pyridyl)hexahydropyrimidine-2,4-dione (6S)-3-[2,6-Difluoro-4-[2-(3-pyridyl)ethynyl]phenyl]-1,6-dimethyl-6-(3-pyridyl)hexahydropyrimidine-2,4-dione (6S)-3-[2,6-Difluoro-4-(2-phenylethynyl)phenyl]-1,6-dimethyl-6-(6-methyl-3-pyridyl)hexahydropyrimidine-2,4-dione (6S)-3-[2,6-Difluoro-4-(2-phenylethynyl)phenyl]-1,6-dimethyl-6-pyrimidin-4-yl-hexahydropyrimidine-2,4-dione (6S)-3-[2,6-Difluoro-4-(2-phenylethynyl)phenyl]-1,6-dimethyl-6-pyrimidin-5-yl-hexahydropyrimidine-2,4-dione (6S)-3-[2,6-Difluoro-4-(2-phenylethynyl)phenyl]-1,6-dimethyl-6-pyrazin-2-yl-hexahydropyrimidine-2,4-dione (6S)-3-[2,6-Difluoro-4-(2-phenylethynyl)phenyl]-1,6-dimethyl-6-pyridazin-3-yl-hexahydropyrimidine-2,4-dione (6S)-3-[2,6-Difluoro-4-(2-phenylethynyl)phenyl]-6-(5-fluoro-3-pyridyl)-1,6-dimethyl-hexahydropyrimidine-2,4-dione (6S)-6-(2-Chloro-4-pyridyl)-3-[2,6-difluoro-4-(2-phenylethynyl)phenyl]-1,6-dimethyl-hexahydropyrimidine-2,4-dione (6S)-3-[2,6-Difluoro-4-(2-phenylethynyl)phenyl]-1,6-dimethyl-6-pyridazin-4-yl-hexahydropyrimidine-2,4-dione (6S)-3-[2,6-Difluoro-4-(2-phenylethynyl)phenyl]-1,6-dimethyl-6-(2-methyl-4-pyridyl)hexahydropyrimidine-2,4-dione (6S)-3-[2,6-Difluoro-4-(2-phenylethynyl)phenyl]-6-(6-methoxy-3-pyridyl)-1,6-dimethyl-hexahydropyrimidine-2,4-dione (6S)-6-(2-Chloro-4-pyridyl)-3-[2,6-difluoro-4-[2-(3-pyridyl)ethynyl]phenyl]-1,6-dimethyl-hexahydropyrimidine-2,4-dione (6S)-3-[2,6-Difluoro-4-(2-phenylethynyl)phenyl]-1,6-dimethyl-6-(6-oxo-1H-pyridin-3-yl)hexahydropyrimidine-2,4-dione (6S)-3-[2,6-Difluoro-4-(2-phenylethynyl)phenyl]-1,6-dimethyl-6-(1-methyl-6-oxo-3-pyridyl)hexahydropyrimidine-2,4-dione (6S)-3-[2,6-Difluoro-4-(2-phenylethynyl)phenyl]-6-(1-ethyl-6-oxo-3-pyridyl)-1,6-dimethyl-hexahydropyrimidine-2,4-dione (6S)-3-[2,6-Difluoro-4-(2-phenylethynyl)phenyl]-6-(1-isopropyl-6-oxo-3-pyridyl)-1,6-dimethyl-hexahydropyrimidine-2,4-dione (6S)-3-[2,6-Difluoro-4-(2-phenylethynyl)phenyl]-6-(6isopropoxy-3-pyridyl)-1,6-dimethyl-hexahydropyrimidine-2,4-dione (6S)-3-[2,6-Difluoro-4-(2-phenylethynyl)phenyl]-1-isopropyl-6-methyl-6-(3-pyridyl)hexahydropyrimidine-2,4-dione (6S)-3-[2-Chloro-6-fluoro-4-(2-phenylethynyl)phenyl]-1,6-dimethyl-6-(3-pyridyl)hexahydropyrimidine-2,4-dione (6RS)-3-[2,6-Difluoro-4-[2-(3-pyridyl)ethynyl]phenyl]-1-methyl-6-phenyl-6-(trifluoromethyl)hexahydropyrimidine-2,4-dione (6S)-3-[2,6-Difluoro-4-(2-phenylethynyl)phenyl]-6-(2-methoxy-4-pyridyl)-1,6-dimethyl-hexahydropyrimidine-2,4-dione (6S)-3-[2,6-Difluoro-4-(2-phenylethynyl)phenyl]-1,6-dimethyl-6-(2-oxo-1H-pyridin-4-yl)hexahydropyrimidine-2,4-dione (6S)-3-[2,6-Difluoro-4-(2-phenylethynyl)phenyl]-1,6-dimethyl-6-(1-methyl-2-oxo-4-pyridyl)hexahydropyrimidine-2,4-dione (6S)-3-[2,6-Difluoro-4-(2-phenylethynyl)phenyl]-1,6-dimethyl-6-(2-methylpyrimidin-4-yl)hexahydropyrimidine-2,4-dione (6S)-3-[2,6-Difluoro-4-(2-phenylethynyl)phenyl]-1-ethyl-6-methyl-6-(2-methyl-4-pyridyl)hexahydropyrimidine-2,4-dione (6S)-3-[2,6-Difluoro-4-(2-phenylethynyl)phenyl]-1,6-dimethyl-6-(4-pyridyl)hexahydropyrimidine-2,4-dione (6S)-3-[2,6-Difluoro-4-(2-phenylethynyl)phenyl]-6-(2-methoxypyrimidin-5-yl)-1,6-dimethyl-hexahydropyrimidine-2,4-dione(6S)-3-[2,6-Difluoro-4-(2-phenylethynyl)phenyl]-1,6-dimethyl-6-(2-oxo-1H-pyrimidin-5-yl)hexahydropyrimidine-2,4-dione (6S)-3-[2,6-Difluoro-4-(2-phenylethynyl)phenyl]-6-(6-methoxypyridazin-3-yl)-1,6-dimethyl-hexahydropyrimidine-2,4-dione (6S)-3-[2,6-Difluoro-4-(2-phenylethynyl)phenyl]-1,6-dimethyl-6-(6-oxo-1H-pyridazin-3-yl)hexahydropyrimidine-2,4-dione (6S)-3-[2,6-Difluoro-4-(2-phenylethynyl)phenyl]-1,6-dimethyl-6-(1-methyl-6-oxo-pyridazin-3-yl)hexahydropyrimidine-2,4-dione (6S)-3-[2,6-Difluoro-4-(2-phenylethynyl)phenyl]-1,6-dimethyl-6-(1-methylpyrrolo[2,3-b]pyridin-5-yl)hexahydropyrimidine-2,4-dione or (6S)-3-[2,6-Difluoro-4-(2-phenylethynyl)phenyl]-6-imidazo[1,2-b]pyridazin-6-yl-1,6-dimethyl-hexahydropyrimidine-2,4-dione.

One further object of the present invention regards compounds of formulas IB-1 and IB-2

I

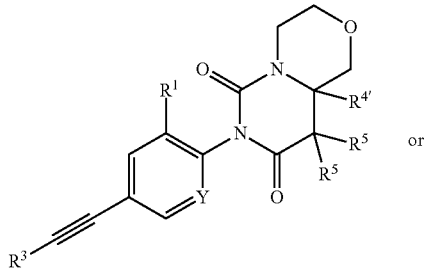

IB-1

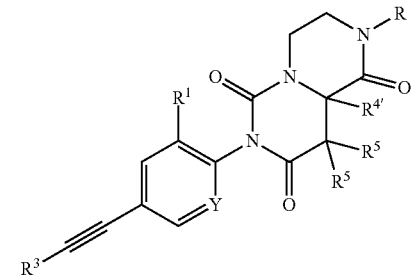

IB-2 wherein

Y is N or C—$R^{1'}$;

$R^{1'}$ is hydrogen or F;

$R^1$ is hydrogen, halogen or lower alkyl substituted by halogen;

R is hydrogen, lower alkyl, phenyl or benzyl;

$R^3$ is phenyl or pyridinyl, wherein the N atom in the pyridinyl group may be in different positions;

$R^{4'}$ is hydrogen, lower alkyl or lower alkoxyalkyl;

$R^5$ and $R^{5'}$ are hydrogen or lower alkyl;

or a pharmaceutically acceptable salt or acid addition salt, a racemic mixture, or its corresponding enantiomer and/or optical isomer and/or stereoisomer thereof, for example the following compounds:

(9aRS)-7-[2,6-difluoro-4-(2-phenylethynyl)phenyl]-3,4,9,9a-tetrahydro-1H-pyrimido[6,1-c][1,4]oxazine-6,8-dione (9aRS)-7-[2,6-difluoro-4-(2-phenylethynyl)phenyl]-9a-methyl-2,3,4,9-tetrahydropyrazino[1,2-c]pyrimidine-1,6,8-trione (9aRS)-7-[2,6-difluoro-4-(2-phenylethynyl)phenyl]-2,9a-dimethyl-4,9-dihydro-3H-pyrazino[1,2-c]pyrimidine-1,6,8-trione (9aRS)-7-[2,6-difluoro-4-(2-phenylethynyl)phenyl]-2-isopropyl-9a-methyl-4,9-dihydro-3H-pyrazino[1,2-c]pyrimidine-1,6,8-trione (9aRS)-2-benzyl-7-[2,6-difluoro-4-(2-phenylethynyl)phenyl]-9a-methyl-4,9-dihydro-3H-pyrazino[1,2-c]pyrimidine-1,6,8-trione (9aRS)-7-[2,6-difluoro-4-(2-phenylethynyl)phenyl]-9a-methyl-2-phenyl-4,9-dihydro-3H-pyrazino[1,2-c]pyrimidine-1,6,8-trione or (9aRS)-7-[2-Chloro-6-fluoro-4-(2-phenylethynyl)phenyl]-9a-methyl-2,3,4,9-tetrahydropyrazino[1,2-c]pyrimidine-1,6,8-trione.

One further object of the present invention regards compounds of formulas IC-1, IC-2, IC-3, IC-4, IC-5 and IC-6

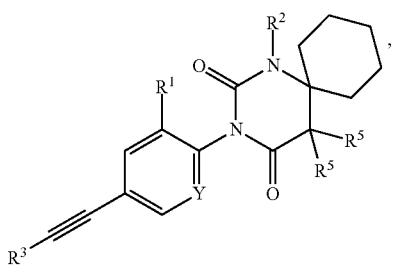

IC-1

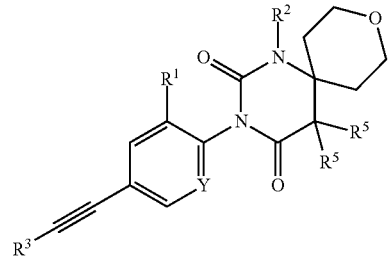

IC-2

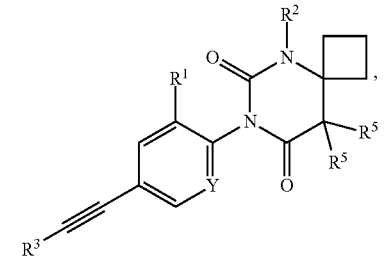

IC-3

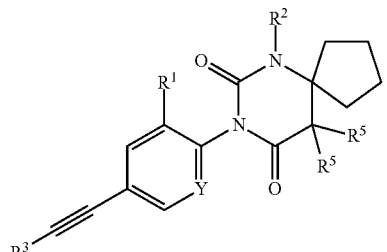

IC-4

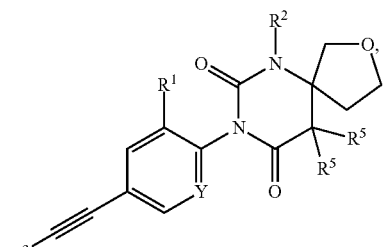

IC-5

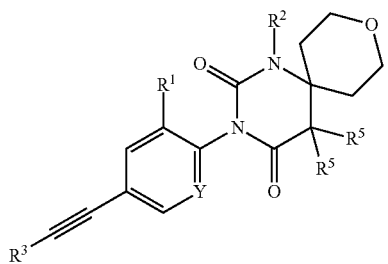

IC-6 wherein

Y is N or C—$R^{1'}$;

$R^{1'}$ is hydrogen or F;

$R^1$ is hydrogen, halogen or lower alkyl substituted by halogen;

$R^2$ is hydrogen or lower alkyl;

$R^3$ is phenyl or pyridinyl, wherein the N atom in the pyridinyl group may be in different positions;

$R^5$ and $R^{5'}$ are hydrogen or lower alkyl;

or a pharmaceutically acceptable salt or acid addition salt, a racemic mixture, or its corresponding enantiomer and/or optical isomer and/or stereoisomer thereof, for example the following compounds:

3-[2-chloro-4-(2-phenylethynyl)phenyl]-1-methyl-1,3-diazaspiro[5.5]undecane-2,4-dione 3-[2-chloro-4-(2-phenylethynyl)phenyl]-1-methyl-9-oxa-1,3-diazaspiro[5.5]undecane-2,4-dione 7-[2-chloro-4-(2-phenylethynyl)phenyl]-5-methyl-5,7-diazaspiro[3.5]nonane-6,8-dione 8-[2,6-difluoro-4-(2-phenylethynyl)phenyl]-6-methyl-6,8-diazaspiro[4.5]decane-7,9-dione (5RS)-8-[2,6-difluoro-4-(2-phenylethynyl)phenyl]-6-methyl-2-oxa-6,8-diazaspiro[4.5]decane-7,9-dione or (6RS)-3-[2,6-difluoro-4-(2-phenylethynyl)phenyl]-1-methyl-8-oxa-1,3-diazaspiro[5.5]undecane-2,4-dione.

One further object of the present invention regards compounds of formulas ID

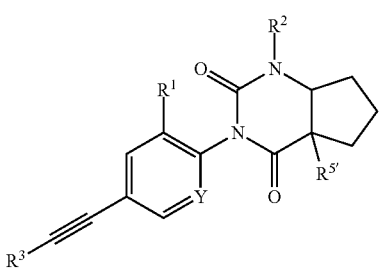

wherein
Y is N or C—R$^{1'}$;
R$^{1'}$ is hydrogen or F;
R$^1$ is hydrogen, halogen or lower alkyl substituted by halogen;
R$^2$ is hydrogen or lower alkyl;
R$^3$ is phenyl or pyridinyl, wherein the N atom in the pyridinyl group may be in different positions;
R$^{5'}$ is hydrogen or lower alkyl;
or a pharmaceutically acceptable salt or acid addition salt, a racemic mixture, or its corresponding enantiomer and/or optical isomer and/or stereoisomer thereof, for example the following compounds:
(4aRS,7aSR)-3-[2,6-difluoro-4-(2-phenylethynyl)phenyl]-1-methyl-5,6,7,7a-tetrahydro-4aH-cyclopenta[d]pyrimidine-2,4-dione or
(4aRS,7aRS)-3-[2,6-difluoro-4-(2-phenylethynyl)phenyl]-1,7a-dimethyl-4a,5,6,7-tetrahydrocyclopenta[d]pyrimidine-2,4-dione.

The preparation of compounds of formula I of the present invention may be carried out in sequential or convergent synthetic routes. Syntheses of the compounds of the invention are shown in the following schemes 1 and 2. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises
a) alkylating a compound of formula

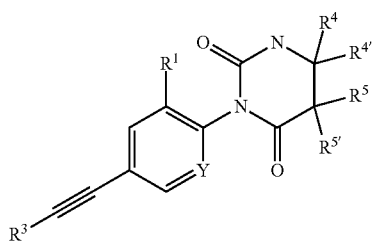

with R$^2$-I in the presence of NaH or Cs$_2$CO$_3$ in DMF to a compound of formula

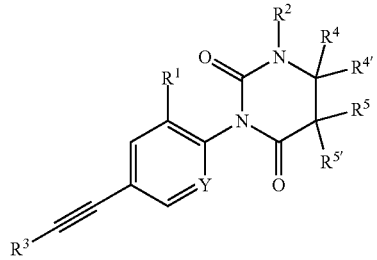

wherein the substituents are described above, or
if desired, converting the compounds obtained into pharmaceutically acceptable acid addition salts.

EXAMPLES

The preparation of compounds of formula I is further described in more detail in scheme 1 and 2 and in examples 1-86.

Scheme 1

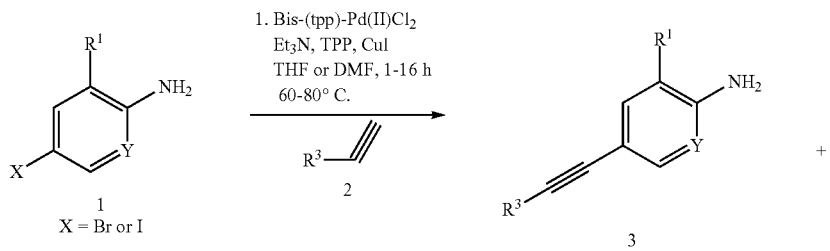

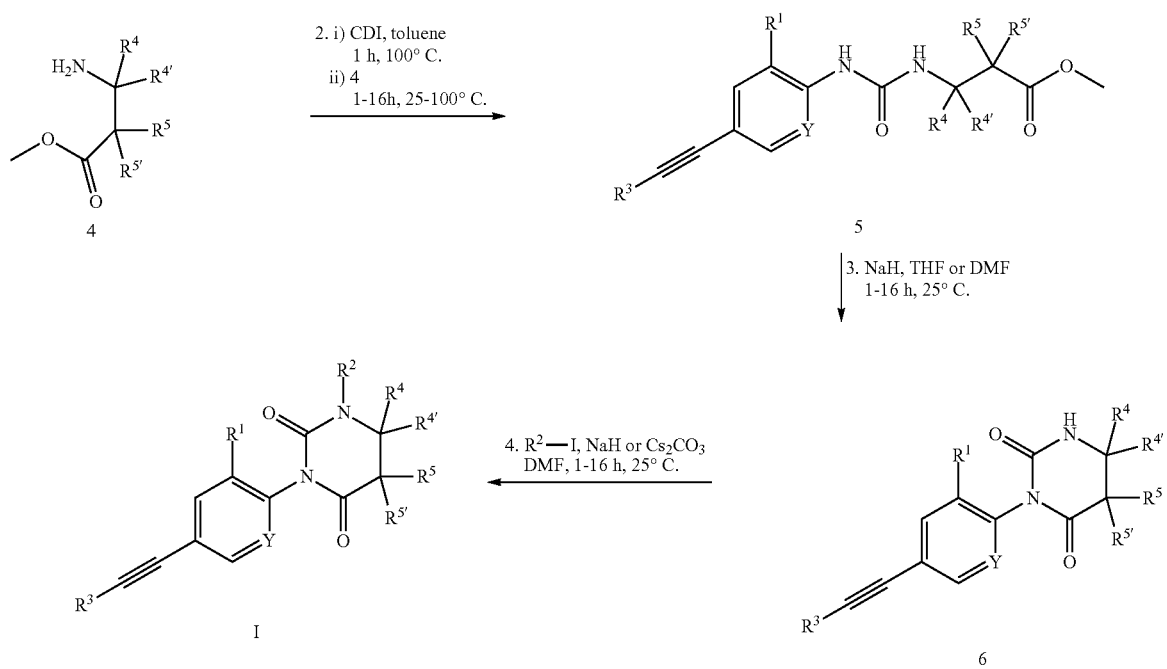

An ethynyl-phenyl, ethynyl-pyridyl substituted pyrimidine-2,4-dione compound of general formula I can be obtained for example by Sonogashira coupling of an appropriately substituted aniline or aminopyridine 1 with an appropriately substituted arylacetylene 2 to yield the desired ethynyl compounds of formula 3. Reacting ethynyl compounds of formula 3 with an appropriately substituted aminoester of formula 4 with phosgene or a phosgene equivalent such as triphosgene or carbonyldiimidazole (CDI) in presence or absence of a base such as triethylamine in a solvent such as toluene or dioxane forms the desired urea analogues of formula 5. Ring closure of 5 with a strong base such as NaH or KOtBu in a solvent like THF or DMF forms the desired pyrimidine-2,4-dione compounds of formula 6. Introduction of the $R^2$ substituent via alkylation forms the desired ethynyl-phenyl, ethynyl-pyridyl substituted pyrimidine-2,4-dione compound of general formula I (scheme 1).

Generally speaking, the sequence of steps used to synthesize the compounds of formula I can also be modified in certain cases.

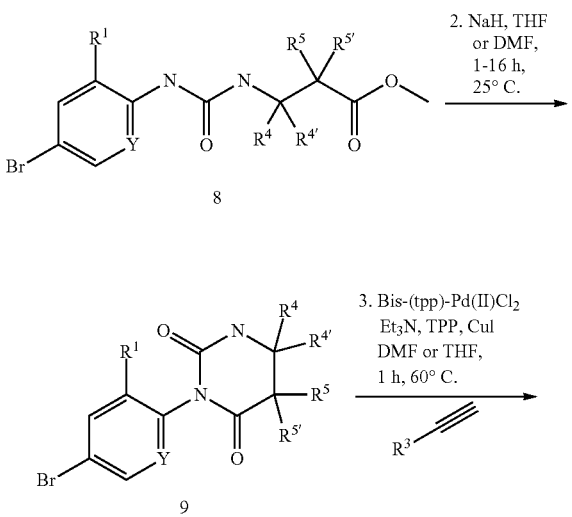

Scheme 2

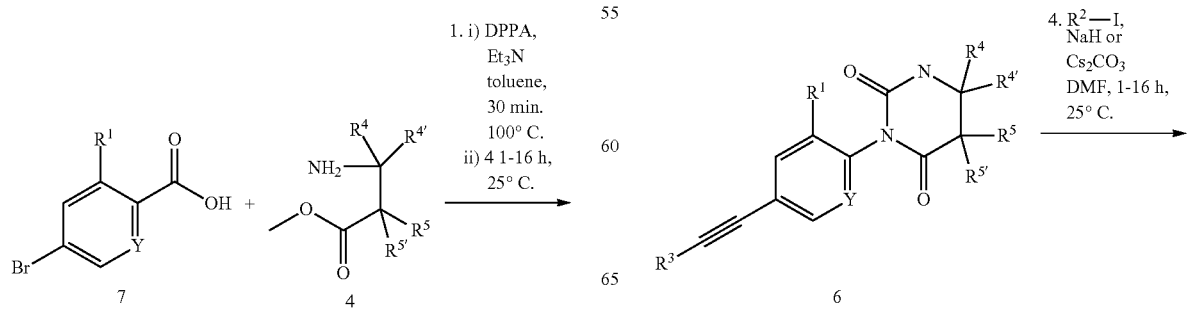

-continued

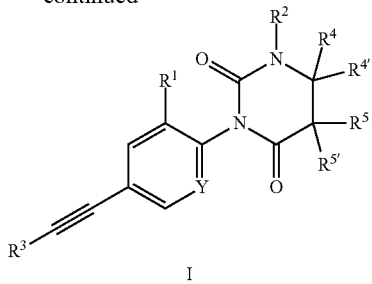

I

An ethynyl-phenyl, ethynyl-pyridyl substituted pyrimidine-2,4-dione compound of general formula I can also be obtained for example by reacting an appropriately substituted acid 7 with DPPA to form the corresponding isocyanate which is then reacted with an appropriately substituted aminoester of formula 4 in presence of a base such as triethylamine in a solvent such as toluene to yield the desired urea analogue of formula 8. Ring closure of 8 with a strong base such as NaH or KOtBu in a solvent like THF or DMF forms the desired pyrimidine-2,4-dione compounds of formula 9. Sonogashira coupling of compounds 9 with an appropriately substituted arylacetylene 2 yields the desired ethynyl compounds of formula 6. Introduction of the $R^2$ substituent via alkylation forms the desired ethynyl-phenyl, ethynyl-pyridyl substituted pyrimidine-2,4-dione compound of general formula I (scheme 2).

Generally speaking, the sequence of steps used to synthesize the compounds of formula I can also be modified in certain cases.

Biological Assay and Data

Determination of $EC_{50}$ Values Using a Ca2+ mobilization in vitro Assay on Recombinant Human mGlu4 Expressed in HEK293 cells:

A monoclonal HEK-293 cell line stably transfected with a cDNA encoding for the human mGlu4 receptor was generated; for the work with mGlu4 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist (2S)-2-amino-4-phosphonobutanoic acid (L-AP4) was added to the cells at a concentration corresponding to $EC_{20}$ with on-line recording of fluorescence; in order to account for day-to-day variations in the responsiveness of cells, the $EC_{20}$ of L-AP4 was determined immediately ahead of each experiment by recording of a full dose-response curve of L-AP4.

Responses were measured as peak increase in fluorescence minus basal (i.e. fluorescence without addition of L-AP4), normalized to the maximal stimulatory effect obtained with saturating concentrations of L-AP4. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (drug concentration at which 50% of the maximal receptor activation was achieved), the Hill coefficient as well as the maximal response in % of the maximal stimulatory effect obtained with saturating concentrations of L-AP4 were calculated (see FIG. 1).

Positive signals obtained during the pre-incubation with the PAM test compounds (i.e. before application of an $EC_{20}$ concentration of L-AP4) were indicative of an agonistic activity, the absence of such signals were demonstrating the lack of agonistic activities. A depression of the signal observed after addition of the $EC_{20}$ concentration of L-AP4was indicative of an inhibitory activity of the test compound.

List of Examples and Data:

| | Structure | Name | $EC_{50}$ (nM) mGlu4 PAM | Eff. (%) |
|---|---|---|---|---|
| 1 | 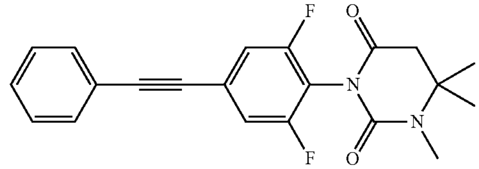 [SMILES: CN1C(=O)N(c2c(F)cc(C#Cc3ccccc3)cc2F)C(=O)CC1(C)C] | 3-[2,6-Difluoro-4-(2-phenylethynyl)phenyl]-1,6,6-trimethyl-hexahydropyrimidine-2,4-dione | 92 | 191 |
| 2 | 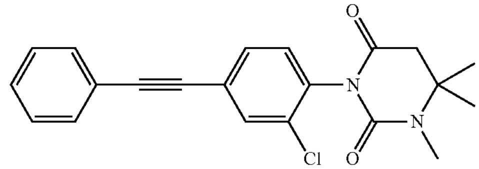 | 3-[2-Chloro-4-(2-phenylethynyl)phenyl]-1,6,6-trimethyl-hexahydropyrimidine-2,4-dione | 341 | 107 |

-continued

| | Structure | Name | EC$_{50}$ (nM) mGlu4 PAM | Eff. (%) |
|---|---|---|---|---|
| 3 | 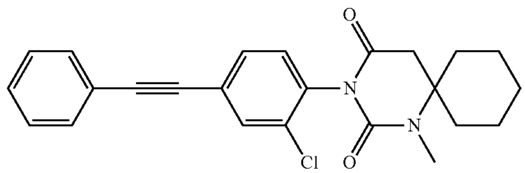 [SMILES: CN1C(=O)N(c2ccc(C#Cc3ccccc3)cc2Cl)C(=O)CC12CCCCC2] | 3-[2-Chloro-4-(2-phenylethynyl)phenyl]-1-methyl-1,3-diazaspiro[5.5]undecane-2,4-dione | 245 | 105 |
| 4 | 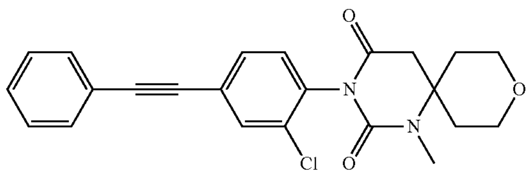 [SMILES: CN1C(=O)N(c2ccc(C#Cc3ccccc3)cc2Cl)C(=O)CC12CCOCC2] | 3-[2-Chloro-4-(2-phenylethynyl)phenyl]-1-methyl-9-oxa-1,3-diazaspiro[5.5]undecane-2,4-dione | 388 | 103 |
| 5 | 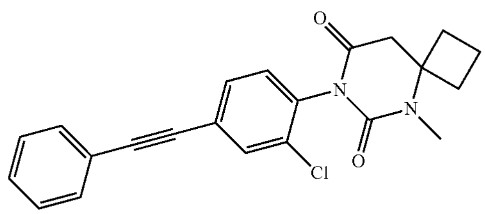 [SMILES: CN1C(=O)N(c2ccc(C#Cc3ccccc3)cc2Cl)C(=O)CC12CCC2] | 7-[2-Chloro-4-(2-phenylethynyl)phenyl]-5-methyl-5,7-diazaspiro[3.5]nonane-6,8-dione | 304 | 93 |
| 6 | 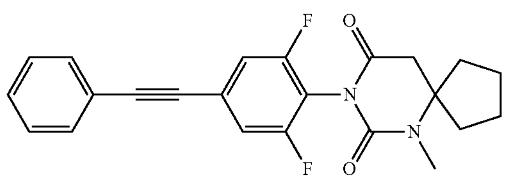 [SMILES: CN1C(=O)N(c2c(F)cc(C#Cc3ccccc3)cc2F)C(=O)CC12CCCC2] | 8-[2,6-Difluoro-4-(2-phenylethynyl)phenyl]-6-methyl-6,8-diazaspiro[4.5]decane-7,9-dione | 72 | 142 |
| 7 | 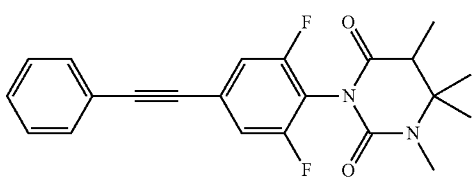 [SMILES: CC1C(=O)N(c2c(F)cc(C#Cc3ccccc3)cc2F)C(=O)N(C)C1(C)C] | (5RS)-3-[2,6-Difluoro-4-(2-phenylethynyl)phenyl]-1,5,6,6-tetramethyl-hexahydropyrimidine-2,4-dione | 157 | 148 |
| 8 | 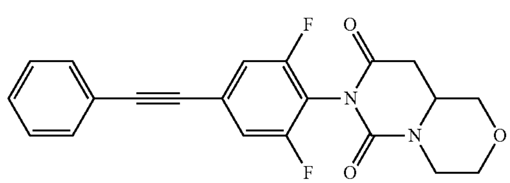 [SMILES: O=C1CC2COCCN2C(=O)N1c1c(F)cc(C#Cc2ccccc2)cc1F] | (9aRS)-7-[2,6-Difluoro-4-(2-phenylethynyl)phenyl]-3,4,9,9a-tetrahydro-1H-pyrimido[6,1-c][1,4]oxazine-6,8-dione | 144 | 107 |
| 9 | 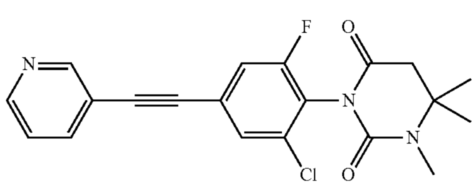 [SMILES: CN1C(=O)N(c2c(F)cc(C#Cc3cccnc3)cc2Cl)C(=O)CC1(C)C] | 3-[2-Chloro-6-fluoro-4-[2-(3-pyridyl)ethynyl]phenyl]-1,6,6-trimethyl-hexahydropyrimidine-2,4-dione | 429 | 110 |
| 10 | 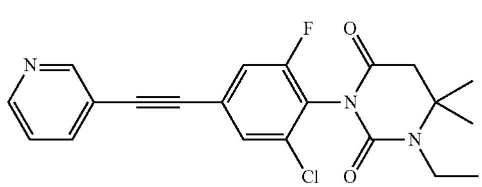 [SMILES: CCN1C(=O)N(c2c(F)cc(C#Cc3cccnc3)cc2Cl)C(=O)CC1(C)C] | 3-[2-Chloro-6-fluoro-4-[2-(3-pyridyl)ethynyl]phenyl]-1-ethyl-6,6-dimethyl-hexahydropyrimidine-2,4-dione | 256 | 169 |

-continued

| | Structure | Name | EC$_{50}$ (nM) mGlu4 PAM | Eff. (%) |
|---|---|---|---|---|
| 11 | 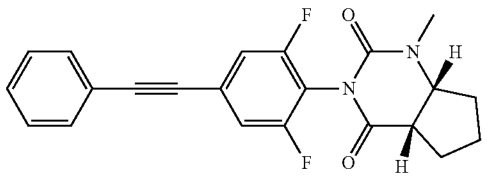 [SMILES: CN1C(=O)N(c2c(F)cc(C#Cc3ccccc3)cc2F)C(=O)[C@H]2CCC[C@H]21] | (4aRS,7aSR)-3-[2,6-Difluoro-4-(2-phenylethynyl)phenyl]-1-methyl-5,6,7,7a-tetrahydro-4aH-cyclopenta[d]pyrimidine-2,4-dione | 163 | 131 |
| 12 | 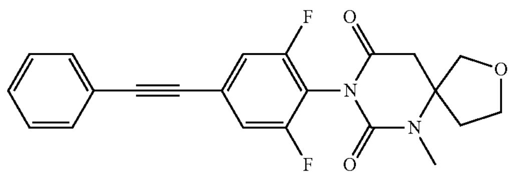 [SMILES: CN1C(=O)N(c2c(F)cc(C#Cc3ccccc3)cc2F)C(=O)CC12CCOC2] | (5RS)-8-[2,6-Difluoro-4-(2-phenylethynyl)phenyl]-6-methyl-2-oxa-6,8-diazaspiro[4.5]decane-7,9-dione | 260 | 115 |
| 13 | 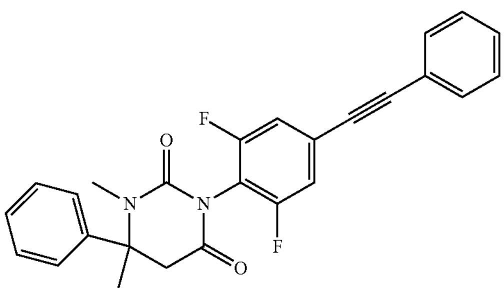 [SMILES: CN1C(=O)N(c2c(F)cc(C#Cc3ccccc3)cc2F)C(=O)CC1(C)c1ccccc1] | (6RS)-3-[2,6-Difluoro-4-(2-phenylethynyl)phenyl]-1,6-dimethyl-6-phenyl-hexahydropyrimidine-2,4-dione | 28 | 119 |
| 14 | 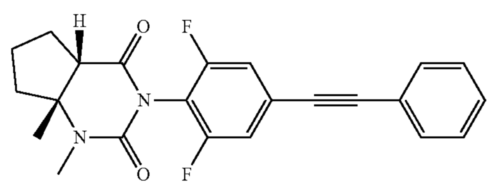 [SMILES: CN1C(=O)N(c2c(F)cc(C#Cc3ccccc3)cc2F)C(=O)[C@H]2CCC[C@]21C] | (4aRS,7aRS)-3-[2,6-Difluoro-4-(2-phenylethynyl)phenyl]-1,7a-dimethyl-4a,5,6,7-tetrahydrocyclopenta[d]pyrimidine-2,4-dione | 125 | 119 |
| 15 | 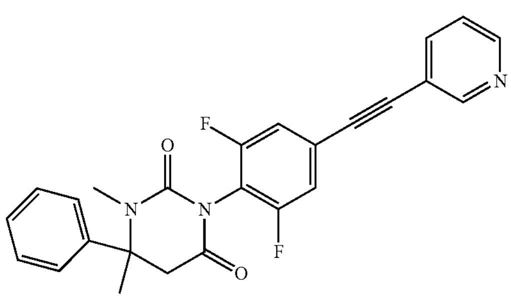 [SMILES: CN1C(=O)N(c2c(F)cc(C#Cc3cccnc3)cc2F)C(=O)CC1(C)c1ccccc1] | (6RS)-3-[2,6-Difluoro-4-[2-(3-pyridyl)ethynyl]phenyl]-1,6-dimethyl-6-phenyl-hexahydropyrimidine-2,4-dione | 100 | 134 |
| 16 | 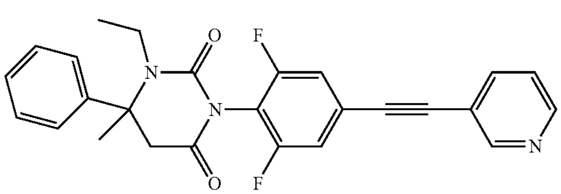 [SMILES: CCN1C(=O)N(c2c(F)cc(C#Cc3cccnc3)cc2F)C(=O)CC1(C)c1ccccc1] | (6RS)-3-[2,6-Difluoro-4-[2-(3-pyridyl)ethynyl]phenyl]-1-ethyl-6-methyl-6-phenyl-hexahydropyrimidine-2,4-dione | 105 | 136 |
| 17 | 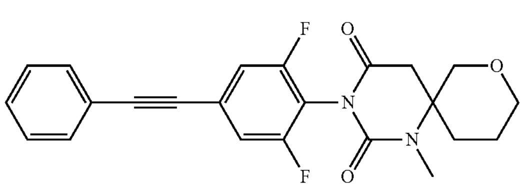 [SMILES: CN1C(=O)N(c2c(F)cc(C#Cc3ccccc3)cc2F)C(=O)CC12CCCOC2] | (6RS)-3-[2,6-Difluoro-4-(2-phenylethynyl)phenyl]-1-methyl-8-oxa-1,3-diazaspiro[5.5]undecane-2,4-dione | 183 | 129 |

-continued

| | Structure | Name | EC$_{50}$ (nM) mGlu4 PAM | Eff. (%) |
|---|---|---|---|---|
| 18 | 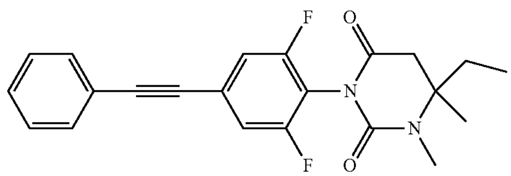 [SMILES: CCC1(C)CC(=O)N(c2c(F)cc(C#Cc3ccccc3)cc2F)C(=O)N1C] | (6RS)-3-[2,6-Difluoro-4-(2-phenylethynyl)phenyl]-6-ethyl-1,6-dimethyl-hexahydropyrimidine-2,4-dione | 49 | 241 |
| 19 | 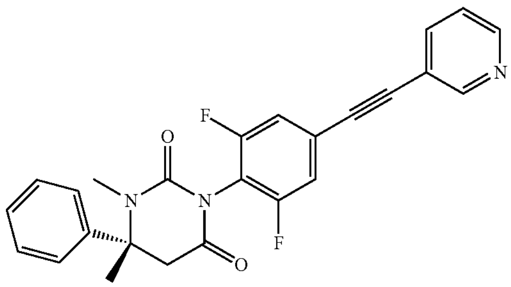 [SMILES: CN1C(=O)N(c2c(F)cc(C#Cc3cccnc3)cc2F)C(=O)C[C@]1(C)c1ccccc1] | (6S)-3-[2,6-Difluoro-4-[2-(3-pyridyl)ethynyl]phenyl]-1,6-dimethyl-6-phenyl-hexahydropyrimidine-2,4-dione | 50 | 178 |
| 20 | 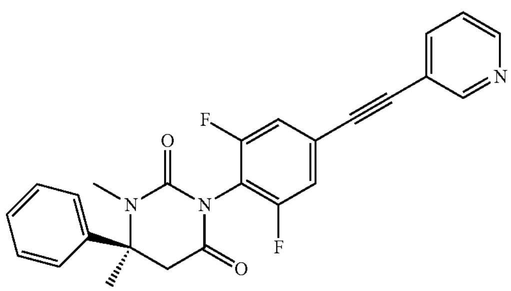 [SMILES: CN1C(=O)N(c2c(F)cc(C#Cc3cccnc3)cc2F)C(=O)C[C@@]1(C)c1ccccc1] | (6R)-3-[2,6-Difluoro-4-[2-(3-pyridyl)ethynyl]phenyl]-1,6-dimethyl-6-phenyl-hexahydropyrimidine-2,4-dione | 239 | 175 |
| 21 | 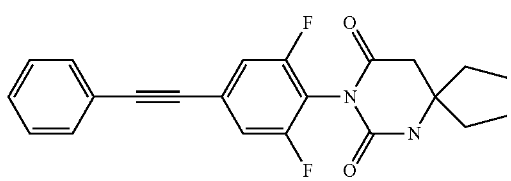 [SMILES: CCC1(CC)CC(=O)N(c2c(F)cc(C#Cc3ccccc3)cc2F)C(=O)N1] | 3-[2,6-Difluoro-4-(2-phenylethynyl)phenyl]-6,6-diethyl-hexahydropyrimidine-2,4-dione | 145 | 106 |
| 22 | 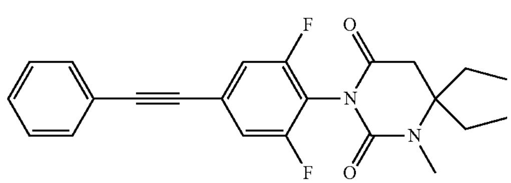 | 3-[2,6-Difluoro-4-(2-phenylethynyl)phenyl]-6,6-diethyl-1-methyl-hexahydropyrimidine-2,4-dione | 73 | 137 |
| 23 | 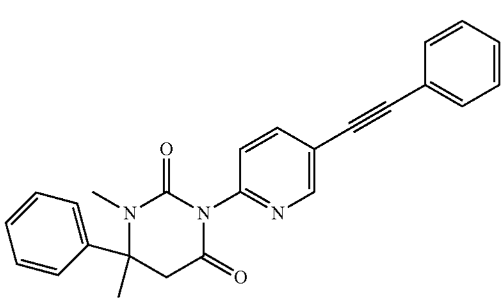 [SMILES: CN1C(=O)N(c2ccc(C#Cc3ccccc3)cn2)C(=O)CC1(C)c1ccccc1] | (6RS)-1,6-Dimethyl-6-phenyl-3-[5-(2-phenylethynyl)-2-pyridyl]hexahydropyrimidine-2,4-dione | 947 | 126 |

-continued

| | Structure | Name | EC$_{50}$ (nM) mGlu4 PAM | Eff. (%) |
|---|---|---|---|---|
| 24 | 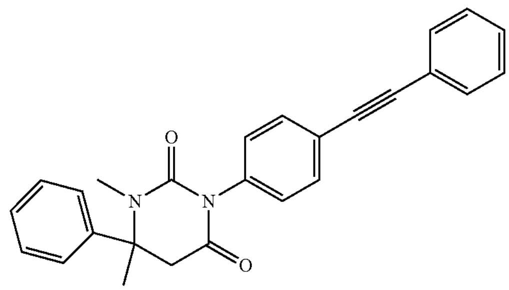 [SMILES: CN1C(=O)N(c2ccc(C#Cc3ccccc3)cc2)C(=O)CC1(C)c1ccccc1] | (6RS)-1,6-Dimethyl-6-phenyl-3-[4-(2-phenylethynyl)phenyl]hexahydropyrimidine-2,4-dione | 254 | 126 |
| 25 | 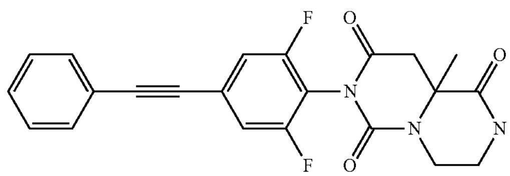 [SMILES: CC12CC(=O)N(c3c(F)cc(C#Cc4ccccc4)cc3F)C(=O)N1CCNC2=O] | (9aRS)-7-[2,6-Difluoro-4-(2-phenylethynyl)phenyl]-9a-methyl-2,3,4,9-tetrahydropyrazino[1,2-c]pyrimidine-1,6,8-trione | 83 | 105 |
| 26 | 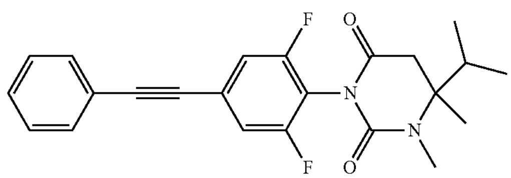 | (6RS)-3-[2,6-Difluoro-4-(2-phenylethynyl)phenyl]-6-isopropyl-1,6-dimethyl-hexahydropyrimidine-2,4-dione | 64 | 107 |
| 27 | 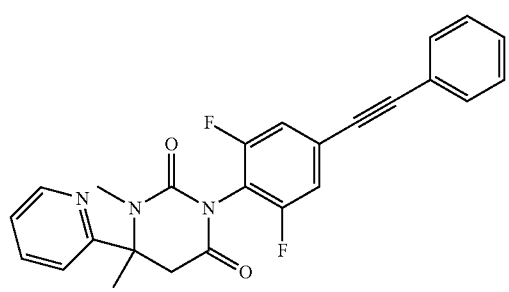 [SMILES: CN1C(=O)N(c2c(F)cc(C#Cc3ccccc3)cc2F)C(=O)CC1(C)c1ccccn1] | (6RS)-3-[2,6-Difluoro-4-(2-phenylethynyl)phenyl]-1,6-dimethyl-6-(2-pyridyl)hexahydropyrimidine-2,4-dione | 72 | 99 |
| 28 | 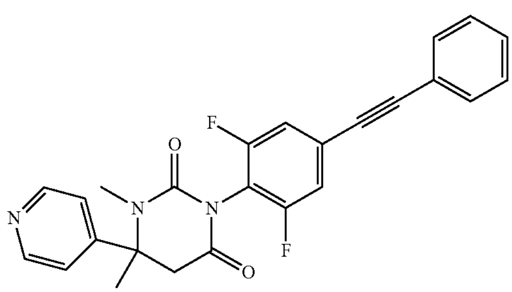 [SMILES: CN1C(=O)N(c2c(F)cc(C#Cc3ccccc3)cc2F)C(=O)CC1(C)c1ccncc1] | (6RS)-3-[2,6-Difluoro-4-(2-phenylethynyl)phenyl]-1,6-dimethyl-6-(4-pyridyl)hexahydropyrimidine-2,4-dione | 112 | 105 |
| 29 | 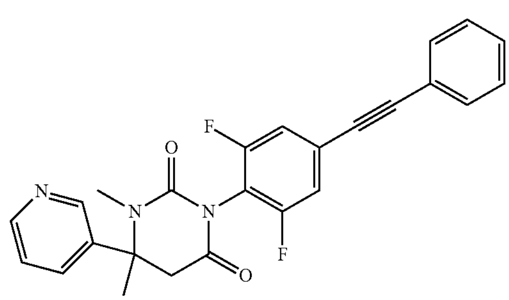 [SMILES: CN1C(=O)N(c2c(F)cc(C#Cc3ccccc3)cc2F)C(=O)CC1(C)c1cccnc1] | (6RS)-3-[2,6-Difluoro-4-(2-phenylethynyl)phenyl]-1,6-dimethyl-6-(3-pyridyl)hexahydropyrimidine-2,4-dione | 109 | 144 |

-continued

| | Structure | Name | EC$_{50}$ (nM) mGlu4 PAM | Eff. (%) |
|---|---|---|---|---|
| 30 | 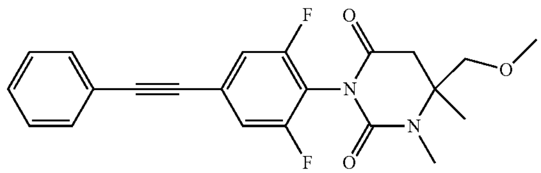 [SMILES: COCC1(C)CC(=O)N(c2c(F)cc(C#Cc3ccccc3)cc2F)C(=O)N1C] | (6RS)-3-[2,6-Difluoro-4-(2-phenylethynyl)phenyl]-6-(methoxymethyl)-1,6-dimethyl-hexahydropyrimidine-2,4-dione | 123 | 103 |
| 31 | 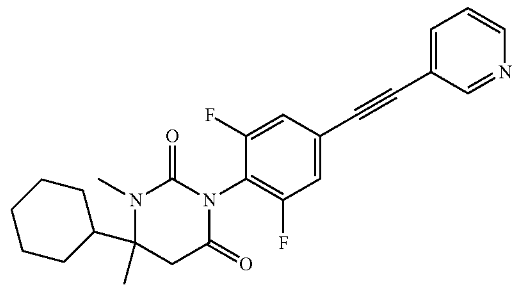 [SMILES: CN1C(=O)N(c2c(F)cc(C#Cc3cccnc3)cc2F)C(=O)CC1(C)C1CCCCC1] | (6RS)-6-Cyclohexyl-3-[2,6-difluoro-4-[2-(3-pyridyl)ethynyl]phenyl]-1,6-dimethyl-hexahydropyrimidine-2,4-dione | 245 | 117 |
| 32 | 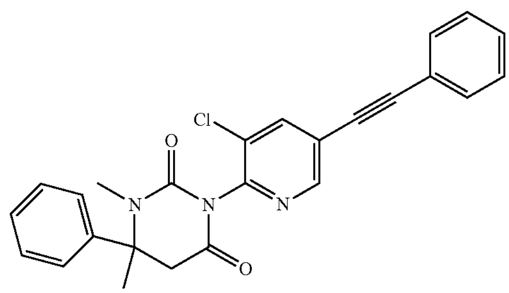 [SMILES: CN1C(=O)N(c2ncc(C#Cc3ccccc3)cc2Cl)C(=O)CC1(C)c1ccccc1] | (6RS)-3-[3-Chloro-5-(2-phenylethynyl)-2-pyridyl]-1,6-dimethyl-6-phenyl-hexahydropyrimidine-2,4-dione | 155 | 103 |
| 33 | 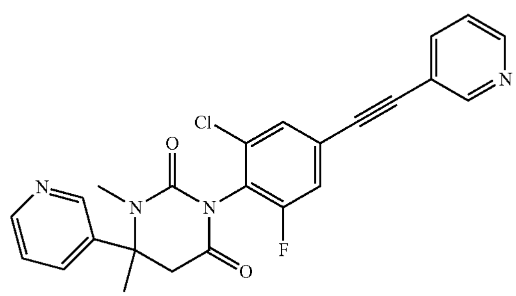 [SMILES: CN1C(=O)N(c2c(F)cc(C#Cc3cccnc3)cc2Cl)C(=O)CC1(C)c1cccnc1] | (6RS)-3-[2-Chloro-6-fluoro-4-[2-(3-pyridyl)ethynyl]phenyl]-1,6-dimethyl-6-(3-pyridyl)hexahydropyrimidine-2,4-dione | 171 | 142 |
| 34 | 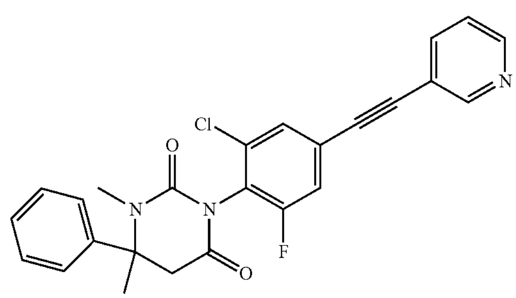 | (6RS)-3-[2-Chloro-6-fluoro-4-[2-(3-pyridyl)ethynyl]phenyl]-1,6-dimethyl-6-phenyl-hexahydropyrimidine-2,4-dione | 135 | 150 |
| 35 | 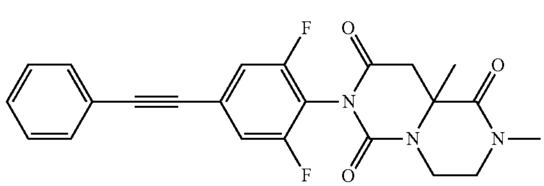 [SMILES: CN1CCN2C(=O)N(c3c(F)cc(C#Cc4ccccc4)cc3F)C(=O)CC2(C)C1=O] | (9aRS)-7-[2,6-Difluoro-4-(2-phenylethynyl)phenyl]-2,9a-dimethyl-4,9-dihydro-3H-pyrazino[1,2-c]pyrimidine-1,6,8-trione | 158 | 131 |

| | Structure | Name | EC$_{50}$ (nM) mGlu4 PAM | Eff. (%) |
|---|---|---|---|---|
| 36 | 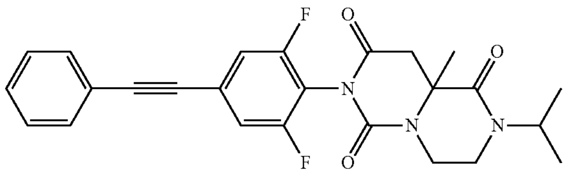 [SMILES: CC(C)N1CCN2C(=O)N(c3c(F)cc(C#Cc4ccccc4)cc3F)C(=O)CC2(C)C1=O] | (9aRS)-7-[2,6-Difluoro-4-(2-phenylethynyl)phenyl]-2-isopropyl-9a-methyl-4,9-dihydro-3H-pyrazino[1,2-c]pyrimidine-1,6,8-trione | 169 | 128 |
| 37 | 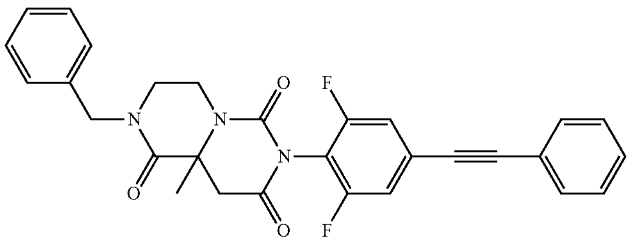 [SMILES: CC12CC(=O)N(c3c(F)cc(C#Cc4ccccc4)cc3F)C(=O)N1CCN(Cc1ccccc1)C2=O] | (9aRS)-2-Benzyl-7-[2,6-difluoro-4-(2-phenylethynyl)phenyl]-9a-methyl-4,9-dihydro-3H-pyrazino[1,2-c]pyrimidine-1,6,8-trione | 131 | 97 |
| 38 | 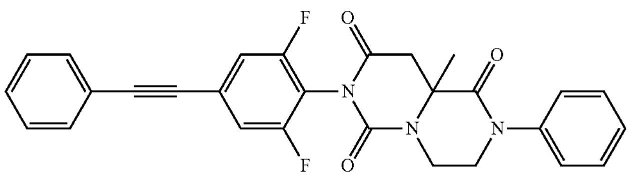 [SMILES: CC12CC(=O)N(c3c(F)cc(C#Cc4ccccc4)cc3F)C(=O)N1CCN(c1ccccc1)C2=O] | (9aRS)-7-[2,6-Difluoro-4-(2-phenylethynyl)phenyl]-9a-methyl-2-phenyl-4,9-dihydro-3H-pyrazino[1,2-c]pyrimidine-1,6,8-trione | 31 | 105 |
| 39 | 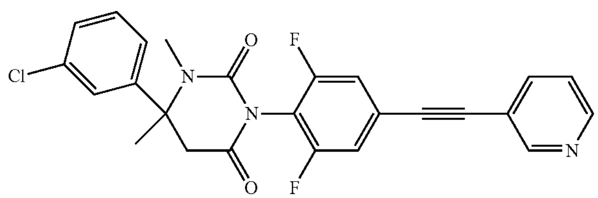 [SMILES: CN1C(=O)N(c2c(F)cc(C#Cc3cccnc3)cc2F)C(=O)CC1(C)c1cccc(Cl)c1] | (6RS)-6-(3-Chlorophenyl)-3-[2,6-difluoro-4-[2-(3-pyridyl)ethynyl]phenyl]-1,6-dimethyl-hexahydropyrimidine-2,4-dione | 224 | 112 |
| 40 | 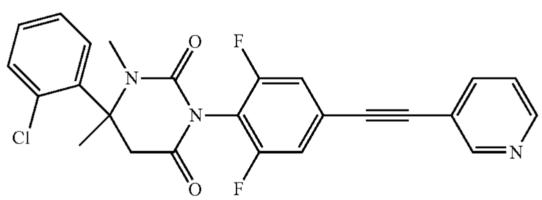 [SMILES: CN1C(=O)N(c2c(F)cc(C#Cc3cccnc3)cc2F)C(=O)CC1(C)c1ccccc1Cl] | (6RS)-6-(2-Chlorophenyl)-3-[2,6-difluoro-4-[2-(3-pyridyl)ethynyl]phenyl]-1,6-dimethyl-hexahydropyrimidine-2,4-dione | 394 | 109 |
| 41 | 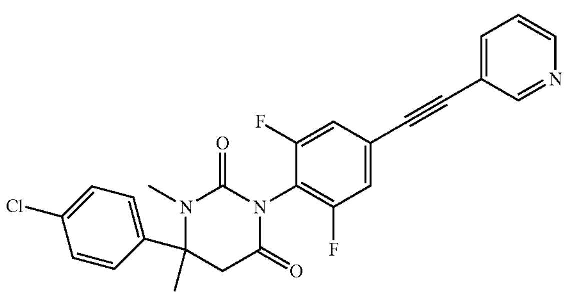 [SMILES: CN1C(=O)N(c2c(F)cc(C#Cc3cccnc3)cc2F)C(=O)CC1(C)c1ccc(Cl)cc1] | (6RS)-6-(4-Chlorophenyl)-3-[2,6-difluoro-4-[2-(3-pyridyl)ethynyl]phenyl]-1,6-dimethyl-hexahydropyrimidine-2,4-dione | 229 | 115 |
| 42 | 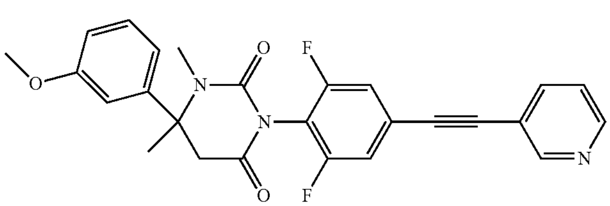 [SMILES: COc1cccc(C2(C)CC(=O)N(c3c(F)cc(C#Cc4cccnc4)cc3F)C(=O)N2C)c1] | (6RS)-3-[2,6-Difluoro-4-[2-(3-pyridyl)ethynyl]phenyl]-6-(3-methoxyphenyl)-1,6-dimethyl-hexahydropyrimidine-2,4-dione | 165 | 116 |

-continued

| | Structure | Name | EC$_{50}$ (nM) mGlu4 PAM | Eff. (%) |
|---|---|---|---|---|
| 43 | 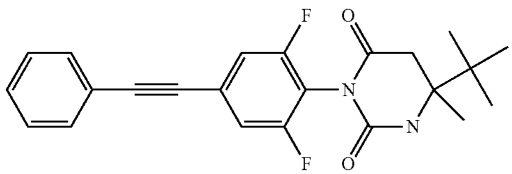 [SMILES: CC(C)(C)C1(C)CC(=O)N(c2c(F)cc(C#Cc3ccccc3)cc2F)C(=O)N1] | (6RS)-6-tert-Butyl-3-[2,6-difluoro-4-(2-phenylethynyl)phenyl]-6-methyl-hexahydropyrimidine-2,4-dione | 75 | 92 |
| 44 | 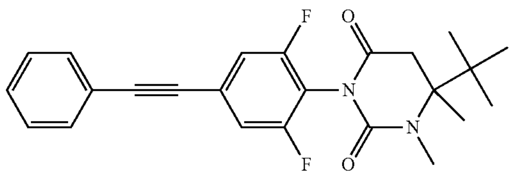 [SMILES: CN1C(=O)N(c2c(F)cc(C#Cc3ccccc3)cc2F)C(=O)CC1(C)C(C)(C)C] | (6RS)-6-tert-Butyl-3-[2,6-difluoro-4-(2-phenylethynyl)phenyl]-1,6-dimethyl-hexahydropyrimidine-2,4-dione | 66 | 109 |
| 45 | 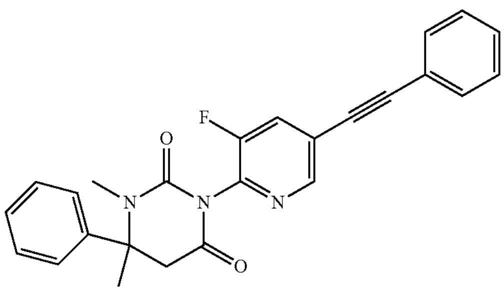 [SMILES: CN1C(=O)N(c2ncc(C#Cc3ccccc3)cc2F)C(=O)CC1(C)c1ccccc1] | (6RS)-3-[3-Fluoro-5-(2-phenylethynyl)-2-pyridyl]-1,6-dimethyl-6-phenyl-hexahydropyrimidine-2,4-dione | 72 | 107 |
| 46 | 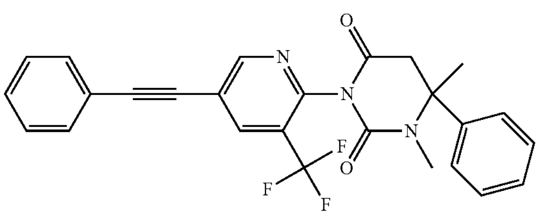 [SMILES: CN1C(=O)N(c2ncc(C#Cc3ccccc3)cc2C(F)(F)F)C(=O)CC1(C)c1ccccc1] | (6RS)-1,6-Dimethyl-6-phenyl-3-[5-(2-phenylethynyl)-3-(trifluoromethyl)-2-pyridyl]hexahydropyrimidine-2,4-dione | 116 | 105 |
| 47 | 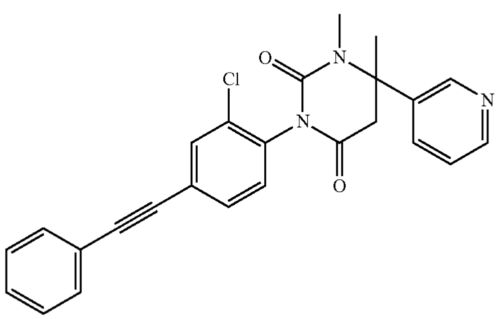 [SMILES: CN1C(=O)N(c2ccc(C#Cc3ccccc3)cc2Cl)C(=O)CC1(C)c1cccnc1] | (6RS)-3-[2-Chloro-4-(2-phenylethynyl)phenyl]-1,6-dimethyl-6-(3-pyridyl)hexahydropyrimidine-2,4-dione | 132 | 121 |
| 48 | 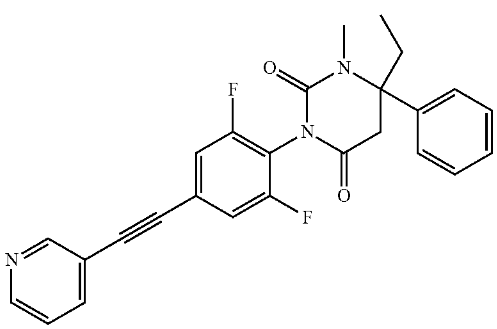 [SMILES: CCC1(c2ccccc2)CC(=O)N(c2c(F)cc(C#Cc3cccnc3)cc2F)C(=O)N1C] | (6RS)-3-[2,6-Difluoro-4-[2-(3-pyridyl)ethynyl]phenyl]-6-ethyl-1-methyl-6-phenyl-hexahydropyrimidine-2,4-dione | 88 | 108 |

-continued

| | Structure | Name | EC$_{50}$ (nM) mGlu4 PAM | Eff. (%) |
|---|---|---|---|---|
| 49 | 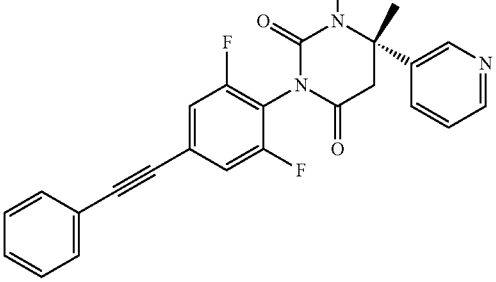 | (6S)-3-[2,6-Difluoro-4-(2-phenylethynyl)phenyl]-1,6-dimethyl-6-(3-pyridyl)hexahydropyrimidine-2,4-dione | 37 | 98 |
| 50 | 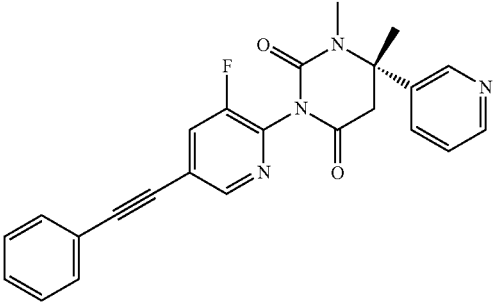 | (6S)-3-[3-Fluoro-5-(2-phenylethynyl)-2-pyridyl]-1,6-dimethyl-6-(3-pyridyl)hexahydropyrimidine-2,4-dione | 104 | 164 |
| 51 | 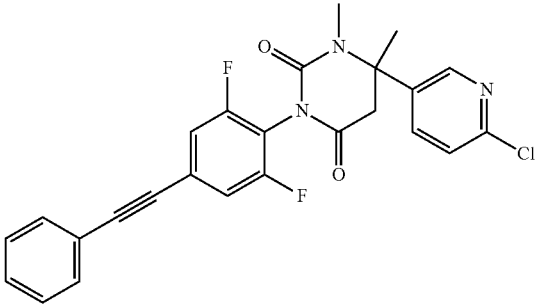 [SMILES: CN1C(=O)N(c2c(F)cc(C#Cc3ccccc3)cc2F)C(=O)CC1(C)c1ccc(Cl)nc1] | (6RS)-6-(6-Chloro-3-pyridyl)-3-[2,6-difluoro-4-(2-phenylethynyl)phenyl]-1,6-dimethyl-hexahydropyrimidine-2,4-dione | 88 | 108 |
| 52 | 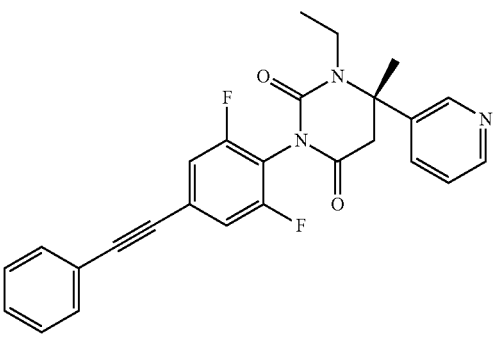 | (6S)-3-[2,6-Difluoro-4-(2-phenylethynyl)phenyl]-1-ethyl-6-methyl-6-(3-pyridyl)hexahydropyrimidine-2,4-dione | 48 | 99 |

-continued

| | Structure | Name | EC$_{50}$ (nM) mGlu4 PAM | Eff. (%) |
|---|---|---|---|---|
| 53 | 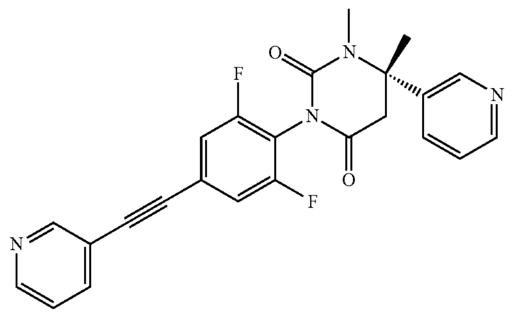 [SMILES: CN1C(=O)N(c2c(F)cc(C#Cc3cccnc3)cc2F)C(=O)C[C@@]1(C)c1cccnc1] | (6S)-3-[2,6-Difluoro-4-[2-(3-pyridyl)ethynyl]phenyl]-1,6-dimethyl-6-(3-pyridyl)hexahydropyrimidine-2,4-dione | 80 | 110 |
| 54 | 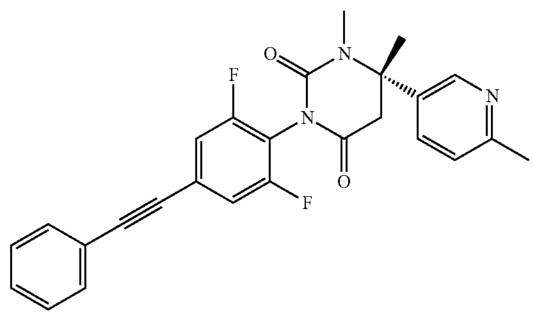 [SMILES: Cc1ccc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-1,6-dimethyl-6-(6-methyl-3-pyridyl)hexahydropyrimidine-2,4-dione | 70 | 98 |
| 55 | 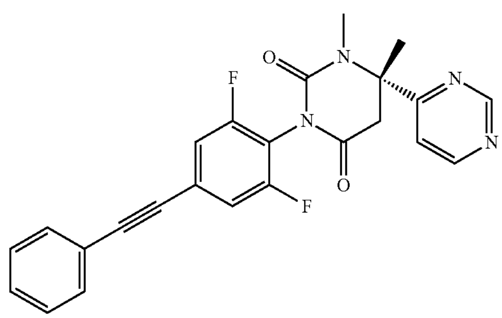 [SMILES: CN1C(=O)N(c2c(F)cc(C#Cc3ccccc3)cc2F)C(=O)C[C@@]1(C)c1ccncn1] | (6S)-3-[2,6-Difluoro-4-(2-phenylethynyl)phenyl]-1,6-dimethyl-6-pyrimidin-4-yl-hexahydropyrimidine-2,4-dione | 44 | 106 |
| 56 | 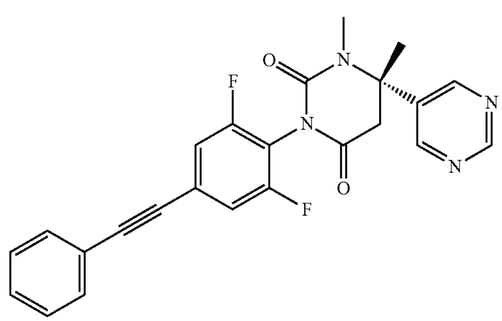 [SMILES: CN1C(=O)N(c2c(F)cc(C#Cc3ccccc3)cc2F)C(=O)C[C@@]1(C)c1cncnc1] | (6S)-3-[2,6-Difluoro-4-(2-phenylethynyl)phenyl]-1,6-dimethyl-6-pyrimidin-5-yl-hexahydropyrimidine-2,4-dione | 79 | 99 |
| 57 | 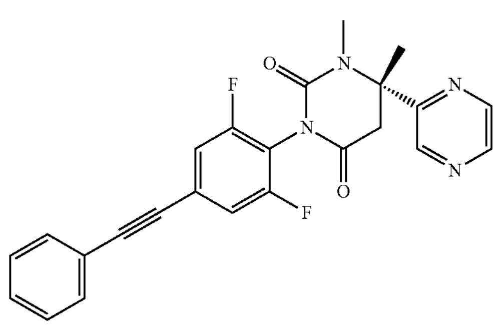 [SMILES: CN1C(=O)N(c2c(F)cc(C#Cc3ccccc3)cc2F)C(=O)C[C@@]1(C)c1cnccn1] | (6S)-3-[2,6-Difluoro-4-(2-phenylethynyl)phenyl]-1,6-dimethyl-6-pyrazin-2-yl-hexahydropyrimidine-2,4-dione | 117 | 102 |

-continued

| | Structure | Name | EC$_{50}$ (nM) mGlu4 PAM | Eff. (%) |
|---|---|---|---|---|
| 58 | 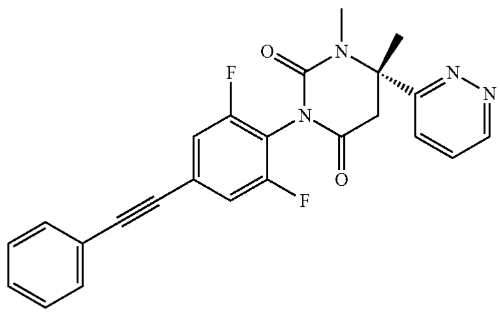 [SMILES: CN1C(=O)N(c2c(F)cc(C#Cc3ccccc3)cc2F)C(=O)C[C@@]1(C)c1cccnn1] | (6S)-3-[2,6-Difluoro-4-(2-phenylethynyl)phenyl]-1,6-dimethyl-6-pyridazin-3-yl-hexahydropyrimidine-2,4-dione | 49 | 99 |
| 59 | 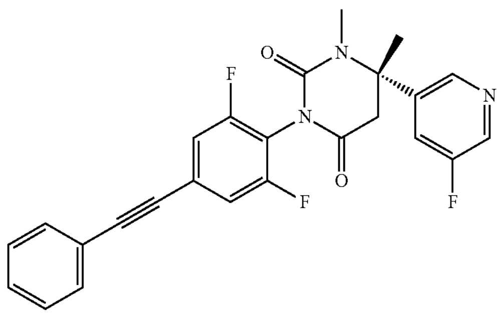 [SMILES: CN1C(=O)N(c2c(F)cc(C#Cc3ccccc3)cc2F)C(=O)C[C@@]1(C)c1cncc(F)c1] | (6S)-3-[2,6-Difluoro-4-(2-phenylethynyl)phenyl]-6-(5-fluoro-3-pyridyl)-1,6-dimethyl-hexahydropyrimidine-2,4-dione | 75 | 89 |
| 60 | 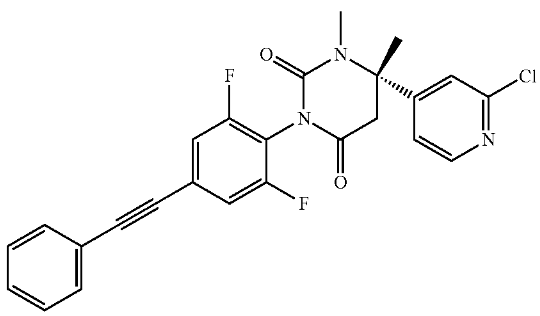 [SMILES: CN1C(=O)N(c2c(F)cc(C#Cc3ccccc3)cc2F)C(=O)C[C@@]1(C)c1ccnc(Cl)c1] | (6S)-6-(2-Chloro-4-pyridyl)-3-[2,6-difluoro-4-(2-phenylethynyl)phenyl]-1,6-dimethyl-hexahydropyrimidine-2,4-dione | 38 | 113 |
| 61 | 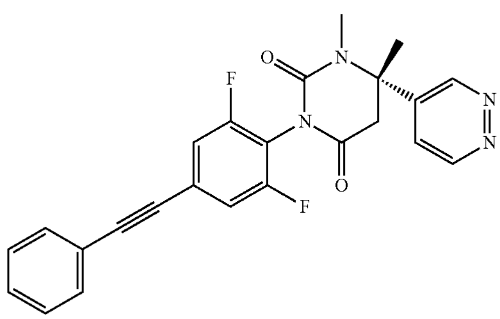 [SMILES: CN1C(=O)N(c2c(F)cc(C#Cc3ccccc3)cc2F)C(=O)C[C@@]1(C)c1ccnnc1] | (6S)-3-[2,6-Difluoro-4-(2-phenylethynyl)phenyl]-1,6-dimethyl-6-pyridazin-4-yl-hexahydropyrimidine-2,4-dione | 84 | 136 |
| 62 | 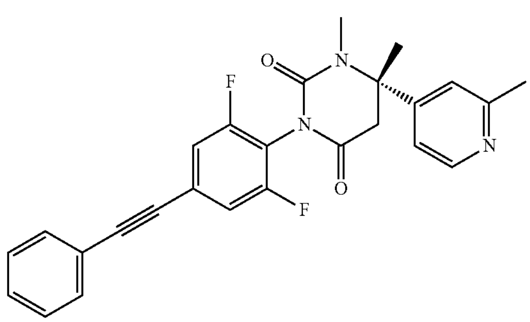 [SMILES: Cc1cc([C@]2(C)CC(=O)N(c3c(F)cc(C#Cc4ccccc4)cc3F)C(=O)N2C)ccn1] | (6S)-3-[2,6-Difluoro-4-(2-phenylethynyl)phenyl]-1,6-dimethyl-6-(2-methyl-4-pyridyl)hexahydropyrimidine-2,4-dione | 56 | 102 |

-continued

| | Structure | Name | EC$_{50}$ (nM) mGlu4 PAM | Eff. (%) |
|---|---|---|---|---|
| 63 | 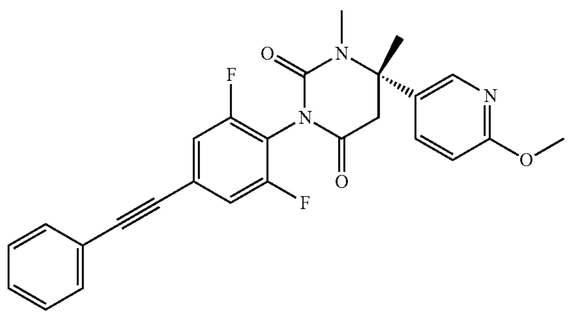 [SMILES: COc1ccc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-(6-methoxy-3-pyridyl)-1,6-dimethyl-hexahydropyrimidine-2,4-dione | 42 | 109 |
| 64 | 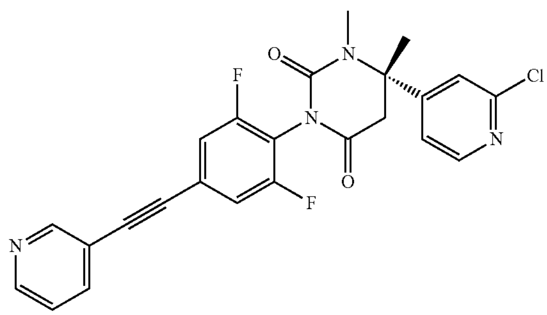 [SMILES: CN1C(=O)N(c2c(F)cc(C#Cc3cccnc3)cc2F)C(=O)C[C@@]1(C)c1ccnc(Cl)c1] | (6S)-6-(2-Chloro-4-pyridyl)-3-[2,6-difluoro-4-[2-(3-pyridyl)ethynyl]phenyl]-1,6-dimethyl-hexahydropyrimidine-2,4-dione | 124 | 119 |
| 65 | 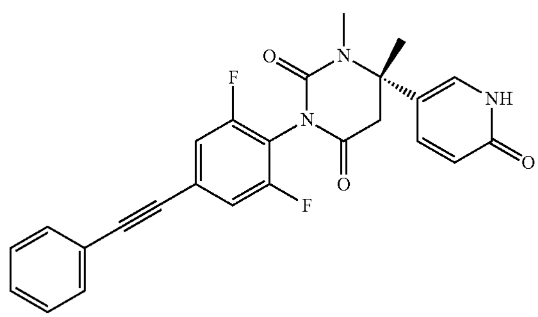 [SMILES: CN1C(=O)N(c2c(F)cc(C#Cc3ccccc3)cc2F)C(=O)C[C@@]1(C)c1ccc(=O)[nH]c1] | (6S)-3-[2,6-Difluoro-4-(2-phenylethynyl)phenyl]-1,6-dimethyl-6-(6-oxo-1H-pyridin-3-yl)hexahydropyrimidine-2,4-dione | 36 | 123 |
| 66 | 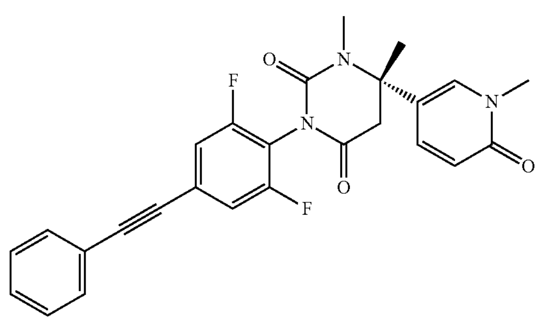 [SMILES: CN1C(=O)N(c2c(F)cc(C#Cc3ccccc3)cc2F)C(=O)C[C@@]1(C)c1ccc(=O)n(C)c1] | (6S)-3-[2,6-Difluoro-4-(2-phenylethynyl)phenyl]-1,6-dimethyl-6-(1-methyl-6-oxo-3-pyridyl)hexahydropyrimidine-2,4-dione | 43 | 114 |
| 67 | 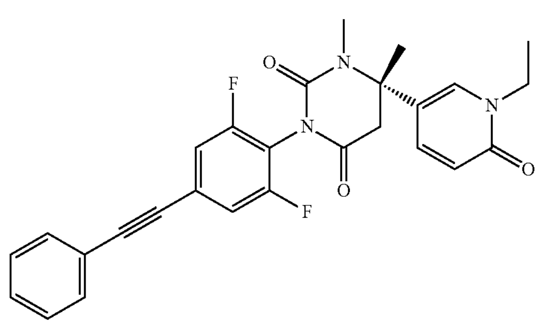 [SMILES: CCn1cc([C@]2(C)CC(=O)N(c3c(F)cc(C#Cc4ccccc4)cc3F)C(=O)N2C)ccc1=O] | (6S)-3-[2,6-Difluoro-4-(2-phenylethynyl)phenyl]-6-(1-ethyl-6-oxo-3-pyridyl)-1,6-dimethyl-hexahydropyrimidine-2,4-dione | 56 | 106 |

| | Structure | Name | EC$_{50}$ (nM) mGlu4 PAM | Eff. (%) |
|---|---|---|---|---|
| 68 | 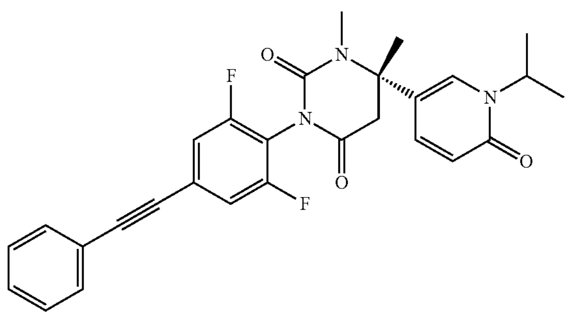 [SMILES: CC(C)n1cc([C@]2(C)CC(=O)N(c3c(F)cc(C#Cc4ccccc4)cc3F)C(=O)N2C)ccc1=O] | (6S)-3-[2,6-Difluoro-4-(2-phenylethynyl)phenyl]-6-(1-isopropyl-6-oxo-3-pyridyl)-1,6-dimethyl-hexahydropyrimidine-2,4-dione | 44 | 113 |
| 69 | 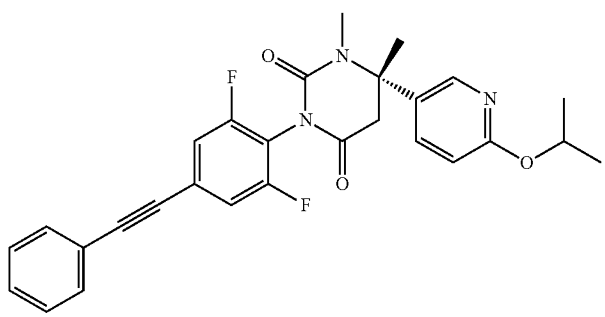 [SMILES: CC(C)Oc1ccc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-(6-isopropoxy-3-pyridyl)-1,6-dimethyl-hexahydropyrimidine-2,4-dione | 97 | 95 |
| 70 | 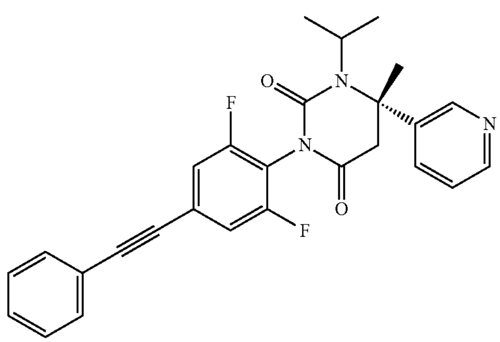 [SMILES: CC(C)N1C(=O)N(c2c(F)cc(C#Cc3ccccc3)cc2F)C(=O)C[C@@]1(C)c1cccnc1] | (6S)-3-[2,6-Difluoro-4-(2-phenylethynyl)phenyl]-1-isopropyl-6-methyl-6-(3-pyridyl)hexahydropyrimidine-2,4-dione | 73 | 106 |
| 71 | 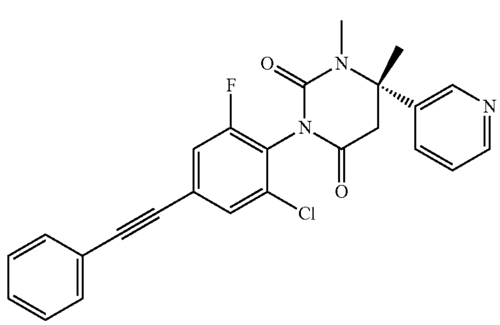 | (6S)-3-[2-Chloro-6-fluoro-4-(2-phenylethynyl)phenyl]-1,6-dimethyl-6-(3-pyridyl)hexahydropyrimidine-2,4-dione | 148 | 105 |

-continued

| | Structure | Name | EC$_{50}$ (nM) mGlu4 PAM | Eff. (%) |
|---|---|---|---|---|
| 72 | 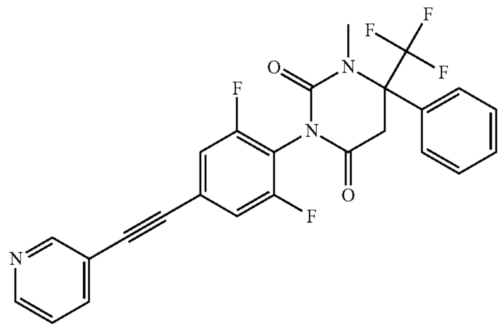 [SMILES: CN1C(=O)N(c2c(F)cc(C#Cc3cccnc3)cc2F)C(=O)CC1(c1ccccc1)C(F)(F)F] | (6RS)-3-[2,6-Difluoro-4-[2-(3-pyridyl)ethynyl]phenyl]-1-methyl-6-phenyl-6-(trifluoromethyl)hexahydropyrimidine-2,4-dione | 82 | 91 |
| 73 | 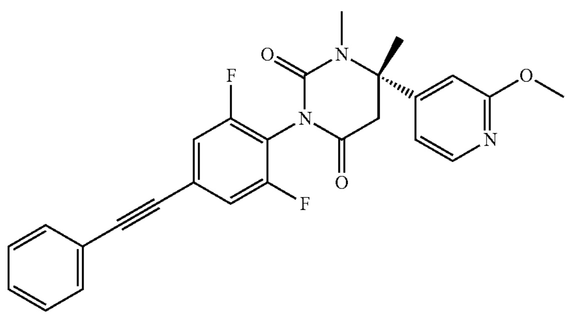 [SMILES: COc1cc([C@]2(C)CC(=O)N(c3c(F)cc(C#Cc4ccccc4)cc3F)C(=O)N2C)ccn1] | (6S)-3-[2,6-Difluoro-4-(2-phenylethynyl)phenyl]-6-(2-methoxy-4-pyridyl)-1,6-dimethyl-hexahydropyrimidine-2,4-dione | 47 | 120 |
| 74 | 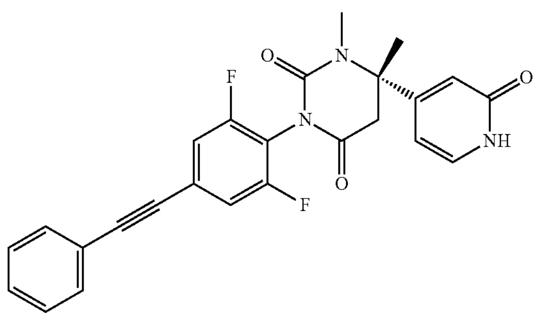 [SMILES: CN1C(=O)N(c2c(F)cc(C#Cc3ccccc3)cc2F)C(=O)C[C@@]1(C)c1cc[nH]c(=O)c1] | (6S)-3-[2,6-Difluoro-4-(2-phenylethynyl)phenyl]-1,6-dimethyl-6-(2-oxo-1H-pyridin-4-yl)hexahydropyrimidine-2,4-dione | 42 | 116 |
| 75 | 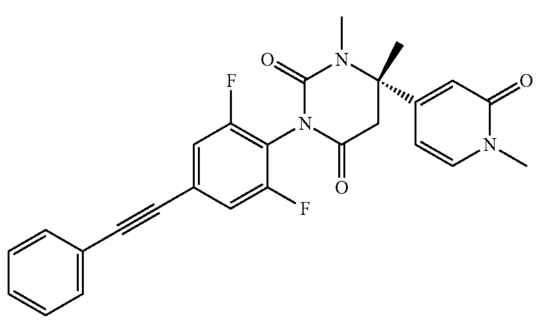 [SMILES: CN1C(=O)N(c2c(F)cc(C#Cc3ccccc3)cc2F)C(=O)C[C@@]1(C)c1ccn(C)c(=O)c1] | (6S)-3-[2,6-Difluoro-4-(2-phenylethynyl)phenyl]-1,6-dimethyl-6-(1-methyl-2-oxo-4-pyridyl)hexahydropyrimidine-2,4-dione | 55 | 108 |
| 76 | 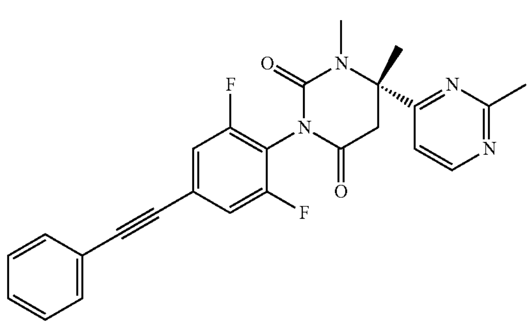 [SMILES: Cc1nccc([C@]2(C)CC(=O)N(c3c(F)cc(C#Cc4ccccc4)cc3F)C(=O)N2C)n1] | (6S)-3-[2,6-Difluoro-4-(2-phenylethynyl)phenyl]-1,6-dimethyl-6-(2-methylpyrimidin-4-yl)hexahydropyrimidine-2,4-dione | 103 | 111 |

-continued

| | Structure | Name | EC₅₀ (nM) mGlu4 PAM | Eff. (%) |
|---|---|---|---|---|
| 77 | 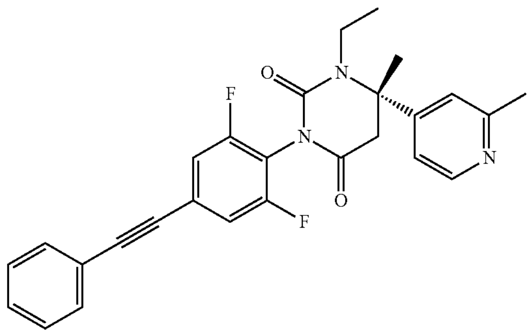 [SMILES: CCN1C(=O)N(c2c(F)cc(C#Cc3ccccc3)cc2F)C(=O)C[C@@]1(C)c1ccnc(C)c1] | (6S)-3-[2,6-Difluoro-4-(2-phenylethynyl)phenyl]-1-ethyl-6-methyl-6-(2-methyl-4-pyridyl) hexahydropyrimidine-2,4-dione | 68 | 111 |
| 78 | 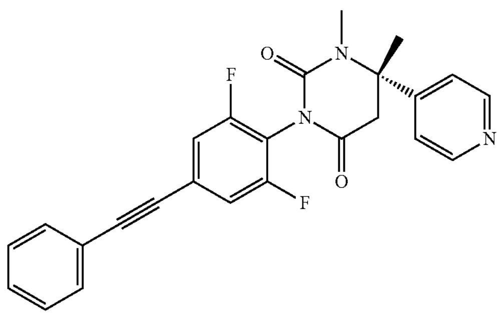 [SMILES: CN1C(=O)N(c2c(F)cc(C#Cc3ccccc3)cc2F)C(=O)C[C@@]1(C)c1ccncc1] | (6S)-3-[2,6-Difluoro-4-(2-phenylethynyl)phenyl]-1,6-dimethyl-6-(4-pyridyl) hexahydropyrimidine-2,4-dione | 68 | 111 |
| 79 | 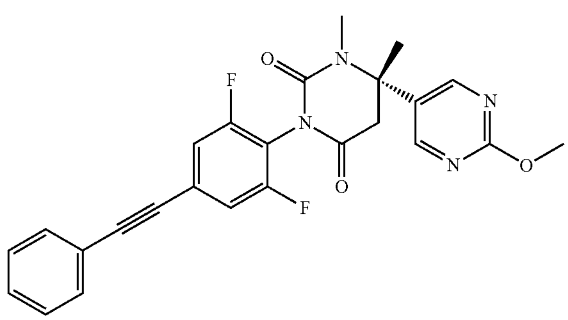 [SMILES: COc1ncc([C@]2(C)CC(=O)N(c3c(F)cc(C#Cc4ccccc4)cc3F)C(=O)N2C)cn1] | (6S)-3-[2,6-Difluoro-4-(2-phenylethynyl)phenyl]-6-(2-methoxypyrimidin-5-yl)-1,6-dimethyl-hexahydropyrimidine-2,4-dione | 46 | 105 |
| 80 | 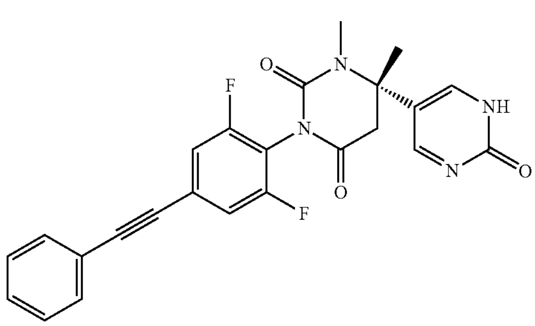 [SMILES: CN1C(=O)N(c2c(F)cc(C#Cc3ccccc3)cc2F)C(=O)C[C@@]1(C)c1cnc(=O)[nH]c1] | (6S)-3-[2,6-Difluoro-4-(2-phenylethynyl)phenyl]-1,6-dimethyl-6-(2-oxo-1H-pyrimidin-5-yl) hexahydropyrimidine-2,4-dione | 185 | 105 |

-continued

| | Structure | Name | EC$_{50}$ (nM) mGlu4 PAM | Eff. (%) |
|---|---|---|---|---|
| 81 | 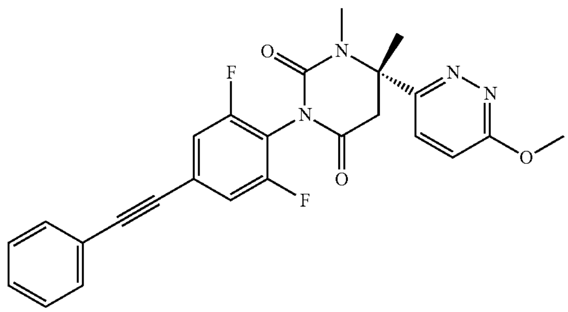 [SMILES: COc1ccc([C@]2(C)CC(=O)N(c3c(F)cc(C#Cc4ccccc4)cc3F)C(=O)N2C)nn1] | (6S)-3-[2,6-Difluoro-4-(2-phenylethynyl)phenyl]-6-(6-methoxypyridazin-3-yl)-1,6-dimethyl-hexahydropyrimidine-2,4-dione | 28 | 100 |
| 82 | 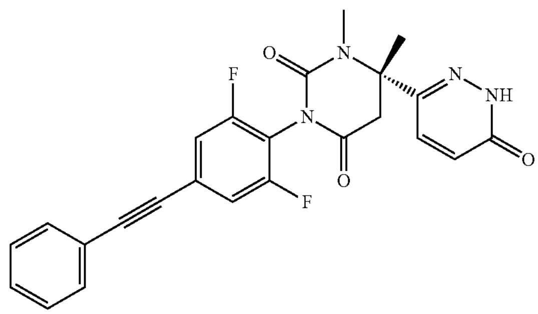 [SMILES: CN1C(=O)N(c2c(F)cc(C#Cc3ccccc3)cc2F)C(=O)C[C@@]1(C)c1ccc(=O)[nH]n1] | (6S)-3-[2,6-Difluoro-4-(2-phenylethynyl)phenyl]-1,6-dimethyl-6-(6-oxo-1H-pyridazin-3-yl)hexahydropyrimidine-2,4-dione | 18 | 115 |
| 83 | 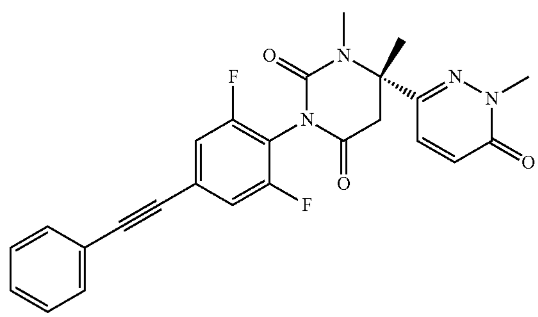 [SMILES: CN1C(=O)N(c2c(F)cc(C#Cc3ccccc3)cc2F)C(=O)C[C@@]1(C)c1ccc(=O)n(C)n1] | (6S)-3-[2,6-Difluoro-4-(2-phenylethynyl)phenyl]-1,6-dimethyl-6-(1-methyl-6-oxo-pyridazin-3-yl)hexahydropyrimidine-2,4-dione | 42 | 116 |
| 84 | 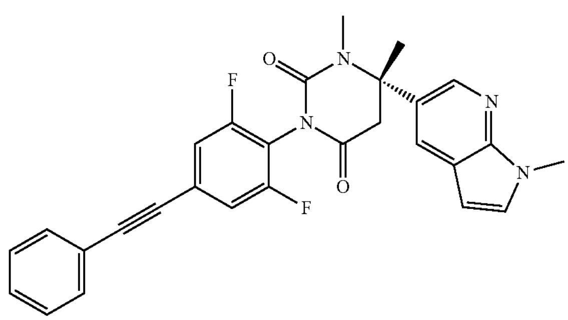 [SMILES: CN1C(=O)N(c2c(F)cc(C#Cc3ccccc3)cc2F)C(=O)C[C@@]1(C)c1cnc2c(ccn2C)c1] | (6S)-3-[2,6-Difluoro-4-(2-phenylethynyl)phenyl]-1,6-dimethyl-6-(1-methylpyrrolo[2,3-b]pyridin-5-yl)hexahydropyrimidine-2,4-dione | 40 | 114 |
| 85 | 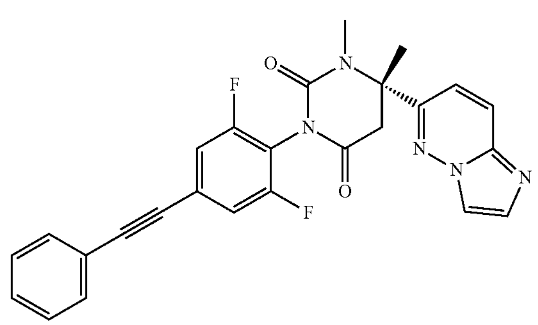 [SMILES: CN1C(=O)N(c2c(F)cc(C#Cc3ccccc3)cc2F)C(=O)C[C@@]1(C)c1ccc2nccn2n1] | (6S)-3-[2,6-Difluoro-4-(2-phenylethynyl)phenyl]-6-imidazo[1,2-b]pyridazin-6-yl-1,6-dimethyl-hexahydropyrimidine-2,4-dione | 57 | 88 |

-continued

| | Structure | Name | EC$_{50}$ (nM) mGlu4 PAM | Eff. (%) |
|---|---|---|---|---|
| 86 | 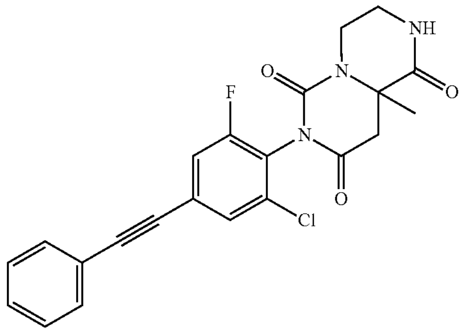 [SMILES: CC12CC(=O)N(c3c(F)cc(C#Cc4ccccc4)cc3Cl)C(=O)N1CCNC2=O] | (9aRS)-7-[2-Chloro-6-fluoro-4-(2-phenylethynyl)phenyl]-9a-methyl-2,3,4,9-tetrahydropyrazino[1,2-c]pyrimidine-1,6,8-trione | 108 | 100 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, drages, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, drages and hard gelatin capsules. Suitable carriers for soft gelatin capsules are, for example, vegetable oils, waxes, fats, semi-solid and liquid polyols and the like; depending on the nature of the active substance no carriers are, however, usually required in the case of soft gelatin capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Preparation of Pharmaceutical Compositions Comprising Compounds of the Invention Tablets of the following composition are manufactured in the usual manner:

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the following composition are manufactured:

| | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.

2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection solutions of the following composition are manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

A compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Experimental Section:

Example 1

3-[2,6-Difluoro-4-(2-phenylethynyl)phenyl]-1,6,6-trimethyl-hexahydropyrimidine-2,4-dione

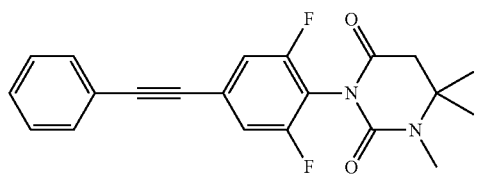 [SMILES: CN1C(=O)N(c2c(F)cc(C#Cc3ccccc3)cc2F)C(=O)CC1(C)C]

Step 1: 2,6-Difluoro-4-phenylethynyl-phenylamine

Bis-(triphenylphosphine)-palladium(II)dichloride (826 mg, 1.18 mmol, 0.02 equiv.) was dissolved in 100 ml THF. 2,6-Difluoro-4-iodoaniline (15 g, 58.8 mmol) and phenylacetylene (7.2 g, 7.8 ml, 70.6 mmol, 1.2 equiv.) were added at room temperature. Triethylamine (29.8 g, 41 ml, 0.29 mol, 5 equiv.), triphenylphosphine (617 mg, 2.35 mmol, 0.04 equiv.) and copper(I)iodide (112 mg, 0.58 mmol, 0.01 equiv.) were added and the mixture was stirred for 1 hour at 60° C. The reaction mixture was cooled and extracted with saturated NaHCO₃ solution and two times with ethyl acetate. The organic layers were washed three times with water, dried over sodium sulfate and evaporated to dryness. The crude product was purified by flash chromatography on a silica gel column eluting with an ethyl acetate:heptane 0:100 to 40:60 gradient. The desired 2,6-difluoro-4-phenylethynyl-phenylamine (12.6 g, 93% yield) was obtained as a yellow solid, MS: m/e=230.1 (M+H⁺).

Step 2: Methyl 3-[[2,6-difluoro-4-(2-phenylethynyl)phenyl]carbamoylamino]-3-methyl-butanoate 2,6-Difluoro-4-phenylethynyl-phenylamine (Example 1, step 1) (150 mg, 0.65 mmol) was dissolved in toluene (3.0 ml) and CDI (117 mg, 0.72 mmol, 1.1 equiv.) was added at room temperature. The mixture was stirred for 1 hour at 110° C. To the mixture methyl 3-amino-3-methylbutanoate (86 mg, 0.65 mmol, 1.0 equiv.) was added and stirred for 1 hour at 110° C. The reaction mixture was cooled and loaded directly onto a silica gel column. The crude product was purified by flash chromatography eluting with an ethyl acetate:heptane 0:100 to 60:40 gradient. The desired methyl 3-[[2,6-difluoro-4-(2-phenylethynyl)phenyl]carbamoylamino]-3-methyl-butanoate (248 mg, 98% yield) was obtained as a light yellow solid, MS: m/e=387.3 (M+H⁺).

Step 3: 3-[2,6-Difluoro-4-(2-phenylethynyl)phenyl]-6,6-dimethyl-hexahydropyrimidine-2,4-dione (248 mg, 0.64 mmol) Methyl 3-[[2,6-difluoro-4-(2-phenylethynyl)phenyl]carbamoylamino]-3-methyl-butanoate (Example 1, step 2) was dissolved in THF (3 ml) and sodium hydride (60% in mineral oil) (31 mg, 0.77 mmol, 1.2 equiv.) was added at room temperature. The mixture was stirred for 1 hour at room temperature. The reaction mixture was extracted with saturated NaHCO₃ solution and two times with ethyl acetate. The organic layers were washed with water and brine, dried over sodium sulfate and evaporated to dryness. The crude product was purified by flash chromatography on a silica gel column eluting with an ethyl acetate:heptane 0:100 to 100:0 gradient. The desired 3-[2,6-difluoro-4-(2-phenylethynyl)phenyl]-6,6-dimethyl-hexahydropyrimidine-2,4-dione (90 mg, 40% yield) was obtained as a light yellow solid, MS: m/e=355.2 (M+H⁺).

Step 4: 3-[2,6-Difluoro-4-(2-phenylethynyl)phenyl]-1,6,6-trimethyl-hexahydropyrimidine-2,4-dione (45 mg, 0.127 mmol) 3-[2,6-difluoro-4-(2-phenylethynyl)phenyl]-6,6-dimethyl-hexahydropyrimidine-2,4-dione (Example 1, step 3) was dissolved in DMF (1 ml) and cesium carbonate (83 mg, 0.25 mmol, 2 equiv.) and iodomethane (27 mg, 12 μl 0.19 mmol, 1.5 equiv.) were added at room temperature. The mixture was stirred for 1 hour at room temperature. The reaction mixture was evaporated with isolute®. The crude product was purified by flash chromatography on a silica gel column eluting with an ethyl acetate:heptane 0:100 to 60:40 gradient. The desired 3-[2,6-difluoro-4-(2-phenylethynyl)phenyl]-1,6,6-trimethyl-hexahydropyrimidine-2,4-dione (28 mg, 60% yield) was obtained as a white solid, MS: m/e=369.2 (M+H⁺).

Example 2

3-[2-Chloro-4-(2-phenylethynyl)phenyl]1,6,6-trimethyl-hexahydropyrimidine-2,4-dione

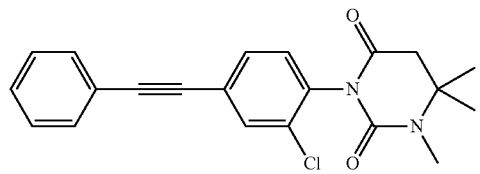

Step 1: 2-Chloro-4-(2-phenylethynyl)aniline

The title compound was obtained as a yellow solid, MS: m/e=228.1/230.1 (M+H$^+$), using chemistry similar to that described in Example 1, step 1 from 2-chloro-4-iodoaniline and phenylacetylene.

Step 2: 3-[2-Chloro-4-(2-phenylethynyl)phenyl]-6,6-dimethyl-hexahydropyrimidine-2,4-dione The title compound was obtained as a white solid, MS: m/e=353.1/355.1 (M+H$^+$), using chemistry similar to that described in Example 1, step 2 starting from 2-chloro-4-(2-phenylethynyl)aniline (Example 2, step 1) and methyl 3-amino-3-methylbutanoate.

Step 3: 3-[2-Chloro-4-(2-phenylethynyl)phenyl]-1,6,6-trimethyl-hexahydropyrimidine-2,4-dione The title compound was obtained as a white solid, MS: m/e=367.2/369.2 (M+H$^+$), using chemistry similar to that described in Example 1, step 4 by using K$_2$CO$_3$ instead of Cs$_2$CO$_3$ starting from 3-[2-chloro-4-(2-phenylethynyl)phenyl]-6,6-dimethyl-hexahydropyrimidine-2,4-dione (Example 2, step 2) and iodomethane.

Example 3

3-[2-Chloro-4-(2-phenylethynyl)phenyl]-1-methyl-1,3-diazaspiro[5.5]undecane-2,4-dione

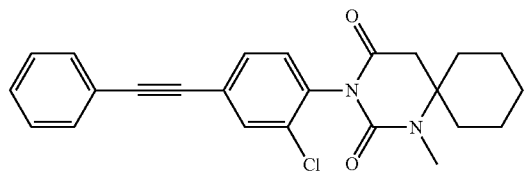

Step 1: Methyl 2-[1-[[2-chloro-4-(2-phenylethynyl)phenyl]carbamoylamino]cyclohexyl]acetate The title compound was obtained as a light brown solid, MS: m/e=425.3/427.3 (M+H$^+$), using chemistry similar to that described in Example 5, step 1 starting from 2-chloro-4-(2-phenylethynyl)aniline (Example 2, step 1) and methyl 2-(1-aminocyclohexyl)acetate hydrochloride.

Step 2: 3-[2-Chloro-4-(2-phenylethynyl)phenyl]-1,3-diazaspiro[5.5]undecane-2,4-dione The title compound was obtained as a light brown oil, MS: m/e=393.2 (M+H$^+$), using chemistry similar to that described in Example 1, step 3 by using KOtBu instead of NaH starting from methyl 2-[1-[[2-chloro-4-(2-phenylethynyl)phenyl]carbamoylamino]cyclohexyl]acetate (Example 3, step 1).

Step 3: 3-[2-Chloro-4-(2-phenylethynyl)phenyl]-1-methyl-1,3-diazaspiro[5.5]undecane-2,4-dione The title compound was obtained as a brown oil, MS: m/e=407.3/409.2 (M+H$^+$), using chemistry similar to that described in Example 1, step 4 by using K$_2$CO$_3$ instead of Cs$_2$CO$_3$ starting from 3-[2-chloro-4-(2-phenylethynyl)phenyl]-1,3-diazaspiro[5.5]undecane-2,4-dione (Example 3, step 2) and iodomethane.

Example 4

3-[2-Chloro-4-(2-phenylethynyl)phenyl]-1-methyl-9-oxa-1,3-diazaspiro[5.5]undecane-2,4-dione

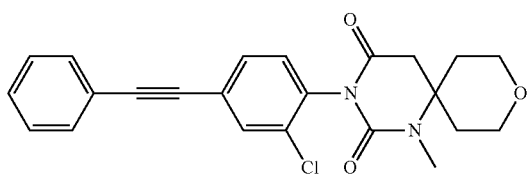

Step 1: Methyl 2-[4-[[2-chloro-4-(2-phenylethynyl)phenyl]carbamoylamino]tetrahydropyran-4-yl]acetate The title compound was obtained as a light brown solid, MS: m/e=427.3/429.3 (M+H$^+$), using chemistry similar to that described in Example 5, step 1 starting from 2-chloro-4-(2-phenylethynyl)aniline (Example 2, step 1) and ethyl 2-(4-aminotetrahydro-2H-pyran-4-yl)acetate hydrochloride.

Step 2: 3-[2-Chloro-4-(2-phenylethynyl)phenyl]-9-oxa-1,3-diazaspiro[5.5]undecane-2,4-dione The title compound was obtained as a light brown solid, MS: m/e=395.2/397.2 (M+H$^+$), using chemistry similar to that described in Example 1, step 3 by using KOtBu instead of NaH starting from methyl 2-[4-[[2-chloro-4-(2-phenylethynyl)phenyl]carbamoylamino]tetrahydropyran-4-yl]acetate (Example 4, step 1).

Step 3: 3-[2-Chloro-4-(2-phenylethynyl)phenyl]-1-methyl-9-oxa-1,3-diazaspiro[5.5]undecane-2 4-dione The title compound was obtained as a yellow oil, MS: m/e=409.2/411.3 (M+H$^+$), using chemistry similar to that described in Example 1, step 4 by using NaH instead of Cs$_2$CO$_3$ starting from 3-[2-chloro-4-(2-phenylethynyl)phenyl]-9-oxa-1,3-diazaspiro[5.5]undecane-2,4-dione (Example 4, step 2) and iodomethane.

Example 5

7-[2-Chloro-4-(2-phenylethynyl)phenyl]-5-methyl-5,7-diazaspiro[3.5]nonane-6,8-dione

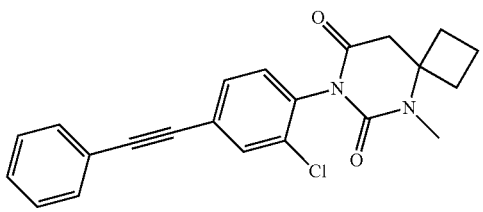 [SMILES: CN1C(=O)N(c2ccc(C#Cc3ccccc3)cc2Cl)C(=O)CC12CCC2]

Step 1: Methyl 2-[1-[[2-chloro-4-(2-phenylethynyl)phenyl]carbamoylamino]cyclobutyl]acetate 2-Chloro-4-(2-phenylethynyl)aniline (Example 2, step 1) (300 mg, 1.32 mmol) was dissolved in toluene (5.0 ml) and bis(trichloromethyl) carbonate (156 mg, 0.53 mmol, 0.4 equiv.) was added at room temperature. The mixture was stirred for 1 hour at 110° C. To the mixture Et$_3$N (667 mg, 0.91 ml, 6.59 mmol, 5 equiv.) and methyl 2-(1-aminocyclobutyl)acetate (171 mg, 0.94 mmol, 1.2 equiv.) were added and stirred for 16 hours at room temperature. The reaction mixture was loaded directly onto a silica gel column. The crude product was purified by flash chromatography eluting with an ethyl acetate:heptane 0:100 to 100:0 gradient. The desired methyl 2-[1-[[2-chloro-4-(2-phenylethynyl)phenyl]carbamoylamino]cyclobutyl]acetate (385 mg, 74% yield) was obtained as a yellow solid, MS: m/e=397.3/399.3 (M+H$^+$).

Step 2: 7-[2-Chloro-4-(2-phenylethynyl)phenyl]-5,7-diazaspiro[3.5]nonane-6,8-dione Treatment of methyl 2-[1-[[2-chloro-4-(2-phenylethynyl)phenyl]carbamoylamino]cyclobutyl]-acetate (Example 5, step 1) using chemistry similar to that described in Example 1, step 3 by using KOtBu instead of NaH formed the corresponding acid which was transformed by treatment with SOCl$_2$ into the corresponding acid chloride which cyclises to form the title compound which was obtained as a yellow solid, MS: m/e=365.2/367.3 (M+H$^+$).

Step 3: 7-[2-Chloro-4-(2-phenylethynyl)phenyl]-5-methyl-5,7-diazaspiro[3.5]nonane-6,8-dione The title compound was obtained as a white solid, MS: m/e=379.2/381.1 (M+H$^+$), using chemistry similar to that described in Example 1, step 4 by using NaH instead of Cs$_2$CO$_3$ starting from 7-[2-chloro-4-(2-phenylethynyl)phenyl]-5,7-diazaspiro[3.5]nonane-6,8-dione (Example 5, step 2) and iodomethane.

Example 6

8-[2,6-Difluoro-4-(2-phenylethynyl)phenyl]-6-methyl-6,8-diazaspiro[4.5]decane-7,9-dione

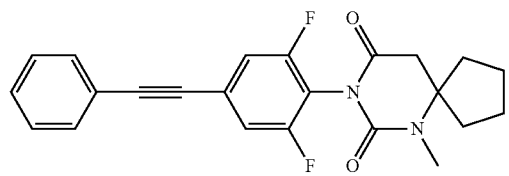

Step 1: Methyl 2-[1-[(4-bromo-2,6-difluoro-phenyl)carbamoylamino]cyclopentyl]acetate 4-Bromo-2,6-difluorobenzoic acid (300 mg, 1.27 mmol) was dissolved in toluene (3.0 ml) and Et$_3$N (141 mg, 0.194 ml, 1.39 mmol, 1.1 equiv.) and DPPA (348 mg, 0.27 ml, 1.27 mmol, 1 equiv.) were added at room temperature. The mixture was stirred for 30 minutes at 100° C. To the mixture methyl 2-(1-aminocyclopentyl)acetate (199 mg, 1.27 mmol, 1 equiv.) was added and stirred for 1 hour at room temperature. The reaction mixture was loaded directly onto a silica gel column. The crude product was purified by flash chromatography eluting with an ethyl acetate:heptane 0:100 to 60:40 gradient. The desired methyl 2-[1-[(4-bromo-2,6-difluoro-phenyl)carbamoylamino]cyclopentyl]acetate (275 mg, 56% yield) was obtained as a white solid, MS:m/e=391.1/393.1 (M+H$^+$).

Step 2: 8-(4-Bromo-2,6-difluoro-phenyl)-6,8-diazaspiro[4.5]decane-7,9-dione

The title compound was obtained as a white solid, MS: m/e=359.0/361.0 (M+H$^+$), using chemistry similar to that described in Example 1, step 3 starting from methyl 2-[1-[(4-bromo-2,6-difluoro-phenyl)carbamoylamino]cyclopentyl]acetate (Example 6, step 1).

Step 3: 8-[2,6-Difluoro-4-(2-phenylethynyl)phenyl]-6,8-diazaspiro[4.5]decane-7,9-dione The title compound was obtained as a yellow solid, MS: m/e=381.2 (M+H$^+$), using chemistry similar to that described in Example 1, step 1 from 8-(4-bromo-2,6-difluoro-phenyl)-6,8-diazaspiro[4.5]decane-7,9-dione (Example 6, step 2) and phenylacetylene.

Step 4: 8-[2,6-Difluoro-4-(2-phenylethynyl)phenyl]-6-methyl-6,8-diazaspiro[4.5]decane-7,9-dione The title compound was obtained as a light yellow solid, MS: m/e=395.3 (M+H$^+$), using chemistry similar to that described in Example 1, step 4 starting from 8-[2,6-difluoro-4-(2-phenylethynyl)phenyl]-6,8-diazaspiro[4.5]decane-7,9-dione (Example 6, step 3) and iodomethane.

Example 7

(5RS)-3-[2,6-Difluoro-4-(2-phenylethynyl)phenyl]-1,5,6,6-tetramethyl-hexahydropyrimidine-2,4-dione

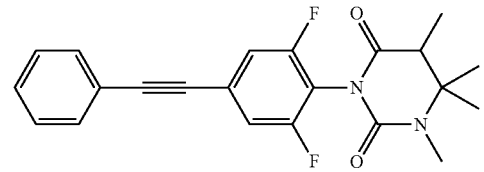

Step 1: Methyl (2RS)-3-[[2,6-difluoro-4-(2-phenylethynyl)phenyl]carbamoylamino]-2,3-dimethyl-butanoate The title compound was obtained as a yellow oil, MS: m/e=401.3 (M+H$^+$), using chemistry similar to that described in Example 1, step 2 starting from 2,6-difluoro-4-phenylethynyl-phenylamine (Example 1, step 1) and methyl (2R5)-3-amino-2,3-dimethyl-butanoate hydrochloride.

Step 2: (5RS)-3-[2,6-difluoro-4-(2-phenylethynyl)phenyl]-5,6,6-trimethyl-hexahydropyrimidine-2,4-dione The title compound was obtained as a light yellow solid, MS: m/e=369.2 (M+H$^+$), using chemistry similar to that described in Example 1, step 3 starting from methyl (2RS)-3-[[2,6-difluoro-4-(2-phenylethynyl)phenyl]carbamoylamino]-2,3-dimethyl-butanoate (Example 7, step 1).

Step 3: (5RS)-3-[2,6-Difluoro-4-(2-phenylethynyl)phenyl]-1,5,6,6-tetramethyl-hexahydropyrimidine-2,4-dione The title compound was obtained as a light yellow oil, MS: m/e=383.3 (M+H⁺), using chemistry similar to that described in Example 1, step 4 starting from (5RS)-3-[2,6-difluoro-4-(2-phenylethynyl)phenyl]-5,6,6-trimethyl-hexahydropyrimidine-2,4-dione (Example 7, step 2) and iodomethane.

Example 8

(9aRS)-7-[2,6-Difluoro-4-(2-phenylethynyl)phenyl]-3,4,9,9a-tetrahydro-1H-pyrimido[6,1-c][1,4]oxazine-6,8-dione

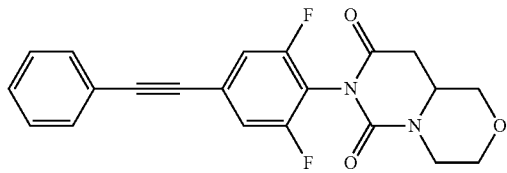

The title compound was obtained as a white solid, MS: m/e=383.1 (M+H⁺), using chemistry similar to that described in Example 1, step 2 starting from 2,6-difluoro-4-phenylethynyl-phenylamine (Example 1, step 1) and methyl 2-[(3RS)-morpholin-3-yl]acetate hydrochloride.

Example 9

3-[2-Chloro-6-fluoro-4-[2-(3-pyridyl)ethynyl]phenyl]-1,6,6-trimethyl-hexahydropyrimidine-2,4-dione

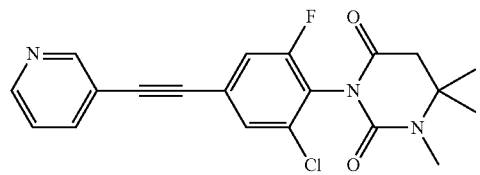

Step 1: 2-Chloro-6-fluoro-4-[2-(3-pyridyl)ethynyl]aniline

The title compound was obtained as an orange solid, MS: m/e=247.1/249.1 (M+H⁺), using chemistry similar to that described in Example 1, step 1 from 4-bromo-2-chloro-6-fluoroaniline and 3-ethynylpyridine.

Step 2: 3-[-2-chloro-6-fluoro-4[-2-(3-pyridyl)ethynyl]phenyl]-6,6-dimethyl-hexahydropyrimidine-2,4-dione The title compound was obtained as a white solid, MS: m/e=372.2/374.2 (M+H⁺), using chemistry similar to that described in Example 1, step 2 starting from 2-chloro-6-fluoro-4-[2-(3-pyridyl)ethynyl]aniline (Example 9, step 1) and methyl 3-amino-3-methylbutanoate.

Step 3: 3-[2-Chloro-6-fluoro-4-[2-(3-pyridyl)ethynyl]phenyl]-1,6,6-trimethyl-hexahydropyrimidine-2,4-dione The title compound was obtained as a light yellow solid, MS: m/e=386.2/388.2 (M+H⁺), using chemistry similar to that described in Example 1, step 4 starting from 3-[2-chloro-6-fluoro-4-[2-(3-pyridyl)ethynyl]phenyl]-6,6-dimethyl-hexahydropyrimidine-2,4-dione (Example 9, step 2) and iodomethane.

Example 10

3-[2-Chloro-6-fluoro-4-[2-(3-pyridyl)ethynyl]phenyl]-1-ethyl-6,6-dimethyl-hexahydropyrimidine-2,4-dione

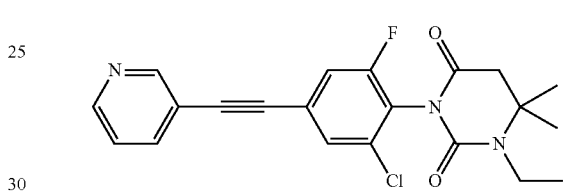

The title compound was obtained as a light oil, MS: m/e=400.3/402.2 (M+H⁺), using chemistry similar to that described in Example 1, step 4 starting from 3-[2-chloro-6-fluoro-4-[2-(3-pyridyl)ethynyl]phenyl]-6,6-dimethyl-hexahydropyrimidine-2,4-dione (Example 9, step 2) and iodoethane.

Example 11

(4aRS,7aSR)-3-[2,6-Difluoro-4-(2-phenylethynyl)phenyl]-1-methyl-5,6,7,7a-tetrahydro-4aH-cyclopenta[d]pyrimidine-2,4-dione

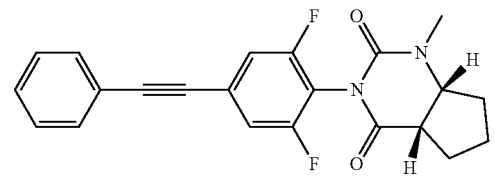 [SMILES: CN1C(=O)N(c2c(F)cc(C#Cc3ccccc3)cc2F)C(=O)[C@H]2CCC[C@H]21]

Step 1: Ethyl (1RS,2SR)-2-[[2,6-difluoro-4-(2-phenylethynyl)phenyl]carbamoylamino]cyclopentanecarboxylate The title compound was obtained as a light yellow solid, MS: m/e=413.3 (M+H⁺), using chemistry similar to that described in Example 1, step 2 starting from 2,6-difluoro-4-phenylethynyl-phenylamine (Example 1, step 1) and ethyl (1RS,2SR)-2-aminocyclopentanecarboxylate hydrochloride.

Step 2: (4aRS,7aSR)-3-[2,6-Difluoro-4-(2-phenylethynyl)phenyl]-1,4a,5,6,7,7a-hexahydrocyclopenta[d]pyrimidine-2,4-dione The title compound was obtained as a light yellow solid, MS: m/e=367.3 (M+H⁺), using chemistry similar to that described in Example 1, step 3 starting from ethyl (1RS,2SR)-2-[[2,6-difluoro-4-(2-phenylethynyl)phenyl]carbamoylamino]cyclopentanecarboxylate (Example 11, step 1).

Step 3: (4aRS,7aSR)-3-[2,6-Difluoro-4-(2-phenylethynyl)phenyl]-1-methyl-5,6,7,7a-tetrahydro-4aH-cyclopenta[d]pyrimidine-2,4-dione The title compound was obtained as a yellow solid, MS: m/e=381.2 (M+H⁺), using chemistry similar to that described in Example 1, step 4 starting from (4aRS,7aSR)-3-[2,6-difluoro-4-(2-phenylethynyl)phenyl]-1,4a,5,6,7,7a-hexahydrocyclopenta[d]pyrimidine-2,4-dione (Example 11, step 2) and iodomethane.

Example 12

(5RS)-8-[2,6-Difluoro-4-(2-phenylethynyl)phenyl]-6-methyl-2-oxa-6,8-diazaspiro[4.5]decane-7,9-dione

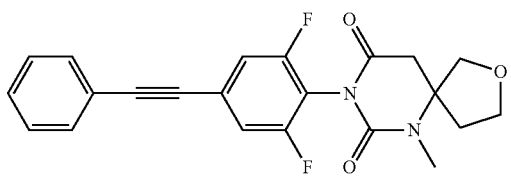 [SMILES: CN1C(=O)N(c2c(F)cc(C#Cc3ccccc3)cc2F)C(=O)CC12CCOC2]

Step 1: Methyl 2-[(3RS)-3-[[2,6-difluoro-4-(2-phenylethynyl)phenyl]carbamoylamino]tetrahydrofuran-3-yl]acetate The title compound was obtained as a white solid, MS: m/e=415.2 (M+H⁺), using chemistry similar to that described in Example 5, step 1 starting from 2,6-difluoro-4-phenylethynyl-phenylamine (Example 1, step 1) and methyl 2-[(3RS)-3-aminotetrahydrofuran-3-yl]acetate.

Step 2: (5RS)-8-[2,6-Difluoro-4-(2-phenylethynyl)phenyl]-2-oxa-6,8-diazaspiro[4.5]decane-7,9-dione The title compound was obtained as a white solid, MS: m/e=383.2 (M+H⁺), using chemistry similar to that described in Example 1, step 3 starting from methyl 2-[(3RS)-3-[[2,6-difluoro-4-(2-phenylethynyl)phenyl]carbamoylamino]tetrahydrofuran-3-yl]acetate (Example 12, step 1).

Step 3: (5RS)-8-[2,6-Difluoro-4-(2-phenylethynyl)phenyl]-6-methyl-2-oxa-6,8-diazaspiro[4.5]decane-7,9-dione The title compound was obtained as a white solid, MS: m/e=397.2 (M+H⁺), using chemistry similar to that described in Example 1, step 4 starting from (5RS)-8-[2,6-difluoro-4-(2-phenylethynyl)phenyl]-2-oxa-6,8-diazaspiro[4.5]decane-7,9-dione (Example 12, step 2) and iodomethane.

Example 13

(6RS)-3-[2,6-Difluoro-4-(2-phenylethynyl)phenyl]-1,6-dimethyl-6-phenyl-hexahydropyrimidine-2,4-dione

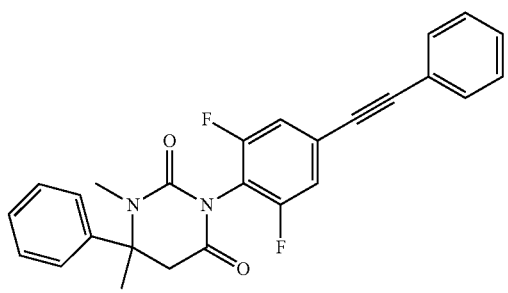 [SMILES: CN1C(=O)N(c2c(F)cc(C#Cc3ccccc3)cc2F)C(=O)CC1(C)c1ccccc1]

Step 1: Ethyl (3RS)-3-[[2,6-difluoro-4-(2-phenylethynyl)phenyl]carbamoylamino]-3-phenyl-butanoate The title compound was obtained as a brown foam, MS: m/e=463.3 (M+H⁺), using chemistry similar to that described in Example 5, step 1 starting from 2,6-difluoro-4-phenylethynyl-phenylamine (Example 1, step 1) and ethyl (3RS)-3-amino-3-phenyl-butanoate.

Step 2: (6RS)-3-[2,6-Difluoro-4-(2-phenylethynyl)phenyl]-6-methyl-6-phenyl-hexahydropyrimidine-2,4-dione The title compound was obtained as a white solid, MS: m/e=417.3 (M+H⁺), using chemistry similar to that described in Example 1, step 3 starting from ethyl (3RS)-3-[[2,6-difluoro-4-(2-phenylethynyl)phenyl]carbamoylamino]-3-phenyl-butanoate (Example 13, step 1).

Step 3: (6RS)-3-[2,6-Difluoro-4-(2-phenylethynyl)phenyl]-1,6-dimethyl-6-phenyl-hexahydropyrimidine-2,4-dione The title compound was obtained as a white solid, MS: m/e=431.3 (M+H⁺), using chemistry similar to that described in Example 1, step 4 starting from (6RS)-3-[2,6-difluoro-4-(2-phenylethynyl)phenyl]-6-methyl-6-phenyl-hexahydropyrimidine-2,4-dione (Example 13, step 2) and iodomethane.

Example 14

(4aRS,7aRS)-3-[2,6-Difluoro-4-(2-phenylethynyl)phenyl]-1,7a-dimethyl-4a,5,6,7-tetrahydrocyclopenta[d]pyrimidine-2,4-dione

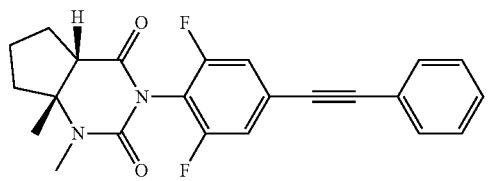 [SMILES: CN1C(=O)N(c2c(F)cc(C#Cc3ccccc3)cc2F)C(=O)[C@H]2CCC[C@]21C]

Step 1: (4aRS,7aSR)-3-[2,6-Difluoro-4-(2-phenyl-ethynyl)phenyl]-7a-methyl-4a,5,6,7-tetrahydro-1H-cyclopenta[d]pyrimidine-2,4-dione The title compound was obtained as a light yellow solid, MS: m/e=381.3 (M+H⁺), using chemistry similar to that described in Example 1, step 2 starting from 2,6-difluoro-4-phenylethynyl-phenylamine (Example 1, step 1) and (1RS,2SR)-2-amino-2-methylcyclopentanecarboxylic acid hydrochloride.

Step 2: (4aRS,7aRS)-3-[2,6-Difluoro-4-(2-phenyl-ethynyl)phenyl]-1,7a-dimethyl-4a,5,6,7-tetrahydro-cyclopenta[d]pyrimidine-2,4-dione The title compound was obtained as a light yellow solid, MS: m/e=395.3 (M+H⁺), using chemistry similar to that described in Example 1, step 4 starting from (4aRS,7aSR)-3-[2,6-difluoro-4-(2-phenylethynyl)phenyl]-7a-methyl-4a,5,6,7-tetrahydro-1H-cyclopenta[d]pyrimidine-2,4-dione (Example 14, step 1) and iodomethane.

Example 15

(6RS)-3-[2,6-Difluoro-4-(2-phenylethynyl)phenyl]-1,6-dimethyl-6-phenyl-hexahydropyrimidine-2,4-dione

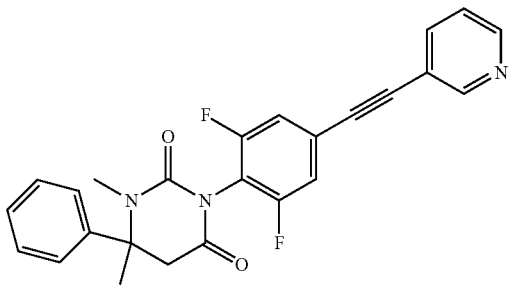 [SMILES: CN1C(=O)N(c2c(F)cc(C#Cc3cccnc3)cc2F)C(=O)CC1(C)c1ccccc1]

Step 1: 2,6-Difluoro-4-[2-(3-pyridyl)ethynyl]aniline

The title compound was obtained as a light brown solid, MS: m/e=231.1 (M+H⁺), using chemistry similar to that described in Example 1, step 1 from 2,6-difluoro-4-iodoaniline and 3-ethynylpyridine.

Step 2: Ethyl (3RS)-3-[[2,6-difluoro-4-[2-(3-pyridyl)ethynyl]phenyl]carbamoylamino]-3-phenyl-butanoate The title compound was obtained as a white solid, MS: m/e=464.2 (M+H⁺), using chemistry similar to that described in Example 5, step 1 starting from 2,6-difluoro-4-[2-(3-pyridyl)ethynyl]aniline (Example 15, step 1) and ethyl (3RS)-3-amino-3-phenyl-butanoate.

Step 3: (6RS)-3-[2,6-Difluoro-4-[2-(3-pyridyl)ethynyl]phenyl]-6-methyl-6-phenyl-hexahydropyrimidine-2,4-dione The title compound was obtained as a yellow solid, MS: m/e=418.2 (M+H⁺), using chemistry similar to that described in Example 1, step 3 starting from ethyl (3RS)-3-[[2,6-difluoro-4-[2-(3-pyridyl)ethynyl]phenyl]carbamoylamino]-3-phenyl-butanoate (Example 15, step 2).

Step 4: (6RS)-3-[2,6-difluoro-4-[2-(3-pyridyl)ethynyl]phenyl]-1,6-dimethyl-6-phenyl-hexahydropyrimidine-2,4-dione The title compound was obtained as a yellow solid, MS: m/e=432.2 (M+H⁺), using chemistry similar to that described in Example 1, step 4 starting from (6RS)-3-[2,6-difluoro-4-[2-(3-pyridyl)ethynyl]phenyl]-6-methyl-6-phenyl-hexahydropyrimidine-2,4-dione (Example 15, step 3) and iodomethane.

Example 16

(6RS)-3-[2,6-Difluoro-4-[2-(3-pyridyl)ethynyl]phenyl]-1-ethyl-6-methyl-6-phenyl-hexahydropyrimidine-2,4-dione

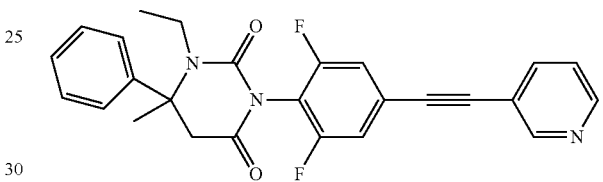

The title compound was obtained as a yellow oil, MS: m/e=446.4 (M+H⁺), using chemistry similar to that described in Example 1, step 4 starting from (6RS)-3-[2,6-difluoro-4-[2-(3-pyridyl)ethynyl]phenyl]-6-methyl-6-phenyl-hexahydropyrimidine-2,4-dione (Example 15, step 3) and iodoethane.

Example 17

(6RS)-3-[2,6-Difluoro-4-(2-phenylethynyl)phenyl]-1-methyl-8-oxa-1,3-diazaspiro[5.5]undecane-2,4-dione

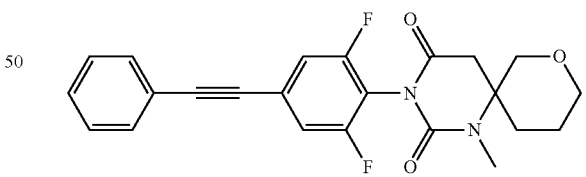

Step 1: Methyl 2-[(3RS)-3-[[2,6-difluoro-4-(2-phenylethynyl)phenyl]carbamoylamino]tetrahydropyran-3-yl]acetate The title compound was obtained as a light yellow solid, MS: m/e=429.3 (M+H⁺), using chemistry similar to that described in Example 5, step 1 starting from 2,6-difluoro-4-phenylethynyl-phenylamine (Example 1, step 1) and methyl methyl 2-[(3RS)-3-aminotetrahydropyran-3-yl]acetate.

Step 2: (6RS)-3-[2,6-Difluoro-4-(2-phenylethynyl)phenyl]-8-oxa-1,3-diazaspiro[5.5]undecane-2,4-dione The title compound was obtained as a white solid, MS: m/e=397.3 (M+H$^+$), using chemistry similar to that described in Example 1, step 3 starting from methyl methyl 2-[(3RS)-3-[[2,6-difluoro-4-(2-phenylethynyl)phenyl]carbamoylamino]tetrahydropyran-3-yl]acetate (Example 17, step 1).

Step 3: (6RS)-3-[2,6-Difluoro-4-(2-phenylethynyl)phenyl]-1-methyl-8-oxa-1,3-diazaspiro[5.5]undecane-2,4-dione The title compound was obtained as a white solid, MS: m/e=411.2 (M+H$^+$), using chemistry similar to that described in Example 1, step 4 starting from (6RS)-3-[2,6-difluoro-4-(2-phenylethynyl)phenyl]-8-oxa-1,3-diazaspiro[5.5]undecane-2,4-dione (Example 17, step 2) and iodomethane.

Example 18

(6RS)-3-[2,6-Difluoro-4-(2-phenylethynyl)phenyl]-6-ethyl-1,6-dimethyl-hexahydropyrimidine-2,4-dione

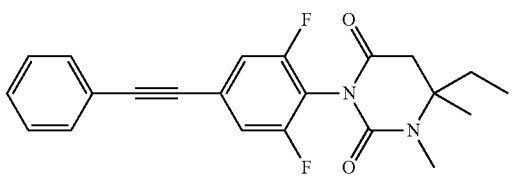 [SMILES: CCC1(C)CC(=O)N(c2c(F)cc(C#Cc3ccccc3)cc2F)C(=O)N1C]

Step 1: Methyl (3RS)-3-[[2,6-difluoro-4-(2-phenylethynyl)phenyl]carbamoylamino]-3-methyl-pentanoate The title compound was obtained as a white solid, MS: m/e=401.3 (M+H$^+$), using chemistry similar to that described in Example 5, step 1 starting from 2,6-difluoro-4-phenylethynyl-phenylamine (Example 1, step 1) and methyl (3RS)-3-amino-3-methyl-pentanoate.

Step 2: (6RS)-3-[2,6-Difluoro-4-(2-phenylethynyl)phenyl]-6-ethyl-6-methyl-hexahydropyrimidine-2,4-dione The title compound was obtained as a light yellow solid, MS: m/e=369.2 (M+H$^+$), using chemistry similar to that described in Example 1, step 3 starting from methyl (3RS)-3-[[2,6-difluoro-4-(2-phenylethynyl)phenyl]carbamoylamino]-3-methyl-pentanoate (Example 18, step 1).

Step 3: (6RS)-3-[2,6-Difluoro-4-(2-phenylethynyl)phenyl]-6-ethyl-1,6-dimethyl-hexahydropyrimidine-2,4-dione The title compound was obtained as a colorless oil, MS: m/e=383.2 (M+H$^+$), using chemistry similar to that described in Example 1, step 4 starting from (6RS)-3-[2,6-difluoro-4-(2-phenylethynyl)phenyl]-6-ethyl-6-methyl-hexahydropyrimidine-2,4-dione (Example 18, step 2) and iodomethane.

Example 19

(6S)-3-[2,6-Difluoro-4-(2-phenylethynyl)phenyl]-1,6-dimethyl-6-phenyl-hexahydropyrimidine-2,4-dione

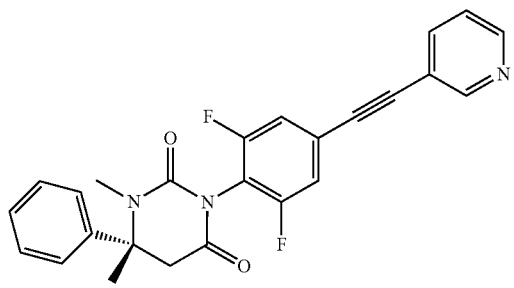 [SMILES: CN1C(=O)N(c2c(F)cc(C#Cc3cccnc3)cc2F)C(=O)C[C@]1(C)c1ccccc1]

The title compound, a white solid, MS: m/e=432.2 (M+H$^+$), was prepared by separation of (6RS)-3-[2,6-difluoro-4-[2-(3-pyridyl)ethynyl]phenyl]-1,6-dimethyl-6-phenyl-hexahydropyrimidine-2,4-dione (Example 15) using a chiral column (Chiralpak AD with heptane:isopropanol 60:40 as solvent) collecting peak A.

Example 20

(6R)-3-[2,6-Difluoro-4-(2-phenylethynyl)phenyl]-1,6-dimethyl-6-phenyl-hexahydropyrimidine-2,4-dione

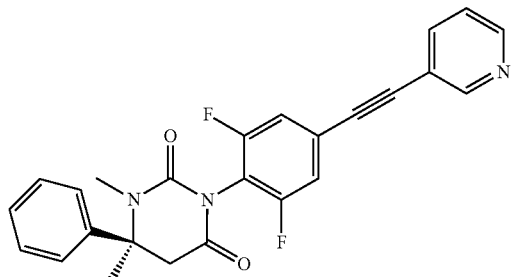

The title compound, a white solid, MS: m/e=432.2 (M+H$^+$), was prepared by separation of (6RS)-3-[2,6-difluoro-4-[2-(3-pyridyl)ethynyl]phenyl]-1,6-dimethyl-6-phenyl-hexahydropyrimidine-2,4-dione (Example 15) using a chiral column (Chiralpak AD with heptane:isopropanol 60:40 as solvent) collecting peak B.

Example 21

3-[2,6-Difluoro-4-(2-phenylethynyl)phenyl]-6,6-diethyl-hexahydropyrimidine-2,4-dione

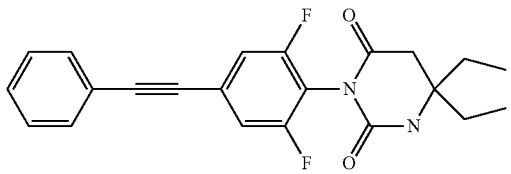

Step 1: Methyl 3-[[2,6-difluoro-4-(2-phenylethynyl)phenyl]carbamoylamino]-3-ethyl-pentanoate The title compound was obtained as a white solid, MS: m/e=415.3 (M+H$^+$), using chemistry similar to that described in Example 5, step 1 starting from 2,6-difluoro-4-phenylethynyl-phenylamine (Example 1, step 1) and methyl 3-amino-3-ethylpentanoate.

Step 2: 3-[2,6-Difluoro-4-(2-phenylethynyl)phenyl]-6,6-diethyl-hexahydropyrimidine-2,4-dione The title compound was obtained as a white solid, MS: m/e=383.2 (M+H$^+$), using chemistry similar to that described in Example 1, step 3 starting from methyl 3-[[2,6-difluoro-4-(2-phenylethynyl)phenyl]carbamoylamino]-3-ethyl-pentanoate (Example 21, step 1).

Example 22

3-[2,6-Difluoro-4-(2-phenylethynyl)phenyl]-6,6-diethyl-1-methyl-hexahydropyrimidine-2,4-dione

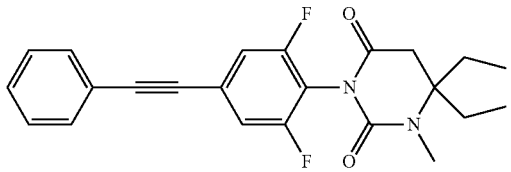

The title compound was obtained as a light yellow oil, MS: m/e=397.3 (M+H$^+$), using chemistry similar to that described in Example 1, step 4 starting from 3-[2,6-difluoro-4-(2-phenylethynyl)phenyl]-6,6-diethyl-hexahydropyrimidine-2,4-dione (Example 21) and iodomethane.

Example 23

(6RS)-1,6-Dimethyl-6-phenyl-3-[5-(2-phenylethynyl)-2-pyridyl]hexahydropyrimidine-2,4-dione

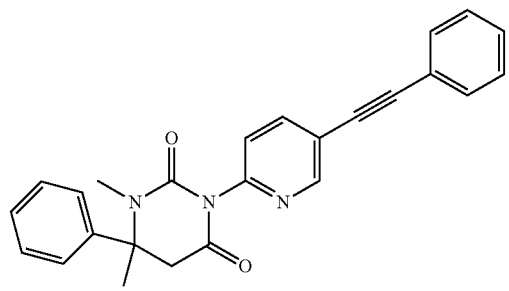 [SMILES: CN1C(=O)N(c2ccc(C#Cc3ccccc3)cn2)C(=O)CC1(C)c1ccccc1]

Step 1: 5-(2-Phenylethynyl)pyridin-2-amine

The title compound was obtained as a yellow solid, MS: m/e=195.2 (M+H$^+$), using chemistry similar to that described in Example 1, step 1 from 5-iodopyridin-2-amine and phenylacetylene.

Step 2: Ethyl (3RS)-3-phenyl-3-[[5-(2-phenylethynyl)-2-pyridyl]carbamoylamino]butanoate The title compound was obtained as a light yellow solid, MS: m/e=428.3 (M+H$^+$), using chemistry similar to that described in Example 1, step 2 starting from 5-(2-phenylethynyl)pyridin-2-amine (Example 23, step 1) and ethyl (3RS)-3-amino-3-phenyl-butanoate.

Step 3: (6RS)-6-Methyl-6-phenyl-3-[5-(2-phenylethynyl)-2-pyridyl]hexahydropyrimidine-2,4-dione The title compound was obtained as a light yellow solid, MS: m/e=382.2 (M+H$^+$), using chemistry similar to that described in Example 1, step 3 to form the according acid and by using SOCl$_2$ to form the desired product from ethyl (3RS)-3-phenyl-3-[[5-(2-phenylethynyl)-2-pyridyl]carbamoylamino]butanoate (Example 23 step 2).

Step 4: (6RS)-1,6-Dimethyl-6-phenyl-3-[5-(2-phenylethynyl)-2-pyridyl]hexahydropyrimidine-2 4-dione The title compound was obtained as a yellow solid, MS: m/e=396.2 (M+H$^+$), using chemistry similar to that described in Example 1, step 4 starting from (6RS)-6-methyl-6-phenyl-3-[5-(2-phenylethynyl)-2-pyridyl]hexahydropyrimidine-2,4-dione (Example 23, step 3) and iodomethane.

Example 24

(6RS)-1,6-Dimethyl-6-phenyl-3-[4-(2-phenylethynyl)phenyl]hexahydropyrimidine-2,4-dione

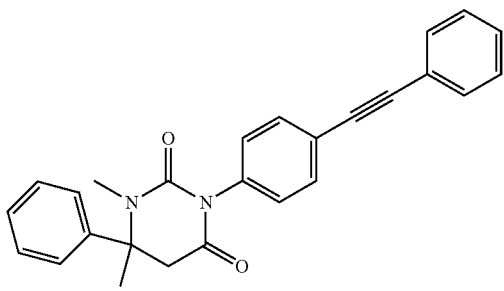 [SMILES: CN1C(=O)N(c2ccc(C#Cc3ccccc3)cc2)C(=O)CC1(C)c1ccccc1]

The title compound was obtained as a yellow solid, MS: m/e=395.2 (M+H⁺), using chemistry similar to that described in Example 13 starting from 4-(phenylethynyl)aniline and ethyl (3RS)-3-amino-3-phenyl-butanoate.

Example 25

(9aRS)-7-[2,6-Difluoro-4-(2-phenylethynyl)phenyl]-9a-methyl-2,3,4,9-tetrahydropyrazino[1,2-c]pyrimidine-1,6,8-trione

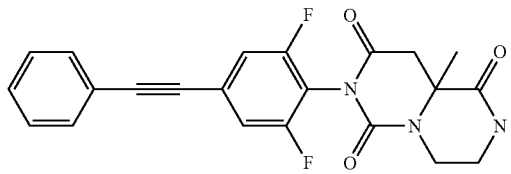

The title compound was obtained as a white solid, MS: m/e=410.2 (M+H⁺), using chemistry similar to that described in Example 1, step 2 starting from 2,6-difluoro-4-phenylethynyl-phenylamine (Example 1, step 1) and methyl 2-[(2RS)-2-methyl-3-oxo-piperazin-2-yl]acetate.

Example 26

(6RS)-3-[2,6-Difluoro-4-(2-phenylethynyl)phenyl]-6-isopropyl-1,6-dimethyl-hexahydropyrimidine-2,4-dione

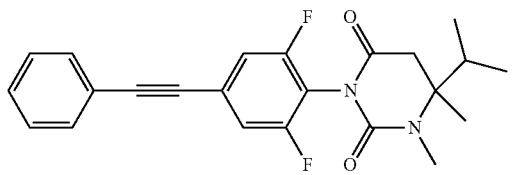

The title compound was obtained as a light yellow solid, MS: m/e=397.2 (M+H⁺), using chemistry similar to that described in Example 13 starting from 2,6-difluoro-4-phenylethynyl-phenylamine (Example 1, step 1) and ethyl (3RS)-3-amino-3,4-dimethyl-pentanoate.

Example 27

(6RS)-3-[2,6-Difluoro-4-(2-phenylethynyl)phenyl]-1,6-dimethyl-6-(2-pyridyl)hexahydropyrimidine-2,4-dione

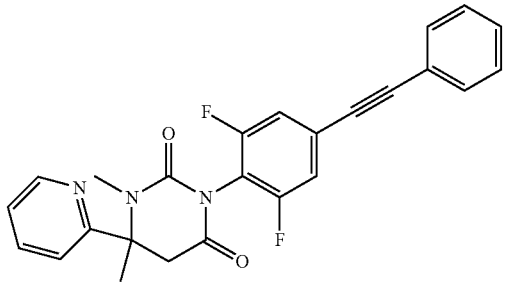

The title compound was obtained as a light yellow solid, MS: m/e=432.2 (M+H⁺), using chemistry similar to that described in Example 13 starting from 2,6-difluoro-4-phenylethynyl-phenylamine (Example 1, step 1) and methyl (3RS)-3-amino-3-(pyridin-2-yl).

Example 28

(6RS)-3-[2,6-Difluoro-4-(2-phenylethynyl)phenyl]-1,6-dimethyl-6-(4-pyridyl)hexahydropyrimidine-2,4-dione

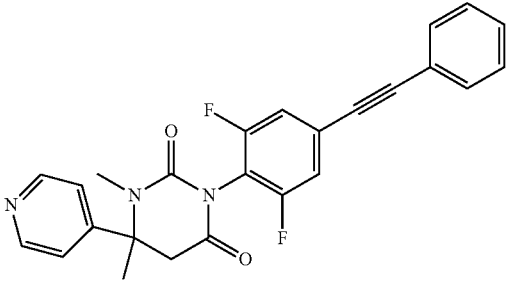 [SMILES: CN1C(=O)N(c2c(F)cc(C#Cc3ccccc3)cc2F)C(=O)CC1(C)c1ccncc1]

The title compound was obtained as a light yellow solid, MS: m/e=432.2 (M+H⁺), using chemistry similar to that described in Example 13 starting from 2,6-difluoro-4-phenylethynyl-phenylamine (Example 1, step 1) and methyl (3RS)-3-amino-3-(pyridin-4-yl).

Example 29

(6RS)-3-[2,6-Difluoro-4-(2-phenylethynyl)phenyl]-1,6-dimethyl-6-(3-pyridyl)hexahydropyrimidine-2,4-dione

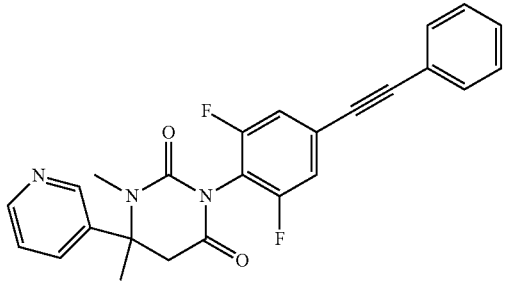 [SMILES: CN1C(=O)N(c2c(F)cc(C#Cc3ccccc3)cc2F)C(=O)CC1(C)c1cccnc1]

The title compound was obtained as a colorless oil, MS: m/e=432.2 (M+H⁺), using chemistry similar to that described in Example 13 starting from 2,6-difluoro-4-phenylethynyl-phenylamine (Example 1, step 1) and methyl (3RS)-3-amino-3-(pyridin-3-yl).

Example 30

(6RS)-3-[2,6-Difluoro-4-(2-phenylethynyl)phenyl]-6-(methoxymethyl)-1,6-dimethyl-hexahydropyrimidine-2,4-dione

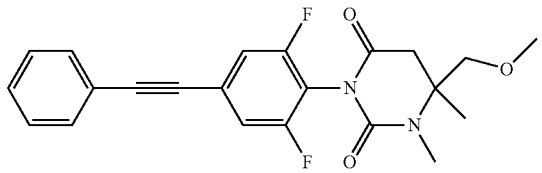 [SMILES: COCC1(C)CC(=O)N(c2c(F)cc(C#Cc3ccccc3)cc2F)C(=O)N1C]

The title compound was obtained as a light yellow solid, MS: m/e=399.2 (M+H$^+$), using chemistry similar to that described in Example 1, step 2 and step 4 starting from 2,6-difluoro-4-phenylethynyl-phenylamine (Example 1, step 1) and methyl (3RS)-3-amino-4-methoxy-3-methyl-butanoate.

Example 31

(6RS)-6-Cyclohexyl-3-[2,6-difluoro-4-[2-(3-pyridyl)ethynyl]phenyl]-1,6-dimethyl-hexahydropyrimidine-2,4-dione

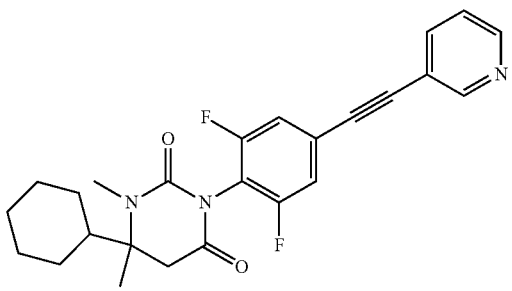 [SMILES: CN1C(=O)N(c2c(F)cc(C#Cc3cccnc3)cc2F)C(=O)CC1(C)C1CCCCC1]

The title compound was obtained as a white solid, MS: m/e=438.2 (M+H$^+$), using chemistry similar to that described in Example 13 starting from 2,6-difluoro-4-[2-(3-pyridyl)ethynyl]aniline (Example 15, step 1) and ethyl (3RS)-3-amino-3-cyclohexylbutanoate.

Example 32

(6RS)-3-[3-Chloro-5-(2-phenylethynyl)-2-pyridyl]-1,6-dimethyl-6-phenyl-hexahydropyrimidine-2,4-dione

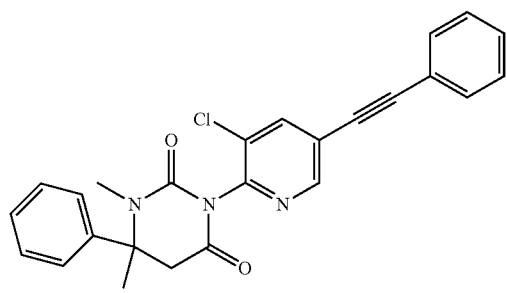 [SMILES: CN1C(=O)N(c2ncc(C#Cc3ccccc3)cc2Cl)C(=O)CC1(C)c1ccccc1]

Step 1: Ethyl (3RS)-3-[(5-bromo-3-chloro-2-pyridyl)carbamoylamino]-3-phenyl-butanoate The title compound was obtained as a white solid, MS: m/e=440.1/442.1 (M+H$^+$), using chemistry similar to that described in Example 6, step 1 starting from 5-bromo-3-chloropicolinic acid and ethyl (3RS)-3-amino-3-phenyl-butanoate.

Step 2: (6RS)-3-(5-Bromo-3-chloro-2-pyridyl)-6-methyl-6-phenyl-hexahydropyrimidine-2,4-dione The title compound was obtained as a yellow solid, MS: m/e=394.0/396.0 (M+H$^+$), using chemistry similar to that described in Example 1, step 3 to form the according acid and by using SOCl$_2$ to form the desired product from ethyl (3RS)-3-[(5-bromo-3-chloro-2-pyridyl)carbamoylamino]-3-phenyl-butanoate (Example 32, step 1).

Step 3: (6RS)-3-(5-Bromo-3-chloro-2-pyridyl)-1,6-dimethyl-6-phenyl-hexahydropyrimidine-2,4-dione The title compound was obtained as a white solid, MS: m/e=408.1/410.1 (M+H$^+$), using chemistry similar to that described in Example 1, step 4 starting from (6RS)-3-(5-bromo-3-chloro-2-pyridyl)-6-methyl-6-phenyl-hexahydropyrimidine-2,4-dione (Example 32, step 2) and iodomethane.

Step 4: (6RS)-3-[3-Chloro-5-(2-phenylethynyl)-2-pyridyl]-1,6-dimethyl-6-phenyl-hexahydropyrimidine-2,4-dione The title compound was obtained as a light yellow oil, MS: m/e=430.2/432.2 (M+H$^+$), using chemistry similar to that described in Example 1, step 1 from (6RS)-3-(5-bromo-3-chloro-2-pyridyl)-1,6-dimethyl-6-phenyl-hexahydropyrimidine-2,4-dione (Example 32, step 3) and phenylacetylene.

Example 33

(6RS)-3-[2-Chloro-6-fluoro-4-[2-(3-pyridyl)ethynyl]phenyl]-1,6-dimethyl-6-(3-pyridyl)hexahydropyrimidine-2,4-dione

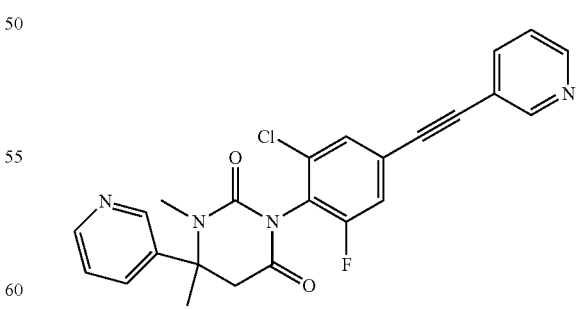

The title compound was obtained as a light brown oil, MS: m/e=449.2/451.2 (M+H$^+$), using chemistry similar to that described in Example 13 starting from 2-chloro-6-fluoro-4-[2-(3-pyridyl)ethynyl]aniline (Example 9, step 1) and methyl (3RS)-3-amino-3-(pyridin-3-yl).

Example 34

(6RS)-3-[2-Chloro-6-fluoro-4-[2-(3-pyridyl)ethynyl]phenyl]-1,6-dimethyl-6-phenyl-hexahydropyrimidine-2,4-dione

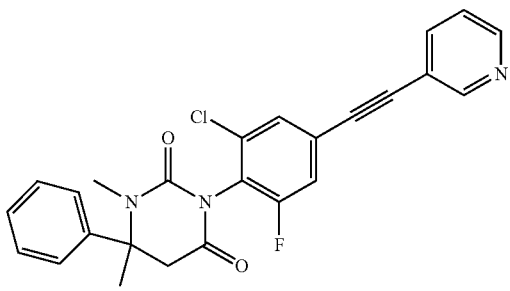 [SMILES: CN1C(=O)N(c2c(F)cc(C#Cc3cccnc3)cc2Cl)C(=O)CC1(C)c1ccccc1]

The title compound was obtained as a light yellow solid, MS: m/e=448.2/450.2 (M+H⁺), using chemistry similar to that described in Example 13 starting from 2-chloro-6-fluoro-4-[2-(3-pyridyl)ethynyl]aniline (Example 9, step 1) and ethyl (3RS)-3-amino-3-phenyl-butanoate.

Example 35

(9aRS)-7-[2,6-Difluoro-4-(2-phenylethynyl)phenyl]-2,9a-dimethyl-4,9-dihydro-3H-pyrazino[1,2-c]pyrimidine-1,6,8-trione

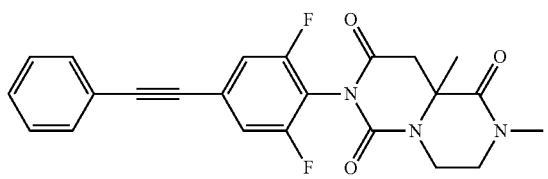

The title compound was obtained as a white solid, MS: m/e=424.2 (M+H⁺), using chemistry similar to that described in Example 1, step 4 starting from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 25) and iodomethane.

Example 36

(9aRS)-7-[2,6-Difluoro-4-(2-phenylethynyl)phenyl]-2-isopropyl-9a-methyl-4,9-dihydro-3H-pyrazino[1,2-c]pyrimidine-1,6,8-trione

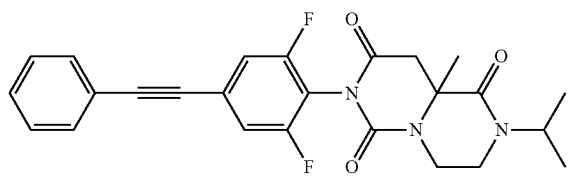 [SMILES: CC(C)N1CCN2C(=O)N(c3c(F)cc(C#Cc4ccccc4)cc3F)C(=O)CC2(C)C1=O]

The title compound was obtained as a white solid, MS: m/e=452.2 (M+H⁺), using chemistry similar to that described in Example 1, step 4 by using NaH instead of Cs₂CO₃ starting from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 25) and 2-iodopropane.

Example 37

(9aRS)-2-Benzyl-7-[2,6-difluoro-4-(2-phenylethynyl)phenyl]-9a-methyl-4,9-dihydro-3H-pyrazino[1,2-c]pyrimidine-1,6,8-trione

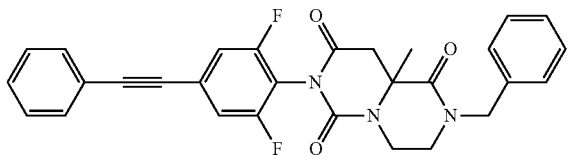 [SMILES: CC12CC(=O)N(c3c(F)cc(C#Cc4ccccc4)cc3F)C(=O)N1CCN(Cc1ccccc1)C2=O]

The title compound was obtained as a white solid, MS: m/e=500.2 (M+H⁺), using chemistry similar to that described in Example 1, step 4 starting from (9aRS)-7-[2,6-difluoro-4-(2-phenylethynyl)phenyl]-9a-methyl-2,3,4,9-tetrahydropyrazino[1,2-c]pyrimidine-1,6,8-trione (Example 25) and (bromomethyl)benzene.

Example 38

(9aRS)-7-[2,6-Difluoro-4-(2-phenylethynyl)phenyl]-9a-methyl-2-phenyl-4,9-dihydro-3H-pyrazino[1,2-c]pyrimidine-1,6,8-trione

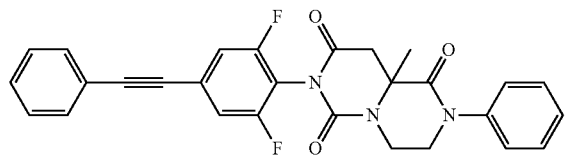

(9aRS)-7-[2,6-Difluoro-4-(2-phenylethynyl)phenyl]-9a-methyl-2,3,4,9-tetrahydropyrazino[1,2-c]pyrimidine-1,6,8-trione (Example 25) (80 mg, 0.195 mmol) was dissolved in dioxane (2.5 ml). Cs₂CO₃ (96 mg, 0.293 mmol, 1.5 equiv.), iodobenzene (0.028 ml, 52 mg, 0.254 mmol, 1.3 equiv.), palladium (II) acetate (8.8 mg, 0.039 mmol, 0.2 equiv.) and Xantphos® (34 mg, 0.059 mmol, 0.3 equiv.) were added at room temperature. The mixture was stirred for 16 hours at 90° C. The reaction mixture was evaporated and loaded directly onto a silica gel column. The crude product was purified by flash chromatography eluting with an ethyl acetate:heptane 0:100 to 100:0 gradient. The desired (9aRS)-7-[2,6-difluoro-4-(2-phenylethynyl)phenyl]-9a-methyl-2-phenyl-4,9-dihydro-3H-pyrazino[1,2-c]pyrimidine-1,6,8-trione (19 mg, 20% yield) was obtained as a light brown solid, MS: m/e=486.2 (M+H⁺).

Example 39

(6RS)-6-(3-Chlorophenyl)-3-[2,6-difluoro-4-[2-(3-pyridyl)ethynyl]phenyl]-1,6-dimethyl-hexahydropyrimidine-2,4-dione

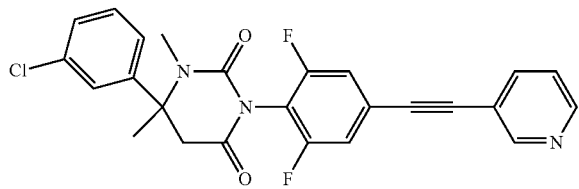 [SMILES: CN1C(=O)N(c2c(F)cc(C#Cc3cccnc3)cc2F)C(=O)CC1(C)c1cccc(Cl)c1]

Step 1: rac-N-[1-(3-Chlorophenyl)ethylidene]-2-methyl-propane-2-sulfinamide 1-(3-Chlorophenyl)ethanone (2 g, 13.1 mmol) was dissolved in 20 ml THF. rac-2-Methylpropane-2-sulfinamide (CAS 146374-27-8) (1.74 g, 14.4 mmol, 1.1 equiv.) and titanium(IV) ethoxide (4.48 g, 4.07 ml, 19.6 mmol, 1.5 equiv.) were added and the mixture was stirred for 16 hours at 60° C. The reaction mixture was cooled and saturated NaHCO$_3$ solution and ethyl acetate were added. The formed suspension was filtered through celite and the filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 60:40 gradient. The desired rac-N-[1-(3-chlorophenyl)ethylidene]-2-methyl-propane-2-sulfinamide (2.73 g, 81% yield) was obtained as a yellow oil, MS: m/e=258.1/260.1 (M+H$^+$).

Step 2: Methyl (3RS)-3-[[(RS)-tert-butylsulfinyl]amino]-3-(3-chlorophenyl)butanoate Activated zinc (5.53 g, 84.6 mmol, 8 equiv.) was suspended in 15 ml THF and copper (I) chloride (1.05 g, 10.6 mmol, 1 equiv.) was added. The mixture was stirred for 30 minutes at 60° C. and a mixture of methyl 2-bromoacetate (2.51 ml, 4.04 g, 26.4 mmol, 2.5 equiv.) in 5 ml THF was added dropwise. After 30 minutes at 60° C. the mixture was cooled to 0-5° C. and a mixture of rac-N-[1-(3-chlorophenyl)ethylidene]-2-methyl-propane-2-sulfinamide (Example 39, step 1) (2.73 g, 10.6 mmol) in 5 ml THF was added dropwise at 0-5° C. The mixture was stirred for 1 hour 0-5° C. Saturated NH$_4$Cl solution and ethyl acetate were added and the formed suspension was filtered through Celite®. The filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 100:0 gradient. The desired methyl (3RS)-3-[[(RS)-tert-butylsulfinyl]amino]-3-(3-chlorophenyl)butanoate (2.44 g, 70% yield) was obtained as a colorless oil, MS: m/e=332.1/334.1 (M+H$^+$).

Step 3: Methyl (3RS)-3-amino-3-(3-chlorophenyl)butanoate

Methyl (3RS)-3-[[(RS)-tert-butylsulfinyl]amino]-3-(3-chlorophenyl)butanoate (Example 39, step 2) (2.44 g, 7.35 mmol) was dissolved in 20 ml dioxane and HCl (4N in dioxane) (9.2 ml, 36.8 mmol, 5 equiv.) was added. The mixture was stirred for 3 hours at room temperature. The reaction mixture was evaporated and extracted with saturated Na$_2$CO$_3$ solution and three times with dichloromethane. The organic layers were combined, dried over sodium sulfate and evaporated to dryness. The crude product was used without further purification. The desired methyl (3RS)-3-amino-3-(3-chlorophenyl)butanoate (1.83 g, quant. yield) was obtained as a light brown oil, MS: m/e=228.1/230.1 (M+H$^+$).

Step 4: (6RS)-6-(3-Chlorophenyl)-3-[2,6-difluoro-4-[2-(3-pyridyl)ethynyl]phenyl]-1,6-dimethyl-hexahydropyrimidine-2,4-dione The title compound was obtained as a light yellow solid, MS: m/e=466.1/468.1 (M+H$^+$), using chemistry similar to that described in Example 13 starting from 2,6-difluoro-4-[2-(3-pyridyl)ethynyl]aniline (Example 15, step 1) and methyl (3RS)-3-amino-3-(3-chlorophenyl)butanoate (Example 39, step 3).

Example 40

(6RS)-6-(2-Chlorophenyl)-3-[2,6-difluoro-4-[2-(3-pyridyl)ethynyl]phenyl]-1,6-dimethyl-hexahydropyrimidine-2,4-dione

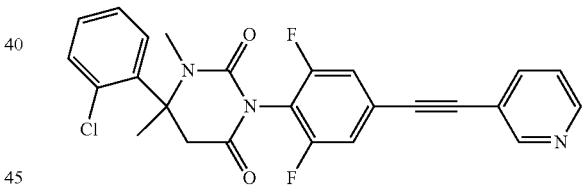

Step 1: Methyl (3RS)-3-amino-3-(2-chlorophenyl)butanoate

The title compound was obtained as a brown oil, MS: m/e=228.1/230.1 (M+H$^+$), using chemistry similar to that described in Example 39, steps 1, 2 and 3 starting from 1-(2-chlorophenyl)ethanone.

Step 2: (6RS)-6-(2-Chlorophenyl)-3-[2,6-difluoro-4-[2-(3-pyridyl)ethynyl]phenyl]-1,6-dimethyl-hexahydropyrimidine-2,4-dione The title compound was obtained as a light yellow solid, MS: m/e=466.1/468.1 (M+H$^+$), using chemistry similar to that described in Example 13 starting from 2,6-difluoro-4-[2-(3-pyridyl)ethynyl]aniline (Example 15, step 1) and methyl (3RS)-3-amino-3-(2-chlorophenyl)butanoate (Example 40, step 1).

Example 41

(6RS)-6-(4-Chlorophenyl)-3-[2,6-difluoro-4-[2-(3-pyridyl)ethynyl]phenyl]-1,6-dimethyl-hexahydropyrimidine-2,4-dione

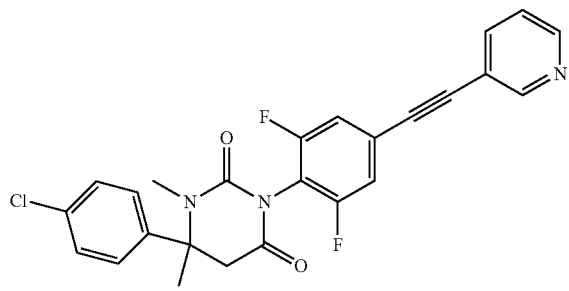 [SMILES: CN1C(=O)N(c2c(F)cc(C#Cc3cccnc3)cc2F)C(=O)CC1(C)c1ccc(Cl)cc1]

Step 1: Methyl (3RS)-3-amino-3-(4-chlorophenyl)butanoate

The title compound was obtained as a brown oil, MS: m/e=228.1/230.1 (M+H$^+$), using chemistry similar to that described in Example 39, steps 1, 2 and 3 starting from 1-(4-chlorophenyl)ethanone.

Step 2: (6RS)-6-(4-Chlorophenyl)-3-[2,6-difluoro-4-[2-(3-pyridyl)ethynyl]phenyl]-1,6-dimethyl-hexahydropyrimidine-2,4-dione The title compound was obtained as a light yellow solid, MS: m/e=466.1/468.1 (M+H$^+$), using chemistry similar to that described in Example 13 starting from 2,6-difluoro-4-[2-(3-pyridyl)ethynyl]aniline (Example 15, step 1) and methyl (3RS)-3-amino-3-(4-chlorophenyl)butanoate (Example 41, step 1).

Example 42

(6RS)-3-[2,6-Difluoro-4-[2-(3-pyridyl)ethynyl]phenyl]-6-(3-methoxyphenyl)-1,6-dimethyl-hexahydropyrimidine-2,4-dione

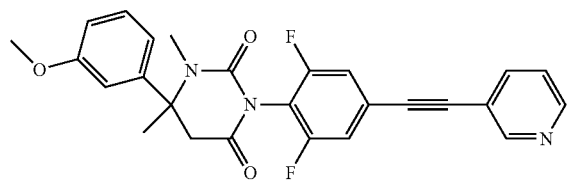

The title compound was obtained as a white solid, MS: m/e=462.2 (M+H$^+$), using chemistry similar to that described in Example 13 starting from 2,6-difluoro-4-[2-(3-pyridyl)ethynyl]aniline (Example 15, step 1) and methyl (3RS)-3-amino-3-(3-methoxyphenyl)butanoate.

Example 43

(6RS)-6-tert-Butyl-3-[2,6-difluoro-4-(2-phenylethynyl)phenyl]-6-methyl-hexahydropyrimidine-2,4-dione

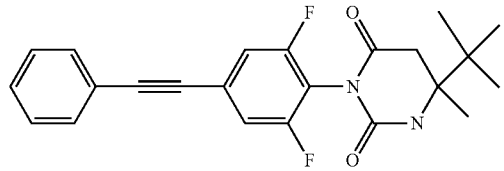

The title compound was obtained as a light yellow solid, MS: m/e=397.2 (M+H$^+$), using chemistry similar to that described in Example 1, steps 2 and 4 starting from 2,6-difluoro-4-phenylethynyl-phenylamine (Example 1, step 1) and methyl (3RS)-3-amino-3,4,4-trimethylpentanoate hydrochloride.

Example 44

(6RS)-6-tert-Butyl-3-[2,6-difluoro-4-(2-phenylethynyl)phenyl]-1,6-dimethyl-hexahydropyrimidine-2,4-dione

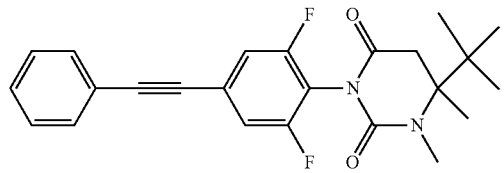 [SMILES: CC(C)(C)C1(C)CC(=O)N(c2c(F)cc(C#Cc3ccccc3)cc2F)C(=O)N1]

The title compound was obtained as a colorless oil, MS: m/e=411.2 (M+H$^+$), using chemistry similar to that described in Example 1, step 4 starting from (6RS)-6-tert-butyl-3-[2,6-difluoro-4-(2-phenylethynyl)phenyl]-6-methyl-hexahydropyrimidine-2,4-dione (Example 44) and iodomethane.

Example 45

(6RS)-3-[3-Fluoro-5-(2-phenylethynyl)-2-pyridyl]-1,6-dimethyl-6-phenyl-hexahydropyrimidine-2,4-dione

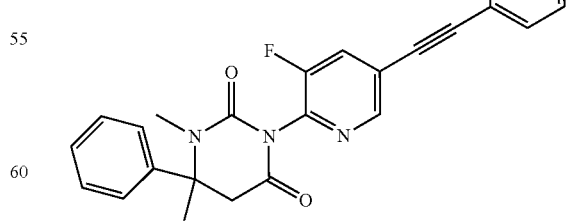

The title compound was obtained as a white solid, MS: m/e=414.2 (M+H$^+$), using chemistry similar to that described in Example 32 starting from 5-bromo-3-fluoropicolinic acid and ethyl (3RS)-3-amino-3-phenyl-butanoate.

Example 46

(6RS)-1,6-Dimethyl-6-phenyl-3-[5-(2-phenylethynyl)-3-(trifluoromethyl)-2-pyridyl]hexahydropyrimidine-2,4-dione

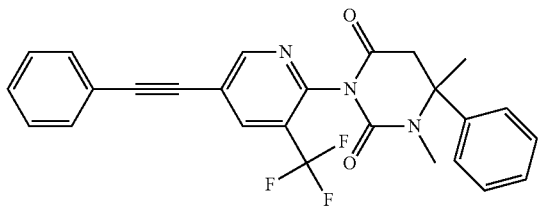 [SMILES: CN1C(=O)N(c2ncc(C#Cc3ccccc3)cc2C(F)(F)F)C(=O)CC1(C)c1ccccc1]

The title compound was obtained as a yellow solid, MS: m/e=464.2 (M+H⁺), using chemistry similar to that described in Example 32 starting from 5-bromo-3-(trifluoromethyl)picolinic acid and ethyl (3RS)-3-amino-3-phenyl-butanoate.

Example 47

(6RS)-3-[2-Chloro-4-(2-phenylethynyl)phenyl]-1,6-dimethyl-6-(3-pyridyl)hexahydropyrimidine-2,4-dione

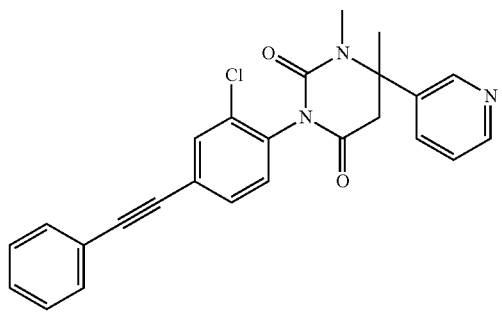 [SMILES: CN1C(=O)N(c2ccc(C#Cc3ccccc3)cc2Cl)C(=O)CC1(C)c1cccnc1]

The title compound was obtained as a yellow oil, MS: m/e=430.2/432.2 (M+H⁺), using chemistry similar to that described in Example 13 starting from 2-chloro-4-(2-phenylethynyl)aniline (Example 2, step 1) and methyl (3RS)-3-amino-3-(pyridin-3-yl).

Example 48

(6RS)-3-[2,6-Difluoro-4-[2-(3-pyridyl)ethynyl]phenyl]-6-ethyl-1-methyl-6-phenyl-hexahydropyrimidine-2,4-dione

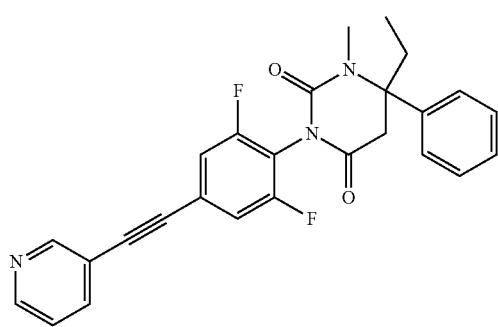 [SMILES: CCC1(c2ccccc2)CC(=O)N(c2c(F)cc(C#Cc3cccnc3)cc2F)C(=O)N1C]

The title compound was obtained as a light yellow solid, MS: m/e=446.2 (M+H⁺), using chemistry similar to that described in Example 13 starting from 2,6-difluoro-4-[2-(3-pyridyl)ethynyl]aniline (Example 15, step 1) and methyl (3RS)-3-amino-3-phenyl-pentanoate.

Example 49

(6S)-3-[2,6-Difluoro-4-(2-phenylethynyl)phenyl]-1,6-dimethyl-6-(3-pyridyl)hexahydropyrimidine-2,4-dione

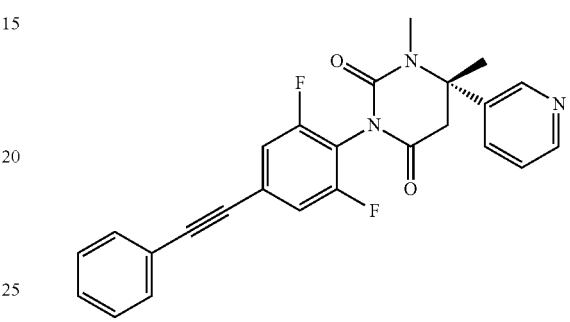

Step 1: (R,E)-2-Methyl-N-[1-(3-pyridyl)ethylidene]propane-2-sulfinamide 1-(Pyridine-3-yl)ethanone (10 g, 82.6 mmol) was dissolved in 200 ml THF. (R)-2-Methylpropane-2-sulfinamide (CAS 196929-78-9) (10.0 g, 82.6 mmol, 1.0 equiv.) and titanium(IV) ethoxide (37.7 g, 34.2 ml, 165 mmol, 2.0 equiv.) were added and the mixture was stirred for 4 hours at 65° C. The reaction mixture was cooled and saturated NaHCO₃ solution and ethyl acetate were added. The formed suspension was filtered through celite and the filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 100:0 and methanol:dichloromethane 0:100 to 20:80 gradient. The desired (R,E)-2-methyl-N-[1-(3-pyridyl)ethylidene]propane-2-sulfinamide (10.5 g, 57% yield) was obtained as a yellow oil, MS: m/e=225.1 (M+H⁺).

Step 2: Methyl (3S)-3-[[(R)-tert-butylsulfinyl]amino]-3-(3-pyridyl)butanoate Methyl acetate (10.4 g, 11.1 ml, 140 mmol, 3 equiv.) was dissolved in 200 ml dry THF and the solution was cooled to −70° C. LDA (2.0 M in THF/heptane/ethylbenzene) (70.2 ml, 140 mmol, 3 equiv.) was added drop wise at −75° C. to −65° C. and the mixture was stirred for 45 minutes at −70° C. Chlorotitanium triisopropoxide (36.6 g, 140 mmol, 3 equiv.) dissolved in 20 ml of dry THF was added drop wise at −75° C. to −65° C. and the mixture was stirred for 45 minutes at −70° C. (R,E)-2-Methyl-N-[1-(3-pyridyl)ethylidene]propane-2-sulfinamide (Example 49, step 1) (10.5 g, 46.8 mmol) dissolved in 20 ml of dry THF was added drop wise at −75° C. to −65° C. and the mixture was stirred for 1 hour at −70° C. Saturated NaHCO₃ solution was added and the mixture stirred for 10 minutes. Ethyl acetate was added to the formed suspension and the mixture was stirred for 10 minutes. The formed suspension was filtered through celite and the filtrate was extracted twice with ethyl acetate. The organic layers were washed brine, dried over sodium sulfate and evaporated to dryness. The crude product was purified by flash chromatography on a silica gel column eluting with an ethyl acetate:heptane 0:100 to 100:0 gradient. The desired methyl (3S)-3-[[(R)-tert-butylsulfinyl]amino]-3-(3-pyridyl)butanoate (13.6 g, 97% yield) was obtained as a yellow oil, MS: m/e=299.1 (M+H$^+$).

Step 3: Methyl (3S)-3-amino-3-(3-pyridyl)butanoate

Methyl (3S)-3-[[(R)-tert-butylsulfinyl]amino]-3-(3-pyridyl)butanoate (Example 49, step 2) (8.5 g, 22.8 mmol) was dissolved in 35 ml MeOH and HCl (4N in dioxane) (110 ml, 440 mmol, 20 equiv.) was added. The mixture was stirred for 16 hours at room temperature. The reaction mixture was evaporated and extracted with saturated Na$_2$CO$_3$ solution and three times with dichloromethane. The organic layers were combined, dried over sodium sulfate and evaporated to dryness. The crude product was purified by flash chromatography on a silica gel column eluting with a methanol:dichloromethane 0:100 to 85:15 gradient. The desired methyl (3S)-3-amino-3-(3-pyridyl)butanoate (4.1 g, 93% yield) was obtained as a brown oil, MS: m/e=195.1 (M+H$^+$).

Step 4: (6S)-3-[2,6-Difluoro-4-(2-phenylethynyl)phenyl]-1,6-dimethyl-6-(3-pyridyl)hexahydropyrimidine-2,4-dione The title compound was obtained as a light yellow solid, MS: m/e=432.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-(3-pyridyl)butanoate (Example 49, step 3).

Example 50

(6S)-3-[3-Fluoro-5-(2-phenylethynyl)-2-pyridyl]-1,6-dimethyl-6-(3-pyridyl)hexahydropyrimidine-2,4-dione

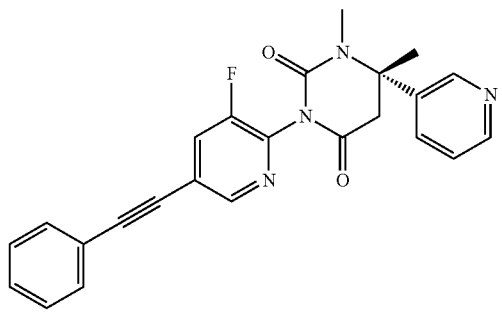 [SMILES: CN1C(=O)N(c2ncc(C#Cc3ccccc3)cc2F)C(=O)C[C@@]1(C)c1cccnc1]

The title compound was obtained as a white solid, MS: m/e=415.2 (M+H$^+$), using chemistry similar to that described in Example 32 starting from 5-bromo-3-fluoropicolinic acid and methyl (3S)-3-amino-3-(3-pyridyl)butanoate (Example 49, step 3).

Example 51

(6RS)-6-(6-Chloro-3-pyridyl)-3-[2,6-difluoro-4-(2-phenylethynyl)phenyl]-1,6-dimethyl-hexahydropyrimidine-2,4-dione

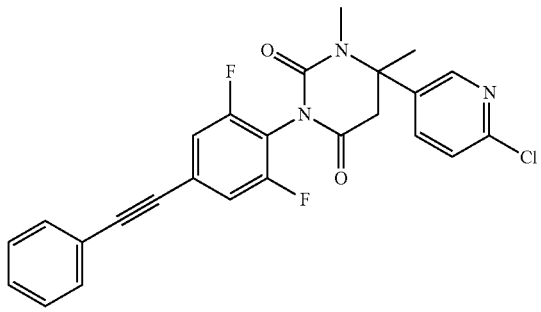 [SMILES: CN1C(=O)N(c2c(F)cc(C#Cc3ccccc3)cc2F)C(=O)CC1(C)c1ccc(Cl)nc1]

Step 1: Methyl (3RS)-3-amino-3-(6-chloro-3-pyridyl)butanoate

The title compound was obtained as a light brown oil, MS: m/e=229.1 (M+H$^+$), using chemistry similar to that described in Example 39, steps 1, 2 and 3 starting from 1-(6-chloropyridin-3-yl)ethanone.

Step 2: (6RS)-6-(6-Chloro-3-pyridyl)-3-[2,6-difluoro-4-(2-phenylethynyl)phenyl]-1,6-dimethyl-hexahydropyrimidine-2,4-dione The title compound was obtained as a white solid, MS: m/e=466.1/468.1 (M+H$^+$), using chemistry similar to that described in Example 5, step 1, Example 1, step 3 and step 4 starting from 2,6-difluoro-4-phenylethynyl-phenylamine (Example 1, step 1) and methyl (3RS)-3-amino-3-(6-chloro-3-pyridyl)butanoate (Example 51, step 1).

Example 52

(6S)-3-[2,6-Difluoro-4-(2-phenylethynyl)phenyl]-1-ethyl-6-methyl-6-(3-pyridyl)hexahydropyrimidine-2,4-dione

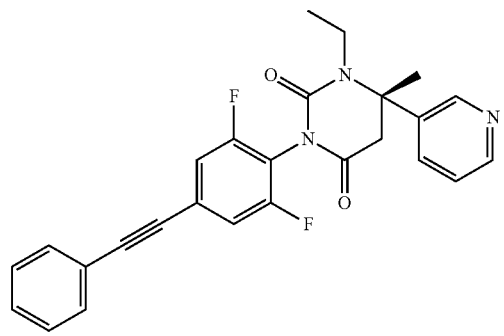 [SMILES: CCN1C(=O)N(c2c(F)cc(C#Cc3ccccc3)cc2F)C(=O)C[C@@]1(C)c1cccnc1]

The title compound was obtained as a light brown solid, MS: m/e=446.2 (M+H$^+$), using chemistry similar to that described in Example 5, step 1, Example 1, step 3 and step 4 by using iodoethane instead of iodomethane starting from 2,6-difluoro-4-phenylethynyl-phenylamine (Example 1, step 1) and methyl (3S)-3-amino-3-(3-pyridyl)butanoate (Example 49, step 3).

Example 53

(6S)-3-[2,6-Difluoro-4-[2-(3-pyridyl)ethynyl]phenyl]-1,6-dimethyl-6-(3-pyridyl)hexahydropyrimidine-2,4-dione

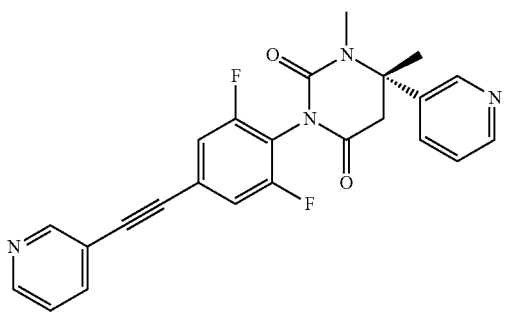 [SMILES: CN1C(=O)N(c2c(F)cc(C#Cc3cccnc3)cc2F)C(=O)C[C@@]1(C)c1cccnc1]

Step 1: (6S)-3-(2,6-Difluoro-4-odo-phenyl)-1,6-dimethyl-6-(3-pyridy)hexahydropyrimidine-2,4-dione The title compound was obtained as a yellow solid, MS: m/e=458.2 (M+H$^+$), using chemistry similar to that described in Example 5, step 1, Example 1, step 3 and step 4 starting from 2,6-difluoro-4-iodo-phenylamine and methyl (3S)-3-amino-3-(3-pyridyl)butanoate (Example 49, step 3).

Step 2: (6S)-3-[2,6-Difluoro-4-[2-(3-pyridyl)ethynyl]phenyl]-1,6-dimethyl-6-(3-pyridyl)hexahydropyrimidine-2,4-dione The title compound was obtained as a light yellow solid, MS: m/e=433.2 (M+H$^+$), using chemistry similar to that described in Example 1, steps 1 starting from (6S)-3-(2,6-difluoro-4-iodo-phenyl)-1,6-dimethyl-6-(3-pyridyl)hexahydropyrimidine-2,4-dione (Example 53, step 1) and 3-ethynylpyridine.

Example 54

(6S)-3-[2,6-Difluoro-4-(2-phenylethynyl)phenyl]-1,6-dimethyl-6-(6-methyl-3-pyridyl)hexahydropyrimidine-2,4-dione

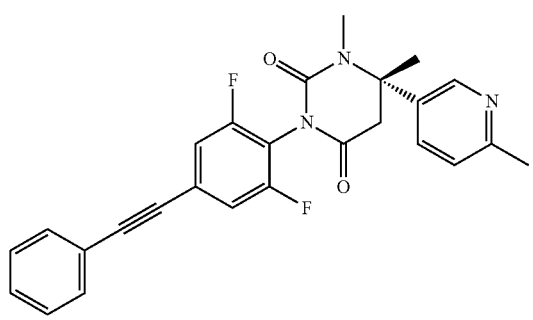 [SMILES: Cc1ccc([C@]2(C)CC(=O)N(c3c(F)cc(C#Cc4ccccc4)cc3F)C(=O)N2C)cn1]

Step 1: Methyl (3S)-3-amino-3-(6-methyl-3-pyridyl)butanoate

The title compound was obtained as a light brown oil, MS: m/e=209.2 (M+H$^+$), using chemistry similar to that described in Example 49, steps 1, 2 and 3 starting from 1-(6-methylpyridin-3-yl)ethanone.

Step 2: (6S)-3-[2,6-Difluoro-4-(2-phenylethynyl)phenyl]-1,6-dimethyl-6-(6-methyl-3-pyridyl)hexahydropyrimidine-2,4-dione The title compound was obtained as a yellow solid, MS: m/e=446.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-(6-methyl-3-pyridyl)butanoate (Example 54, step 1).

Example 55

(6S)-3-[2,6-Difluoro-4-(2-phenylethynyl)phenyl]-1,6-dimethyl-6-pyrimidin-4-yl-hexahydropyrimidine-2,4-dione

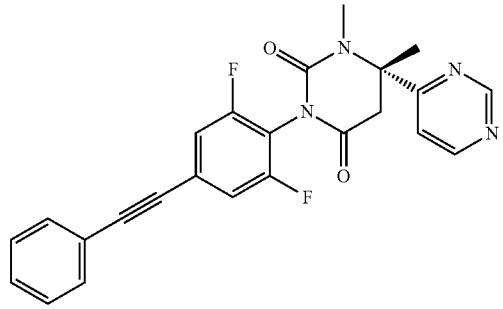

Step 1: Methyl (3S)-3-amino-3-pyrimidin-4-yl-butanoate

The title compound was obtained as a light yellow oil, MS: m/e=196.1 (M+H$^+$), using chemistry similar to that described in Example 49, steps 1, 2 and 3 starting from 1-pyrimidin-4-ylethanone.

Step 2: (6S)-3-[2,6-Difluoro-4-(2-phenylethynyl)phenyl]-1,6-dimethyl-6-pyrimidin-4-yl-hexahydropyrimidine-2,4-dione The title compound was obtained as a white solid, MS: m/e=433.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-pyrimidin-4-yl-butanoate (Example 55, step 1).

Example 56

(6S)-3-[2,6-Difluoro-4-(2-phenylethynyl)phenyl]-1,6-dimethyl-6-pyrimidin-5-yl-hexahydropyrimidine-2,4-dione

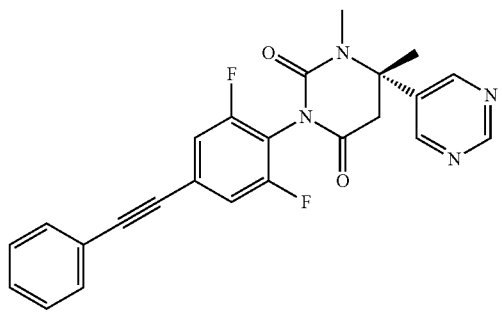

Step 1: Methyl (3S)-3-amino-3-pyrimidin-5-yl-butanoate

The title compound was obtained as a light yellow oil, MS: m/e=196.1 (M+H⁺), using chemistry similar to that described in Example 49, steps 1, 2 and 3 starting from 1-pyrimidin-5-ylethanone.

Step 2: (6S)-3-[2,6-Difluoro-4-(2-phenylethynyl)phenyl]-1,6-dimethyl-6-pyrimidin-5-yl-hexahydropyrimidine-2,4-dione The title compound was obtained as a light yellow oil, MS: m/e=433.2 (M+H⁺), using chemistry similar to that described in Example 5, step 1, Example 1, step 3 and step 4 starting from 2,6-difluoro-4-phenylethynyl-phenylamine (Example 1, step 1) and methyl (3S)-3-amino-3-pyrimidin-5-yl-butanoate (Example 56, step 1).

Example 57

(6S)-3-[2,6-Difluoro-4-(2-phenylethynyl)phenyl]-1,6-dimethyl-6-pyrazin-2-yl-hexahydropyrimidine-2,4-dione

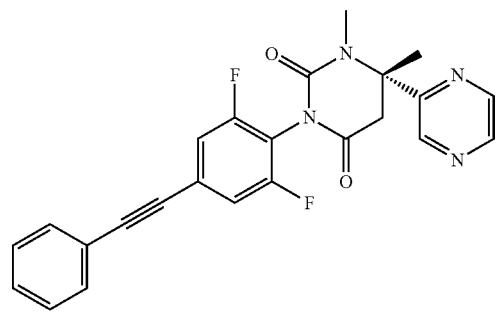 [SMILES: CN1C(=O)N(c2c(F)cc(C#Cc3ccccc3)cc2F)C(=O)C[C@@]1(C)c1cnccn1]

Step 1: Methyl (3S)-3-amino-3-pyrazin-2-yl-butanoate

The title compound was obtained as a light brown semi-solid, MS: m/e=196.1 (M+H⁺), using chemistry similar to that described in Example 49, steps 1, 2 and 3 starting from 1-pyrazin-2-ylethanone.

Step 2: (6S)-3-[2,6-Difluoro-4-(2-phenylethynyl)phenyl]-1,6-dimethyl-6-pyrazin-2-yl-hexahydropyrimidine-2,4-dione The title compound was obtained as a light yellow oil, MS: m/e=433.2 (M+H⁺), using chemistry similar to that described in Example 5, step 1, Example 1, step 3 and step 4 starting from 2,6-difluoro-4-phenylethynyl-phenylamine (Example 1, step 1) and methyl (3S)-3-amino-3-pyrazin-2-yl-butanoate (Example 57, step 1).

Example 58

(6S)-3-[2,6-Difluoro-4-(2-phenylethynyl)phenyl]-1,6-dimethyl-6-pyridazin-3-yl-hexahydropyrimidine-2,4-dione

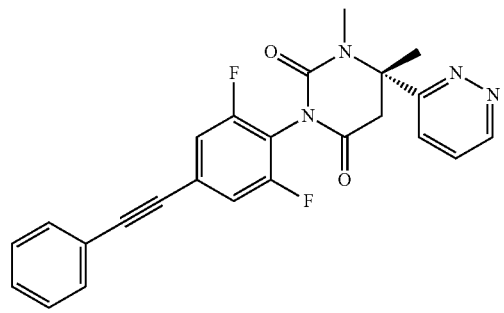 [SMILES: CN1C(=O)N(c2c(F)cc(C#Cc3ccccc3)cc2F)C(=O)C[C@@]1(C)c1cccnn1]

Step 1: Methyl (3S)-3-amino-3-pyridazin-3-yl-butanoate

The title compound was obtained as a dark brown oil, MS: m/e=196.1 (M+H⁺), using chemistry similar to that described in Example 49, steps 1, 2 and 3 starting from 1-(pyridazin-3-yl)ethanone.

Step 2: (6S)-3-[2,6-Difluoro-4-(2-phenylethynyl)phenyl]-1,6-dimethyl-6-pyridazin-3-yl-hexahydropyrimidine-2,4-dione The title compound was obtained as a light yellow solid, MS: m/e=433.2 (M+H⁺), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-pyridazin-3-yl-butanoate (Example 58, step 1).

Example 59

(6S)-3-[2,6-Difluoro-4-(2-phenylethynyl)phenyl]-6-(5-fluoro-3-pyridyl)-1,6-dimethyl-hexahydropyrimidine-2,4-dione

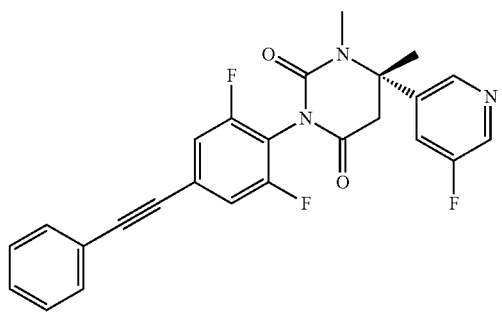 [SMILES: CN1C(=O)N(c2c(F)cc(C#Cc3ccccc3)cc2F)C(=O)C[C@@]1(C)c1cncc(F)c1]

Step 1: Methyl (3S)-3-amino-3-(5-fluoro-3-pyridyl)butanoate

The title compound was obtained as a yellow oil, MS: m/e=213.1 (M+H$^+$), using chemistry similar to that described in Example 49, steps 1, 2 and 3 starting from 1-(5-fluoropyridin-3-yl)ethanone.

Step 2: (6S)-3-[2,6-Difluoro-4-(2-phenylethynyl)phenyl]-6-(5-fluoro-3-pyridyl)-1,6-dimethyl-hexahydropyrimidine-2,4-dione The title compound was obtained as a yellow solid, MS: m/e=450.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-(5-fluoro-3-pyridyl)butanoate (Example 59, step 1).

Example 60

(6S)-6-(2-Chloro-4-pyridyl)-3-[2,6-difluoro-4-(2-phenylethynyl)phenyl]-1,6-dimethyl-hexahydropyrimidine-2,4-dione

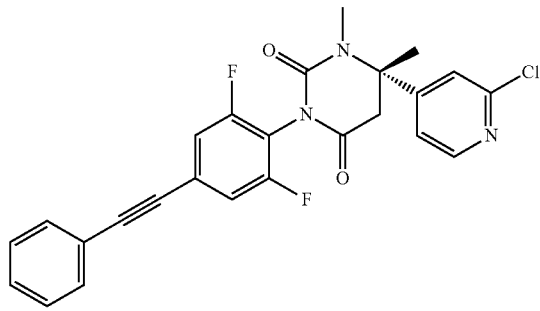 [SMILES: CN1C(=O)N(c2c(F)cc(C#Cc3ccccc3)cc2F)C(=O)C[C@@]1(C)c1ccnc(Cl)c1]

Step 1: Methyl (3S)-3-amino-3-(2-chloro-4-pyridyl)butanoate

The title compound was obtained as a light brown oil, MS: m/e=229.1/231.0 (M+H$^+$), using chemistry similar to that described in Example 49, steps 1, 2 and 3 starting from 1-(2-chloropyridin-4-yl)ethanone.

Step 2: (6S)-6-(2-Chloro-4-pyridyl)-3-[2,6-difluoro-4-(2-phenylethynyl)phenyl]-1,6-dimethyl-hexahydropyrimidine-2,4-dione The title compound was obtained as a white solid, MS: m/e=466.2/468.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-(2-chloro-4-pyridyl)butanoate (Example 60, step 1).

Example 61

(6S)-3-[2,6-Difluoro-4-(2-phenylethynyl)phenyl]-1,6-dimethyl-6-pyridazin-4-yl-hexahydropyrimidine-2,4-dione

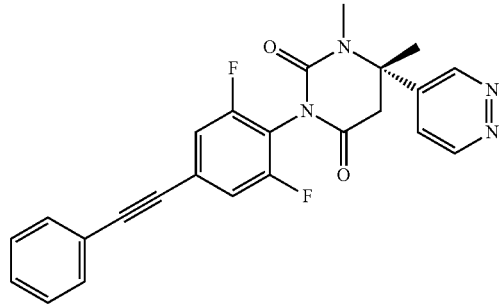 [SMILES: CN1C(=O)N(c2c(F)cc(C#Cc3ccccc3)cc2F)C(=O)C[C@@]1(C)c1ccnnc1]

Step 1: Methyl (3S)-3-amino-3-pyridazin-4-yl-butanoate

The title compound was obtained as a light brown oil, MS: m/e=196.1 (M+H$^+$), using chemistry similar to that described in Example 49, steps 1, 2 and 3 starting from 1-(pyridazin-4-yl)ethanone.

Step 2: (6S)-3-[2,6-Difluoro-4-(2-phenylethynyl)phenyl]-1,6-dimethyl-6-pyridazin-4-yl-hexahydropyrimidine-2,4-dione The title compound was obtained as a brown solid, MS: m/e=433.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-pyridazin-4-yl-butanoate (Example 61, step 1).

Example 62

(6S)-3-[2,6-Difluoro-4-(2-phenylethynyl)phenyl]-1,6-dimethyl-6-(2-methyl-4-pyridyl)hexahydropyrimidine-2,4-dione

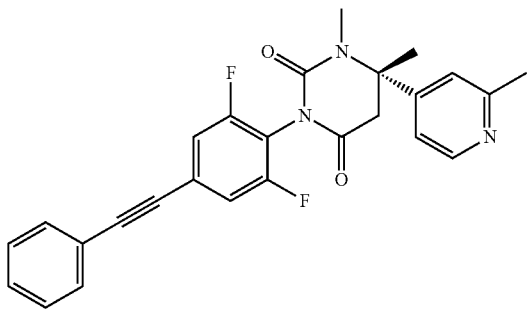 [SMILES: Cc1cc([C@]2(C)CC(=O)N(c3c(F)cc(C#Cc4ccccc4)cc3F)C(=O)N2C)ccn1]

Step 1: Methyl (3S)-3-amino-3-(2-methyl-4-pyridyl)butanoate

The title compound was obtained as a light yellow oil, MS: m/e=209.2 (M+H$^+$), using chemistry similar to that described in Example 49, steps 1, 2 and 3 starting from 1-(2-methylpyridin-4-yl)ethanone.

Step 2: (6S)-3-[2,6-Difluoro-4-(2-phenylethynyl)phenyl]-1,6-dimethyl-6-(2-methyl-4-pyridyl)hexahydropyrimidine-2,4-dione The title compound was obtained as a white solid, MS: m/e=446.2 (M+H$^+$), using chemistry similar to that described in Example 5, step 1, Example 1, step 3 and step 4 starting from 2,6-difluoro-4-phenylethynyl-phenylamine (Example 1, step 1) and methyl (3S)-3-amino-3-(2-methyl-4-pyridyl)butanoate (Example 62, step 1).

Example 63

(6S)-3-[2,6-Difluoro-4-(2-phenylethynyl)phenyl]-6-(6-methoxy-3-pyridyl)-1,6-dimethyl-hexahydropyrimidine-2,4-dione

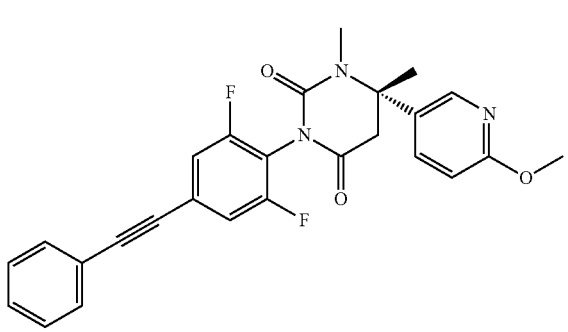 [SMILES: COc1ccc([C@]2(C)CC(=O)N(c3c(F)cc(C#Cc4ccccc4)cc3F)C(=O)N2C)cn1]

Step 1: Methyl (3S)-3-amino-3-(6-methoxy-3-pyridyl)butanoate

The title compound was obtained as a light yellow oil, MS: m/e=225.1 (M+H$^+$), using chemistry similar to that described in Example 49, steps 1, 2 and 3 starting from 1-(6-methoxypyridin-3-yl)ethanone.

Step 2: (6S)-3-[2,6-Difluoro-4-(2-phenylethynyl)phenyl]-6-(6-methoxy-3-pyridyl)-1,6-dimethyl-hexahydropyrimidine-2,4-dione The title compound was obtained as a light yellow solid, MS: m/e=462.2 (M+H$^+$), using chemistry similar to that described in Example 1, step 2, step 3 and step 4 starting from 2,6-difluoro-4-phenylethynyl-phenylamine (Example 1, step 1) and methyl (3S)-3-amino-3-(6-methoxy-3-pyridyl)butanoate (Example 63, step 1).

Example 64

(6S)-6-(2-Chloro-4-pyridyl)-3-[2,6-difluoro-4-[2-(3-pyridyl)ethynyl]phenyl]-1,6-dimethyl-hexahydropyrimidine-2,4-dione

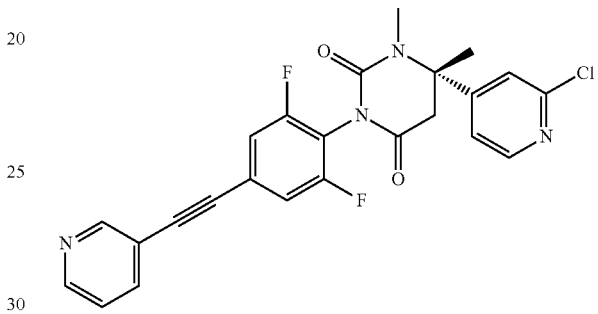

The title compound was obtained as an orange solid, MS: m/e=467.1/469.1 (M+H$^+$), using chemistry similar to that described in Example 5, step 1, Example 1, step 3 and step 4 starting from 2,6-difluoro-4-[2-(3-pyridyl)ethynyl]aniline (Example 15, step 1) and methyl (3S)-3-amino-3-(2-chloro-4-pyridyl)butanoate (Example 60, step 1).

Example 65

(6S)-3-[2,6-Difluoro-4-(2-phenylethynyl)phenyl]-1,6-dimethyl-6-(6-oxo-1H-pyridin-3-yl)hexahydropyrimidine-2,4-dione

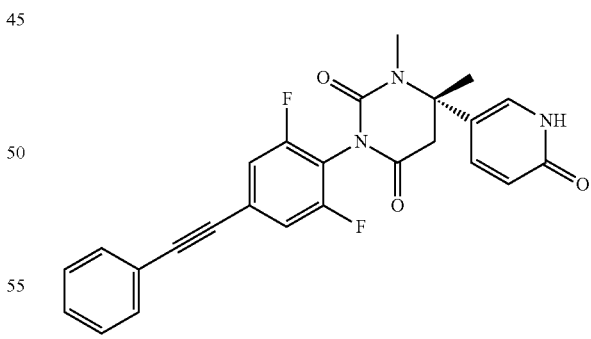

(6S)-3-[2,6-Difluoro-4-(2-phenylethynyl)phenyl]-6-(6-methoxy-3-pyridyl)-1,6-dimethyl-hexahydropyrimidine-2,4-dione (Example 63) (65 mg, 0.14 mmol) was dissolved in chloroform (1.0 ml) and BBr$_3$ (1M in dichloromethane) (170 ul, 0.17 mmol, 1.2 equiv.) was added at room temperature. The mixture was stirred for 6 hours at 60° C. The reaction mixture was cooled and extracted with saturated NaHCO$_3$ solution. The aqueous layer was extracted with dichloromethane. The organic layers were loaded directly onto a silica gel column. The crude product was purified by flash chromatography eluting with a methanol:dichloromethane 0:100 to 10:90 gradient. The desired (6S)-3-[2,6-difluoro-4-(2-phenylethynyl)phenyl]-1,6-dimethyl-6-(6-oxo-1H-pyridin-3-yl)hexahydropyrimidine-2,4-dione (41 mg, 65% yield) was obtained as a white solid, MS: m/e=448.2 (M+H$^+$).

Example 66

(6S)-3-[2,6-Difluoro-4-(2-phenylethynyl)phenyl]-1,6-dimethyl-6-(1-methyl-6-oxo-3-pyridyl)hexahydropyrimidine-2,4-dione

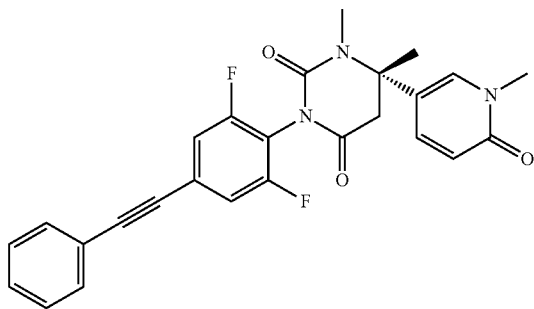 [SMILES: CN1C(=O)N(c2c(F)cc(C#Cc3ccccc3)cc2F)C(=O)C[C@@]1(C)c1ccc(=O)n(C)c1]

(40 mg, 0.089 mmol) (6S)-3-[2,6-Difluoro-4-(2-phenylethynyl)phenyl]-1,6-dimethyl-6-(6-oxo-1H-pyridin-3-yl)hexahydropyrimidine-2,4-dione (Example 65) was dissolved in DMF (1 ml) and potassium carbonate (37 mg, 0.268 mmol, 3 equiv.), tetrabutylammonium iodide (3.3 mg, 0.009 mmol, 0.1 equiv.) and iodomethane (25 mg, 11 ul, 0.18 mmol, 2 equiv.) were added at room temperature. The mixture was stirred for 16 hours at 40° C. The reaction mixture was evaporated with isolute®. The crude product was purified by flash chromatography on a silica gel column eluting with a methanol:dichloromethane 0:100 to 10:90 gradient. The desired (6S)-3-[2,6-difluoro-4-(2-phenylethynyl)phenyl]-1,6-dimethyl-6-(1-methyl-6-oxo-3-pyridyl)hexahydropyrimidine-2,4-dione (35 mg, 85% yield) was obtained as a colorless oil, MS: m/e=462.2 (M+H$^+$).

Example 67

(6S)-3-[2,6-Difluoro-4-(2-phenylethynyl)phenyl]-6-(1-ethyl-6-oxo-3-pyridyl)-1,6-dimethyl-hexahydropyrimidine-2,4-dione

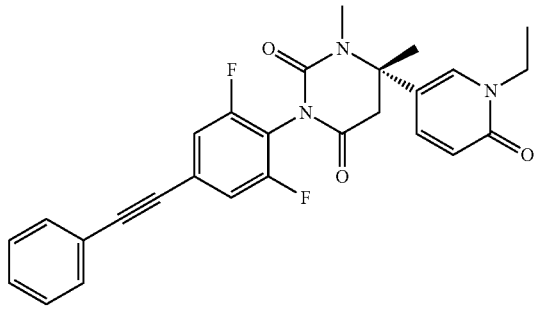

The title compound was obtained as a light yellow solid, MS: m/e=476.4 (M+H$^+$), using chemistry similar to that described in Example 66 by using iodoethane instead of iodomethane starting from (6S)-3-[2,6-difluoro-4-(2-phenylethynyl)phenyl]-1,6-dimethyl-6-(6-oxo-1H-pyridin-3-yl)hexahydropyrimidine-2,4-dione (Example 65).

Example 68

(6S)-3-[2,6-Difluoro-4-(2-phenylethynyl)phenyl]-6-(1-isopropyl-6-oxo-3-pyridyl)-1,6-dimethyl-hexahydropyrimidine-2,4-dione

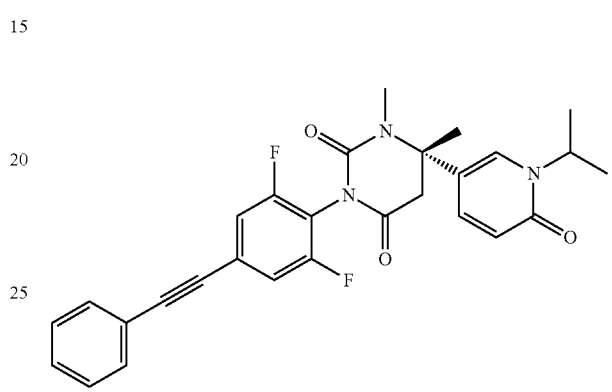

The title compound was obtained as a light yellow solid, MS: m/e=490.3 (M+H$^+$), using chemistry similar to that described in Example 66 by using 2-iodopropane instead of iodomethane starting from (6S)-3-[2,6-difluoro-4-(2-phenylethynyl)phenyl]-1,6-dimethyl-6-(6-oxo-1H-pyridin-3-yl)hexahydropyrimidine-2,4-dione (Example 65).

Example 69

(6S)-3-[2,6-Difluoro-4-(2-phenylethynyl)phenyl]-6-(6-isopropoxy-3-pyridyl)-1,6-dimethyl-hexahydropyrimidine-2,4-dione

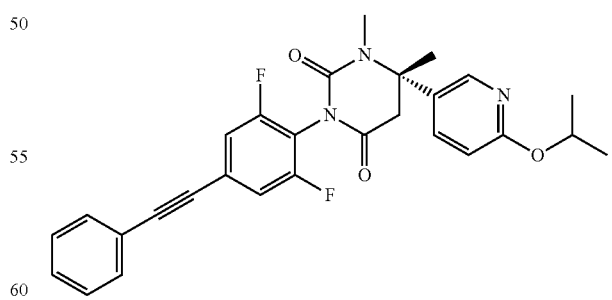

The title compound was obtained as a light yellow semi-solid, MS: m/e=490.4 (M+H$^+$), formed as a byproduct in Example 68.

Example 70

(6S)-3-[2,6-Difluoro-4-(2-phenylethynyl)phenyl]-1-isopropyl-6-methyl-6-(3-pyridyl)hexahydropyrimidine-2,4-dione

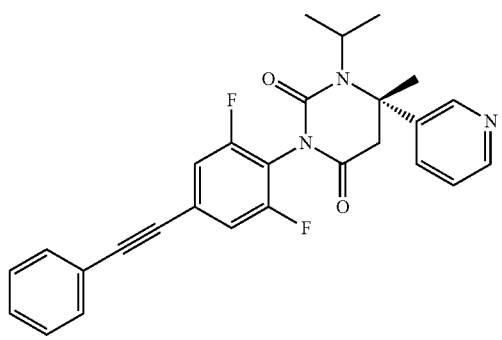 [SMILES: CC(C)N1C(=O)N(c2c(F)cc(C#Cc3ccccc3)cc2F)C(=O)C[C@@]1(C)c1cccnc1]

Step 1: Methyl (3S)-3-(isopropylamino)-3-(3-pyridyl)butanoate

Methyl (3S)-3-amino-3-(3-pyridyl)butanoate (Example 49, step 3) (200 mg, 1.03 mmol) was dissolved in dichloromethane (2.0 ml) and trifluoroacetic acid (0.16 ml, 2.06 mmol, 2.0 equiv.), acetone (0.23 ml, 3.09 mmol, 3 equiv.) and tetramethylammonium triacetoxyborohydride (406 mg, 1.54 mmol, 1.5 equiv.) were added at room temperature. The mixture was stirred for 16 hour at 45° C. The reaction mixture was extracted with saturated NaHCO₃ solution and twice with dichloromethane. The organic layers were combined and evaporated to dryness. The crude product was purified by flash chromatography on a silica gel column eluting with a methanol:ethyl acetate gradient 0:100 to 10:90. The desired methyl (3S)-3-(isopropylamino)-3-(3-pyridyl)butanoate (117 mg, 48% yield) was obtained as a light yellow liquid, MS: m/e=237.2 (M+H$^+$).

Step 2: (6S)-3-[2,6-Difluoro-4-(2-phenylethynyl)phenyl]-1-isopropyl-6-methyl-6-(3-pyridyl)hexahydropyrimidine-2,4-dione The title compound was obtained as a light yellow oil, MS: m/e=460.3 (M+H$^+$), using chemistry similar to that described in Example 1, step 2 by using DMF instead of toluene starting from 2,6-difluoro-4-phenylethynyl-phenylamine (Example 1, step 1) and methyl (3S)-3-(isopropylamino)-3-(3-pyridyl)butanoate (Example 70, step 1).

Example 71

(6S)-3-[2-Chloro-6-fluoro-4-(2-phenylethynyl)phenyl]-1,6-dimethyl-6-(3-pyridyl)hexahydropyrimidine-2,4-dione

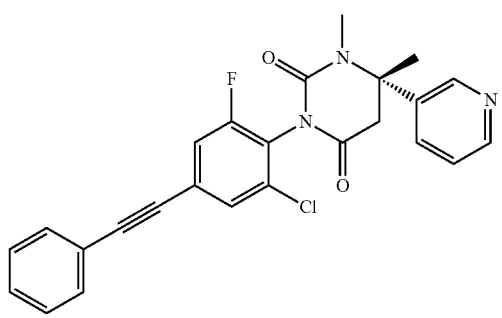

Step 1: (6S)-3-(4-Bromo-2-chloro-6-fluoro-phenyl)-1,6-dimethyl-6-(3-pyridyl)hexahydropyrimidine-2,4-dione The title compound was obtained as a white solid, MS: m/e=426.1/428.1 (M+H$^+$), using chemistry similar to that described in Example 1, step 2, step 3 and step 4 by using DMF instead of toluene in step 2 starting from 4-bromo-2-chloro-6-fluoro-aniline and methyl (3S)-3-amino-3-(3-pyridyl)butanoate (Example 49, step 3).

Step 2: (6S)-3-[2-Chloro-6-fluoro-4-(2-phenylethynyl)phenyl]-1,6-dimethyl-6-(3-pyridyl)hexahydropyrimidine-2,4-dione The title compound was obtained as a yellow solid, MS: m/e=448.2/450.2 (M+H$^+$), using chemistry similar to that described in Example 1, steps 1 starting from (6S)-3-(4-bromo-2-chloro-6-fluoro-phenyl)-1,6-dimethyl-6-(3-pyridyl)hexahydropyrimidine-2,4-dione (Example 71, step 1) and phenylacetylene.

Example 72

(6RS)-3-[2,6-Difluoro-4-[2-(3-pyridyl)ethynyl]phenyl]-1-methyl-6-phenyl-6-(trifluoromethyl)hexahydropyrimidine-2,4-dione

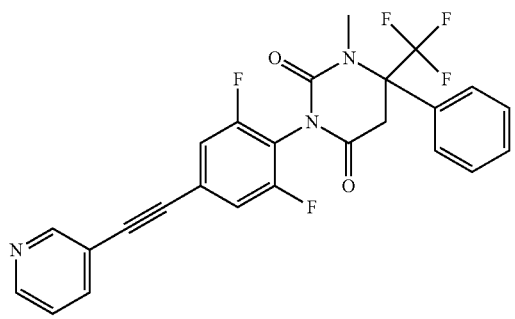 [SMILES: CN1C(=O)N(c2c(F)cc(C#Cc3cccnc3)cc2F)C(=O)CC1(c1ccccc1)C(F)(F)F]

Step 1: Methyl (3RS)-3-amino-4,4,4-trifluoro-3-phenyl-butanoate

The title compound was obtained as a light yellow liquid, MS: m/e=262.2 (M+H$^+$), using chemistry similar to that described in Example 39, steps 1, 2 and 3 starting from 2,2,2-trifluoro-1-phenylethanone.

Step 2: (6RS)-3-[2,6-Difluoro-4-[2-(3-pyridyl)ethynyl]phenyl]-1-methyl-6-phenyl-6-(trifluoromethyl)hexahydropyrimidine-2,4-dione The title compound was obtained as a light red solid, MS: m/e=486.3 (M+H$^+$), using chemistry similar to that described in Example 5, step 1, Example 1, step 3 and step 4 starting from 2,6-difluoro-4-[2-(3-pyridyl)ethynyl]aniline (Example 15, step 1) and methyl (3RS)-3-amino-4,4,4-trifluoro-3-phenyl-butanoate (Example 72, step 1).

Example 73

(6S)-3-[2,6-Difluoro-4-(2-phenylethynyl)phenyl]-6-(2-methoxy-4-pyridyl)-1,6-dimethyl-hexahydropyrimidine-2,4-dione

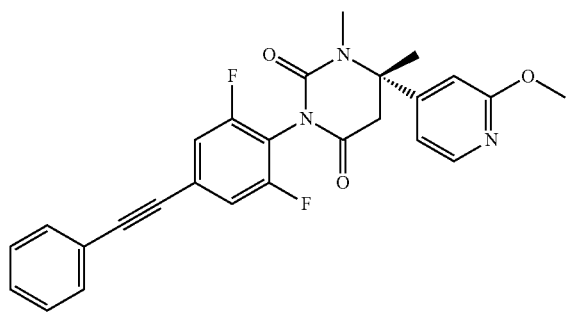 [SMILES: COc1cc([C@]2(C)CC(=O)N(c3c(F)cc(C#Cc4ccccc4)cc3F)C(=O)N2C)ccn1]

Step 1: Methyl (3S)-3-amino-3-(2-methoxy-4-pyridyl)butanoate

The title compound was obtained as a light yellow oil, MS: m/e=225.2 (M+H$^+$), using chemistry similar to that described in Example 49, steps 1, 2 and 3 starting from 1-(2-methoxypyridin-4-yl)ethanone (CAS 764708-20-5).

Step 2: (6S)-3-[2,6-Difluoro-4-(2-phenylethynyl)phenyl]-6-(2-methoxy-4-pyridyl)-1,6-dimethyl-hexahydropyrimidine-2,4-dione The title compound was obtained as a white solid, MS: m/e=462.3 (M+H$^+$), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(2-methoxy-4-pyridyl)butanoate (Example 73, step 1).

Example 74

(6S)-3-[2,6-Difluoro-4-(2-phenylethynyl)phenyl]-1,6-dimethyl-6-(2-oxo-1H-pyridin-4-yl)hexahydropyrimidine-2,4-dione

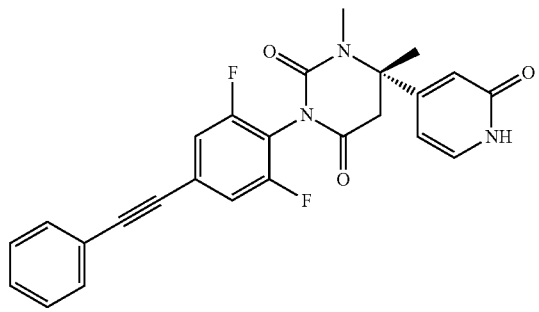 [SMILES: CN1C(=O)N(c2c(F)cc(C#Cc3ccccc3)cc2F)C(=O)C[C@@]1(C)c1cc[nH]c(=O)c1]

The title compound was obtained as a white solid, MS: m/e=448.3 (M+H$^+$), using chemistry similar to that described in Example 65 starting from (6S)-3-[2,6-difluoro-4-(2-phenylethynyl)phenyl]-6-(2-methoxy-4-pyridyl)-1,6-dimethyl-hexahydropyrimidine-2,4-dione (Example 73).

Example 75

(6S)-3-[2,6-Difluoro-4-(2-phenylethynyl)phenyl]-1,6-dimethyl-6-(1-methyl-2-oxo-4-pyridyl)hexahydropyrimidine-2,4-dione

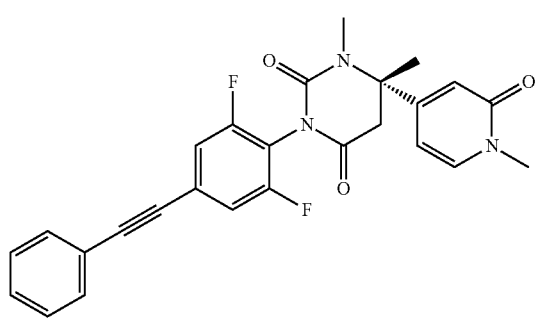 [SMILES: CN1C(=O)N(c2c(F)cc(C#Cc3ccccc3)cc2F)C(=O)C[C@@]1(C)c1ccn(C)c(=O)c1]

The title compound was obtained as a white solid, MS: m/e=462.2 (M+H$^+$), using chemistry similar to that described in Example 66 starting from (6S)-3-[2,6-difluoro-4-(2-phenylethynyl)phenyl]-1,6-dimethyl-6-(2-oxo-1H-pyridin-4-yl)hexahydropyrimidine-2,4-dione (Example 74).

Example 76

(6S)-3-[2,6-Difluoro-4-(2-phenylethynyl)phenyl]-1,6-dimethyl-6-(2-methylpyrimidin-4-yl)hexahydropyrimidine-2,4-dione

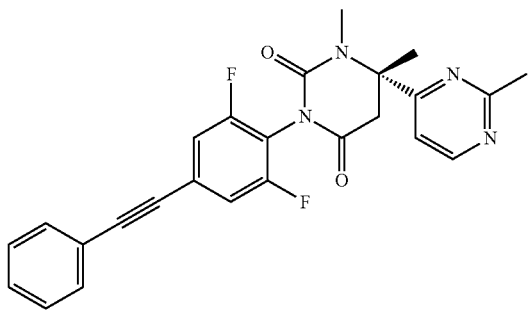 [SMILES: Cc1nccc([C@]2(C)CC(=O)N(c3c(F)cc(C#Cc4ccccc4)cc3F)C(=O)N2C)n1]

Step 1: Methyl (3S)-3-amino-3-(2-methylpyrimidin-4-yl)butanoate

The title compound was obtained as a light yellow oil, MS: m/e=210.1 (M+H$^+$), using chemistry similar to that described in Example 49, steps 1, 2 and 3 starting from 1-(2-methylpyrimidin-4-yl)ethanone.

Step 2: (6S)-3-[2,6-Difluoro-4-(2-phenylethynyl)phenyl]-1,6-dimethyl-6-(2-methylpyrimidin-4-yl)hexahydropyrimidine-2,4-dione The title compound was obtained as a white foam, MS: m/e=447.2 (M+H$^+$), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(2-methylpyrimidin-4-yl)butanoate (Example 76, step 1).

Example 77

(6S)-3-[2,6-Difluoro-4-(2-phenylethynyl)phenyl]-1-ethyl-6-methyl-6-(2-methyl-4-pyridyl)hexahydropyrimidine-2,4-dione

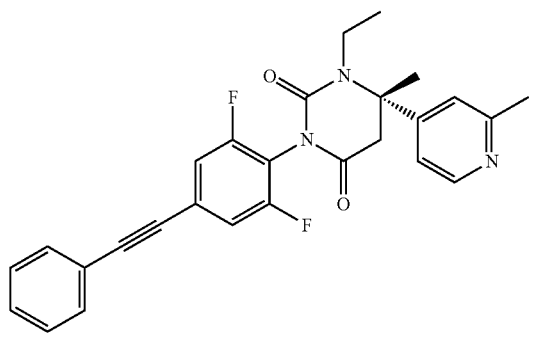 [SMILES: CCN1C(=O)N(c2c(F)cc(C#Cc3ccccc3)cc2F)C(=O)C[C@@]1(C)c1ccnc(C)c1]

The title compound was obtained as a white solid, MS: m/e=460.3 (M+H$^+$), using chemistry similar to that described in Example 5, step 1, Example 1, step 3 and step 4 by using iodoethane instead of iodomethane in the last step starting from 2,6-difluoro-4-phenylethynyl-phenylamine (Example 1, step 1) and methyl (3S)-3-amino-3-(2-methyl-4-pyridyl)butanoate (Example 62, step 1).

Example 78

(6S)-3-[2,6-Difluoro-4-(2-phenylethynyl)phenyl]-1,6-dimethyl-6-(4-pyridyl)hexahydropyrimidine-2,4-dione

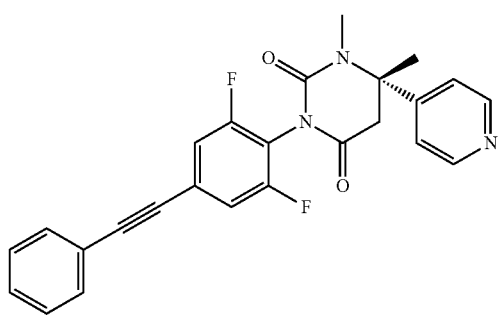 [SMILES: CN1C(=O)N(c2c(F)cc(C#Cc3ccccc3)cc2F)C(=O)C[C@@]1(C)c1ccncc1]

Step 1: Methyl (3S)-3-amino-3-(4-pyridyl)butanoate

The title compound was obtained as a yellow liquid, MS: m/e=195.1 (M+H$^+$), using chemistry similar to that described in Example 49, steps 1, 2 and 3 starting from 1-(pyridin-4-yl)ethanone.

Step 2: (6S)-3-[2,6-Difluoro-4-(2-phenylethynyl)phenyl]-1,6-dimethyl-6-(4-pyridyl)hexahydropyrimidine-2,4-dione The title compound was obtained as a white solid, MS: m/e=432.2 (M+H$^+$), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(4-pyridyl)butanoate (Example 78, step 1).

Example 79

(6S)-3-[2,6-Difluoro-4-(2-phenylethynyl)phenyl]-6-(2-methoxypyrimidin-5-yl)-1,6-dimethyl-hexahydropyrimidine-2,4-dione

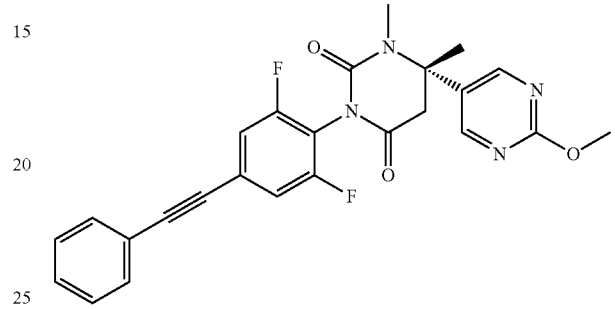

Step 1: Methyl (3S)-3-amino-3-(2-methoxypyrimidin-5-yl)butanoate

The title compound was obtained as a yellow oil, MS: m/e=226.1 (M+H$^+$), using chemistry similar to that described in Example 49, steps 1, 2 and 3 starting from 1-(2-methoxypyrimidin-5-yl)ethanone.

Step 2: (6S)-3-[2,6-Difluoro-4-(2-phenylethynyl)phenyl]-6-(2-methoxypyrimidin-5-yl)-1,6-dimethyl-hexahydropyrimidine-2,4-dione The title compound was obtained as a colorless oil, MS: m/e=463.3 (M+H$^+$), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(2-methoxypyrimidin-5-yl)butanoate (Example 79, step 1).

Example 80

(6S)-3-[2,6-Difluoro-4-(2-phenylethynyl)phenyl]-1,6-dimethyl-6-(2-oxo-1H-pyrimidin-5-yl)hexahydropyrimidine-2,4-dione

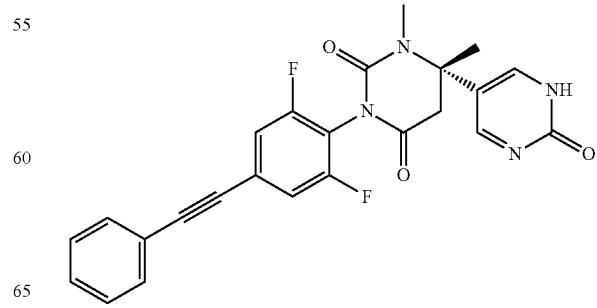

The title compound was obtained as a yellow solid, MS: m/e=449.2 (M+H⁺), using chemistry similar to that described in Example 65 starting from (6S)-3-[2,6-difluoro-4-(2-phenylethynyl)phenyl]-6-(2-methoxypyrimidin-5-yl)-1,6-dimethyl-hexahydropyrimidine-2,4-dione (Example 79).

Example 81

(6S)-3-[2,6-Difluoro-4-(2-phenylethynyl)phenyl]-6-(6-methoxypyridazin-3-yl)-1,6-dimethyl-hexahydropyrimidine-2,4-dione

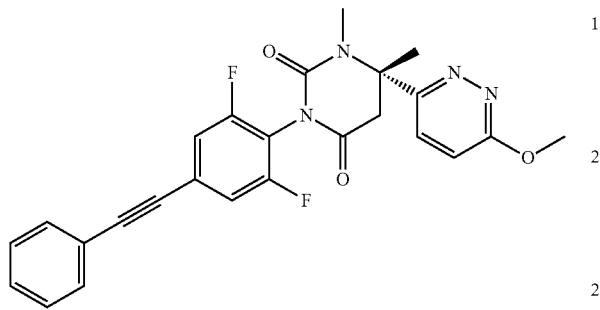

Step 1: Methyl (3S)-3-amino-3-(6-methoxypyridazin-3-yl)butanoate

The title compound was obtained as a light brown oil, MS: m/e=226.1 (M+H⁺), using chemistry similar to that described in Example 49, steps 1, 2 and 3 starting from 1-(6-methoxypyridazin-3-yl)ethanone (CAS 19194-98-0).

Step 2: (6S)-3-[2,6-Difluoro-4-(2-phenylethynyl)phenyl]-6-(6-methoxypyridazin-3-yl)-1,6-dimethyl-hexahydropyrimidine-2,4-dione The title compound was obtained as a white solid, MS: m/e=463.3 (M+H⁺), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(6-methoxypyridazin-3-yl)butanoate (Example 81, step 1).

Example 82

(6S)-3-[2,6-Difluoro-4-(2-phenylethynyl)phenyl]-1,6-dimethyl-6-(6-oxo-1H-pyridazin-3-yl)hexahydropyrimidine-2,4-dione

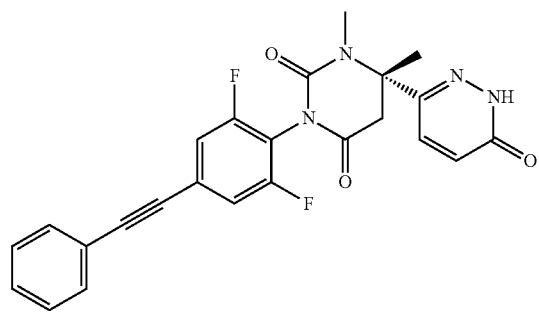 [SMILES: CN1C(=O)N(c2c(F)cc(C#Cc3ccccc3)cc2F)C(=O)C[C@@]1(C)c1ccc(=O)[nH]n1]

The title compound was obtained as a white solid, MS: m/e=449.3 (M+H⁺), using chemistry similar to that described in Example 65 starting from (6S)-3-[2,6-difluoro-4-(2-phenylethynyl)phenyl]-6-(6-methoxypyridazin-3-yl)-1,6-dimethyl-hexahydropyrimidine-2,4-dione (Example 81).

Example 83

(6S)-3-[2,6-Difluoro-4-(2-phenylethynyl)phenyl]-1,6-dimethyl-6-(1-methyl-6-oxo-pyridazin-3-yl)hexahydropyrimidine-2,4-dione

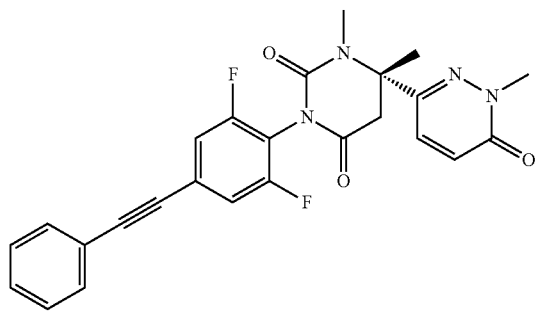 [SMILES: CN1C(=O)N(c2c(F)cc(C#Cc3ccccc3)cc2F)C(=O)C[C@@]1(C)c1ccc(=O)n(C)n1]

The title compound was obtained as a colorless oil, MS: m/e=463.3 (M+H⁺), using chemistry similar to that described in Example 66 starting from (6S)-3-[2,6-difluoro-4-(2-phenylethynyl)phenyl]-1,6-dimethyl-6-(6-oxo-1H-pyridazin-3-yl)hexahydropyrimidine-2,4-dione (Example 82).

Example 84

(6S)-3-[2,6-Difluoro-4-(2-phenylethynyl)phenyl]-1,6-dimethyl-6-(1-methylpyrrolo[2,3-b]pyridin-5-yl)hexahydropyrimidine-2,4-dione

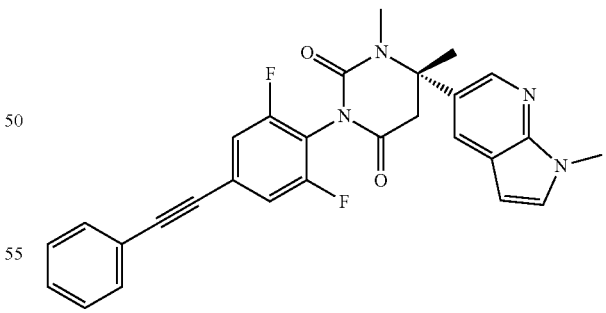

Step 1: 1-(1-Methylpyrrolo[2,3-b]pyridin-5-yl)ethanone

The title compound was obtained as a yellow oil, MS: m/e=175.1 (M+H⁺), using chemistry similar to that described in Example 1, step 3 from 1-(1H-pyrrolo[2,3-b]pyridin-5-yl)ethanone (CAS 83393-46-8).

Step 2: Methyl (3S)-3-amino-3-(1-methylpyrrolo[2,3-b]pyridin-5-yl)butanoate

The title compound was obtained as a yellow oil, MS: m/e=249.2 (M+H⁺), using chemistry similar to that described in Example 49, steps 1, 2 and 3 starting from 1-(1-methylpyrrolo[2,3-b]pyridin-5-yl)ethanone (Example 84, step 1).

Step 3: (6S)-3-[2,6-Di fluoro-4-(2-phenylethynyl)phenyl]-1,6-dimethyl-6-(1-methylpyrrolo [2,3-b]pyridin-5-yl)hexahydropyrimidine-2,4-dione The title compound was obtained as a light yellow solid, MS: m/e=485.3 (M+H⁺), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-(1-methylpyrrolo[2,3-b]pyridin-5-yl)butanoate (Example 84, step 2).

Example 85

(6S)-3-[2,6-Difluoro-4-(2-phenylethynyl)phenyl]-6-imidazo[1,2-b]pyridazin-6-yl-1,6-dimethyl-hexahydropyrimidine-2,4-dione

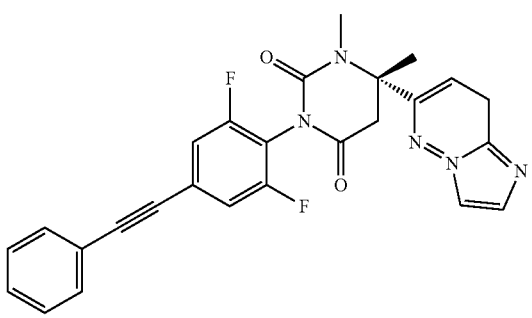

Step 1: Methyl (3S)-3-amino-3-imidazo[1,2-b]pyridazin-6-yl-butanoate

The title compound was obtained as a dark blue oil, MS: m/e=235.2 (M+H⁺), using chemistry similar to that described in Example 49, steps 1, 2 and 3 starting from 1-(imidazo[1,2-b]pyridazin-6-yl)ethanone (CAS 1378816-95-5).

Step 2: (6S)-3-[2,6-Difluoro-4-(2-phenylethynyl)phenyl]-6-imidazo[1,2-b]pyridazin-6-yl-1,6-dimethyl-hexahydropyrimidine-2,4-dione The title compound was obtained as a colorless oil, MS: m/e=472.3 (M+H⁺), using chemistry similar to that described in Example 1, step 2, step 3 and step 4 by using DMF instead of toluene in step 2 starting from 2,6-difluoro-4-phenylethynyl-phenylamine (Example 1, step 1) and methyl (3S)-3-amino-3-imidazo[1,2-b]pyridazin-6-yl-butanoate (Example 85, step 1).

Example 86

(9aRS)-7-[2-Chloro-6-fluoro-4-(2-phenylethynyl)phenyl]-9a-methyl-2,3,4,9-tetrahydropyrazino[1,2-c]pyrimidine-1,6,8-trione

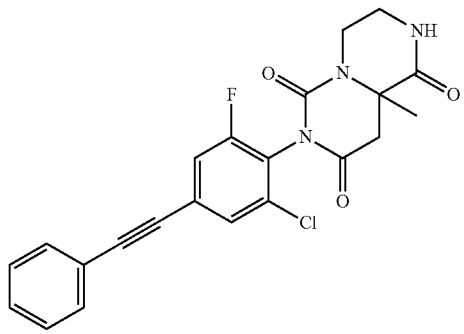 [SMILES: CC12CC(=O)N(c3c(F)cc(C#Cc4ccccc4)cc3Cl)C(=O)N1CCNC2=O]

Step 1: 2-Chloro-6-fluoro-4-(2-phenylethynyl)aniline

The title compound was obtained as an orange oil, MS: m/e=246.1/248.1 (M+H⁺), using chemistry similar to that described in Example 1, step 1 starting from 4-bromo-2-chloro-6-fluoroaniline and phenylacetylene.

Step 2: (9aRS)-7-[2-Chloro-6-fluoro-4-(2-phenylethynyl)phenyl]-9a-methyl-2,3,4,9-tetrahydropyrazino[1,2-c]pyrimidine-1,6,8-trione The title compound was obtained as a white solid, MS: m/e=424.3/426.2 (M+H⁺), using chemistry similar to that described in Example 1, step 2 starting from 2-chloro-6-fluoro-4-(2-phenylethynyl)aniline (Example 86, step 1) and methyl 2-[(2RS)-2-methyl-3-oxo-piperazin-2-yl]acetate.

The invention claimed is:
1. A compound of formula I

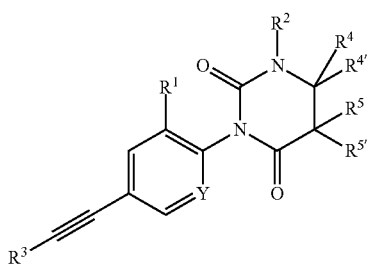

wherein
Y is N or C—R¹';
R¹' is hydrogen or F;
R¹ is hydrogen, halogen or lower alkyl substituted by halogen;
R² is hydrogen or lower alkyl;
or R² forms together with R⁴ a 6 membered heterocyclic ring containing —CH₂—CH₂—O—CH₂— or —CH₂—CH₂—NR—C(O)—;
R is hydrogen, lower alkyl, phenyl or benzyl;

R³ is phenyl or pyridinyl, wherein the N atom in the pyridinyl group may be in different positions;
R⁴'is hydrogen, lower alkyl or lower alkoxyalkyl;
R⁴ is hydrogen, lower alkyl, phenyl optionally substituted by halogen or lower alkoxy, or is cycloalkyl, or is pyridinyl optionally substituted by halogen, lower alkyl, lower alkoxy or =O, or is pyrimidinyl optionally substituted by lower alkyl, lower alkoxy or =O, or is 1-lower alkyl-pyridinyl, or is pyrazinyl, or is pyridazinyl optionally substituted by lower alkyl, lower alkoxy or =O, or is 1-methylpyrrolo[2,3-b]pyridine-5-yl, or is 6-imidazo[1,2-b]pyridazin-6-yl;
or R⁴ forms together with R⁴'a 4, 5 or 6 membered heterocyclic ring containing —(CH₂)₅—, —CH₂—CH₂—O—CH₂—CH₂—, —CH₂—CH₂—CH₂—, —CH₂—CH₂—CH₂—CH₂—, —CH₂—O—CH₂—CH₂— or CH₂—CH₂—CH₂—O—CH₂; and
R⁵ and R⁵'are hydrogen or lower alkyl;
or R⁴ forms together with R⁵ a saturated 5-membered ring containing —CH₂—CH₂—CH₂—;
or a pharmaceutically acceptable salt or acid addition salt, a racemic mixture, or its corresponding enantiomer and/or optical isomer and/or stereoisomer thereof.

2. A compound of formula IA according to claim 1,

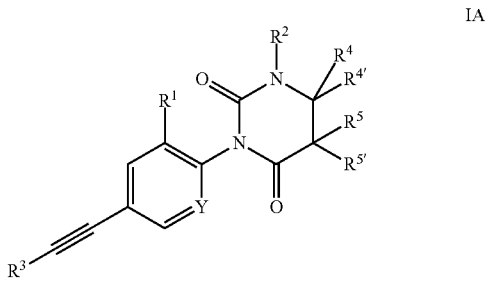

IA wherein
Y is N or C—R¹';
R¹'is hydrogen or F;
R¹ is hydrogen, halogen or lower alkyl substituted by halogen;
R² is hydrogen or lower alkyl;
R³ is phenyl or pyridinyl, wherein the N atom in the pyridinyl group may be in different positions;
R⁴'is hydrogen, lower alkyl or lower alkoxyalkyl;
R⁴ is hydrogen, lower alkyl, phenyl optionally substituted by halogen or lower alkoxy, or is cycloalkyl, or is pyridinyl optionally substituted by halogen, lower alkyl, lower alkoxy or =O, or is pyrimidinyl optionally substituted by lower alkyl, lower alkoxy or =O, or is 1-lower alkyl-pyridinyl, or is pyrazinyl, or is pyridazinyl optionally substituted by lower alkyl, lower alkoxy or =O, or is 1-methylpyrrolo[2,3-b]pyridine-5-yl, or is 6-imidazo[1,2-b]pyridazin-6-yl; and
R⁵ and R⁵'are hydrogen or lower alkyl;
or a pharmaceutically acceptable salt or acid addition salt, a racemic mixture, or its corresponding enantiomer and/or optical isomer and/or stereoisomer thereof.

3. A compound of formula IA according to claim 2, wherein the compound is selected from the group consisting of
3-[2,6-difluoro-4-(2-phenylethynyl)phenyl]-1,6,6-trimethyl-hexahydropyrimidine-2,4-dione
3-[2-chloro-4-(2-phenylethynyl)phenyl]-1,6,6-trimethyl-hexahydropyrimidine-2,4-dione
(5RS)-3-[2,6-difluoro-4-(2-phenylethynyl)phenyl]-1,5,6,6-tetramethyl-hexahydropyrimidine-2,4-dione
3-[2-chloro-6-fluoro-4-[2-(3-pyridyl)ethynyl]phenyl]-1,6,6-trimethyl-hexahydropyrimidine-2,4-dione
3-[2-chloro-6-fluoro-4-[2-(3-pyridyl)ethynyl]phenyl]-1-ethyl-6,6-dimethyl-hexahydropyrimidine-2,4-dione
(6RS)-3-[2,6-difluoro-4-(2-phenylethynyl)phenyl]-1,6-dimethyl-6-phenyl-hexahydropyrimidine-2,4-dione
(6RS)-3-[2,6-difluoro-4-(2-phenylethynyl)phenyl]-1,6-dimethyl-6-phenyl-hexahydropyrimidine-2,4-dione
(6RS)-3-[2,6-difluoro-4-[2-(3-pyridyl)ethynyl]phenyl]-1-ethyl-6-methyl-6-phenyl-hexahydropyrimidine-2,4-dione
(6RS)-3-[2,6-difluoro-4-(2-phenylethynyl)phenyl]-6-ethyl-1,6-dimethyl-hexahydropyrimidine-2,4-dione
(6S)-3-[2,6-difluoro-4-(2-phenylethynyl)phenyl]-1,6-dimethyl-6-phenyl-hexahydropyrimidine-2,4-dione
(6R)-3-[2,6-difluoro-4-(2-phenylethynyl)phenyl]-1,6-dimethyl-6-phenyl-hexahydropyrimidine-2,4-dione
3-[2,6-difluoro-4-(2-phenylethynyl)phenyl]-6,6-diethyl-hexahydropyrimidine-2,4-dione
3-[2,6-difluoro-4-(2-phenylethynyl)phenyl]-6,6-diethyl-1-methyl-hexahydropyrimidine-2,4-dione
(6RS)-1,6-dimethyl-6-phenyl-3-[5-(2-phenylethynyl)-2-pyridyl]hexahydropyrimidine-2,4-dione
(6RS)-1,6-dimethyl-6-phenyl-3-[4-(2-phenylethynyl)phenyl]hexahydropyrimidine-2,4-dione
(6RS)-3-[2,6-difluoro-4-(2-phenylethynyl)phenyl]-6-isopropyl-1,6-dimethyl-hexahydropyrimidine-2,4-dione
(6RS)-3-[2,6-difluoro-4-(2-phenylethynyl)phenyl]-1,6-dimethyl-6-(2-pyridyl)hexahydropyrimidine-2,4-dione
(6RS)-3-[2,6-difluoro-4-(2-phenylethynyl)phenyl]-1,6-dimethyl-6-(4-pyridyl)hexahydropyrimidine-2,4-dione
(6RS)-3-[2,6-difluoro-4-(2-phenylethynyl)phenyl]-1,6-dimethyl-6-(3-pyridyl)hexahydropyrimidine-2,4-dione
(6RS)-3-[2,6-difluoro-4-(2-phenylethynyl)phenyl]-6-(methoxymethyl)-1,6-dimethyl-hexahydropyrimidine-2,4-dione
(6RS)-6-cyclohexyl-3-[2,6-difluoro-4-[2-(3-pyridyl)ethynyl]phenyl]-1,6-dimethyl-hexahydropyrimidine-2,4-dione
(6RS)-3-[3-chloro-5-(2-phenylethynyl)-2-pyridyl]-1,6-dimethyl-6-phenyl-hexahydropyrimidine-2,4-dione
(6RS)-3-[2-chloro-6-fluoro-4-[2-(3-pyridyl)ethynyl]phenyl]-1,6-dimethyl-6-(3-pyridyl)hexahydropyrimidine-2,4-dione
(6RS)-3-[2-chloro-6-fluoro-4-[2-(3-pyridyl)ethynyl]phenyl]-1,6-dimethyl-6-phenyl-hexahydropyrimidine-2,4-dione
(6RS)-6-(3-chlorophenyl)-3-[2,6-difluoro-4-[2-(3-pyridyl)ethynyl]phenyl]-1,6-dimethyl-hexahydropyrimidine-2,4-dione
(6RS)-6-(2-chlorophenyl)-3-[2,6-difluoro-4-[2-(3-pyridyl)ethynyl]phenyl]-1,6-dimethyl-hexahydropyrimidine-2,4-dione
(6RS)-6-(4-chlorophenyl)-3-[2,6-difluoro-4-[2-(3-pyridyl)ethynyl]phenyl]-1,6-dimethyl-hexahydropyrimidine-2,4-dione
(6RS)-3-[2,6-difluoro-4-[2-(3-pyridyl)ethynyl]phenyl]-6-(3-methoxyphenyl)-1,6-dimethyl-hexahydropyrimidine-2,4-dione
(6RS)-6-tert-butyl-3-[2,6-difluoro-4-(2-phenylethynyl)phenyl]-6-methyl-hexahydropyrimidine-2,4-dione
(6RS)-6-tert-butyl-3-[2,6-difluoro-4-(2-phenylethynyl)phenyl]-1,6-dimethyl-hexahydropyrimidine-2,4-dione
(6RS)-3-[3-fluoro-5-(2-phenylethynyl)-2-pyridyl]-1,6-dimethyl-6-phenyl-hexahydropyrimidine-2,4-dione (6RS)-1,6-dimethyl-6-phenyl-3-[5-(2-phenylethynyl)-3-(trifluoromethyl)-2-pyridyl]hexahydropyrimidine-2,4-dione (6RS)-3-[2-Chloro-4-(2-phenylethynyl)phenyl]-1,6-dimethyl-6-(3-pyridyl)hexahydropyrimidine-2,4-dione (6RS)-3-[2,6-Difluoro-4-[2-(3-pyridyl)ethynyl]phenyl]-6-ethyl-1-methyl-6-phenyl-hexahydropyrimidine-2,4-dione (6S)-3-[2,6-Difluoro-4-(2-phenylethynyl)phenyl]-1,6-dimethyl-6-(3-pyridyl)hexahydropyrimidine-2,4-dione (6S)-3-[3-Fluoro-5-(2-phenylethynyl)-2-pyridyl]-1,6-dimethyl-6-(3-pyridyl)hexahydropyrimidine-2,4-dione (6RS)-6-(6-Chloro-3-pyridyl)-3-[2,6-difluoro-4-(2-phenylethynyl)phenyl]-1,6-dimethyl-hexahydropyrimidine-2,4-dione (6S)-3-[2,6-Difluoro-4-(2-phenylethynyl)phenyl]-1-ethyl-6-methyl-6-(3-pyridyl)hexahydropyrimidine-2,4-dione (6S)-3-[2,6-Difluoro-4-[2-(3-pyridyl)ethynyl]phenyl]-1,6-dimethyl-6-(3-pyridyl)hexahydropyrimidine-2,4-dione (6S)-3-[2,6-Difluoro-4-(2-phenylethynyl)phenyl]-1,6-dimethyl-6-(6-methyl-3-pyridyl)hexahydropyrimidine-2,4-dione (6S)-3-[2,6-Difluoro-4-(2-phenylethynyl)phenyl]-1,6-dimethyl-6-pyrimidin-4-yl-hexahydropyrimidine-2,4-dione (6S)-3-[2,6-Difluoro-4-(2-phenylethynyl)phenyl]-1,6-dimethyl-6-pyrimidin-5-yl-hexahydropyrimidine-2,4-dione (6S)-3-[2,6-Difluoro-4-(2-phenylethynyl)phenyl]-1,6-dimethyl-6-pyrazin-2-yl-hexahydropyrimidine-2,4-dione (6S)-3-[2,6-Difluoro-4-(2-phenylethynyl)phenyl]-1,6-dimethyl-6-pyridazin-3-yl-hexahydropyrimidine-2,4-dione (6S)-3-[2,6-Difluoro-4-(2-phenylethynyl)phenyl]-6-(5-fluoro-3-pyridyl)-1,6-dimethyl-hexahydropyrimidine-2,4-dione (6S)-6-(2-Chloro-4-pyridyl)-3-[2,6-difluoro-4-(2-phenylethynyl)phenyl]-1,6-dimethyl-hexahydropyrimidine-2,4-dione (6S)-3-[2,6-Difluoro-4-(2-phenylethynyl)phenyl]-1,6-dimethyl-6-pyridazin-4-yl-hexahydropyrimidine-2,4-dione (6S)-3-[2,6-Difluoro-4-(2-phenylethynyl)phenyl]-1,6-dimethyl-6-(2-methyl-4-pyridyl)hexahydropyrimidine-2,4-dione (6S)-3-[2,6-Difluoro-4-(2-phenylethynyl)phenyl]-6-(6-methoxy-3-pyridyl)-1,6-dimethyl-hexahydropyrimidine-2,4-dione (6S)-6-(2-Chloro-4-pyridyl)-3-[2,6-difluoro-4-[2-(3-pyridyl)ethynyl]phenyl]-1,6-dimethyl-hexahydropyrimidine-2,4-dione (6S)-3-[2,6-Difluoro-4-(2-phenylethynyl)phenyl]-1,6-dimethyl-6-(6-oxo-1H-pyridin-3-yl)hexahydropyrimidine-2,4-dione (6S)-3-[2,6-Difluoro-4-(2-phenylethynyl)phenyl]-1,6-dimethyl-6-(1-methyl-6-oxo-3-pyridyl)hexahydropyrimidine-2,4-dione (6S)-3-[2,6-Difluoro-4-(2-phenylethynyl)phenyl]-6-(1-ethyl-6-oxo-3-pyridyl)-1,6-dimethyl-hexahydropyrimidine-2,4-dione (6S)-3-[2,6-Difluoro-4-(2-phenylethynyl)phenyl]-6-(1-isopropyl-6-oxo-3-pyridyl)-1,6-dimethyl-hexahydropyrimidine-2,4-dione (6S)-3-[2,6-Difluoro-4-(2-phenylethynyl)phenyl]-6-(6isopropoxy-3-pyridyl)-1,6-dimethyl-hexahydropyrimidine-2,4-dione (6S)-3-[2,6-Difluoro-4-(2-phenylethynyl)phenyl]-1-isopropyl-6-methyl-6-(3-pyridyl)hexahydropyrimidine-2,4-dione (6S)-3-[2-Chloro-6-fluoro-4-(2-phenylethynyl)phenyl]-1,6-dimethyl-6-(3-pyridyl)hexahydropyrimidine-2,4-dione (6RS)-3-[2,6-Difluoro-4-[2-(3-pyridyl)ethynyl]phenyl]-1-methyl-6-phenyl-6-(trifluoromethyl)hexahydropyrimidine-2,4-dione (6S)-3-[2,6-Difluoro-4-(2-phenylethynyl)phenyl]-6-(2-methoxy-4-pyridyl)-1,6-dimethyl-hexahydropyrimidine-2,4-dione (6S)-3-[2,6-Difluoro-4-(2-phenylethynyl)phenyl]-1,6-dimethyl-6-(2-oxo-1H-pyridin-4-yl)hexahydropyrimidine-2,4-dione (6S)-3-[2,6-Difluoro-4-(2-phenylethynyl)phenyl]-1,6-dimethyl-6-(1-methyl-2-oxo-4-pyridyl)hexahydropyrimidine-2,4-dione (6S)-3-[2,6-Difluoro-4-(2-phenylethynyl)phenyl]-1,6-dimethyl-6-(2-methylpyrimidin-4-yl)hexahydropyrimidine-2,4-dione (6S)-3-[2,6-Difluoro-4-(2-phenylethynyl)phenyl]-1-ethyl-6-methyl-6-(2-methyl-4-pyridyl)hexahydropyrimidine-2,4-dione (6S)-3-[2,6-Difluoro-4-(2-phenylethynyl)phenyl]-1,6-dimethyl-6-(4-pyridyl)hexahydropyrimidine-2,4-dione (6S)-3-[2,6-Difluoro-4-(2-phenylethynyl)phenyl]-6-(2-methoxypyrimidin-5-yl)-1,6-dimethyl-hexahydropyrimidine-2,4-dione(6S)-3-[2,6-Difluoro-4-(2-phenylethynyl)phenyl]-1,6-dimethyl-6-(2-oxo-1H-pyrimidin-5-yl)hexahydropyrimidine-2,4-dione (6S)-3-[2,6-Difluoro-4-(2-phenylethynyl)phenyl]-6-(6-methoxypyridazin-3-yl)-1,6-dimethyl-hexahydropyrimidine-2,4-dione (6S)-3-[2,6-Difluoro-4-(2-phenylethynyl)phenyl]-1,6-dimethyl-6-(6-oxo-1H-pyridazin-3-yl)hexahydropyrimidine-2,4-dione (6S)-3-[2,6-Difluoro-4-(2-phenylethynyl)phenyl]-1,6-dimethyl-6-(1-methyl-6-oxo-pyridazin-3-yl)hexahydropyrimidine-2,4-dione (6S)-3-[2,6-Difluoro-4-(2-phenylethynyl)phenyl]-1,6-dimethyl-6-(1-methylpyrrolo[2,3-b]pyridin-5-yl)hexahydropyrimidine-2,4-dione and (6S)-3-[2,6-Difluoro-4-(2-phenylethynyl)phenyl]-6-imidazo[1,2-b]pyridazin-6-yl-1,6-dimethyl-hexahydropyrimidine-2,4-dione.

4. A compound of formula IB-1 or IB-2 according to claim 1

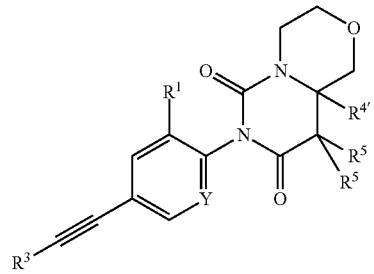

-continued

IB-2

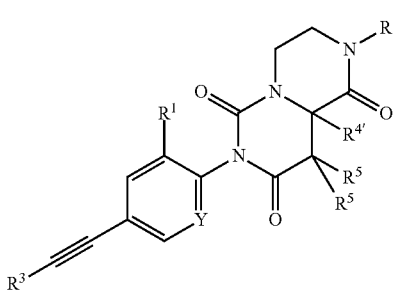

wherein
Y is N or C—R[1'];
R[1']is hydrogen or F;
R[1] is hydrogen, halogen or lower alkyl substituted by halogen;
R is hydrogen, lower alkyl, phenyl or benzyl;
R[3] is phenyl or pyridinyl, wherein the N atom in the pyridinyl group may be in different positions;
R[4']is hydrogen, lower alkyl or lower alkoxyalkyl; and
R[5] and R[5']are hydrogen or lower alkyl;
or a pharmaceutically acceptable salt or acid addition salt, a racemic mixture, or its corresponding enantiomer and/or optical isomer and/or stereoisomer thereof.

5. A compound of formula IB-1 or IB-2 according to claim 4, wherein the compound is selected from the group consisting of
(9aRS)-7-[2,6-difluoro-4-(2-phenylethynyl)phenyl]-3,4,9,9a-tetrahydro-1H-pyrimido[6,1-c][1,4]oxazine-6,8-dione
(9aRS)-7-[2,6-difluoro-4-(2-phenylethynyl)phenyl]-9a-methyl-2,3,4,9-tetrahydropyrazino[1,2-c]pyrimidine-1,6,8-trione
(9aRS)-7-[2,6-difluoro-4-(2-phenylethynyl)phenyl]-2,9a-dimethyl-4,9-dihydro-3H-pyrazino[1,2-c]pyrimidine-1,6,8-trione
(9aRS)-7-[2,6-difluoro-4-(2-phenylethynyl)phenyl]-2-isopropyl-9a-methyl-4,9-dihydro-3H-pyrazino[1,2-c]pyrimidine-1,6,8-trione
(9aRS)-2-benzyl-7-[2,6-difluoro-4-(2-phenylethynyl)phenyl]-9a-methyl-4,9-dihydro-3H-pyrazino[1,2-c]pyrimidine-1,6,8-trione
(9aRS)-7-[2,6-difluoro-4-(2-phenylethynyl)phenyl]-9a-methyl-2-phenyl-4,9-dihydro-3H-pyrazino[1,2-c]pyrimidine-1,6,8-trione and
(9aRS)-7-[2-Chloro-6-fluoro-4-(2-phenylethynyl)phenyl]-9a-methyl-2,3,4,9-tetrahydropyrazino[1,2-c]pyrimidine-1,6,8-trione.

6. A compound of formula IC-1, IC-2, IC-3, IC-4, IC-5 or IC-6 according to claim 1

IC-1

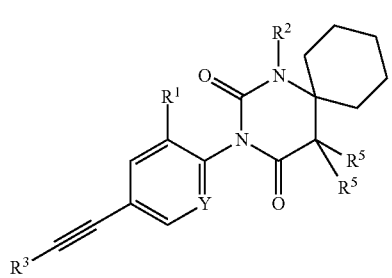

-continued

IC-2

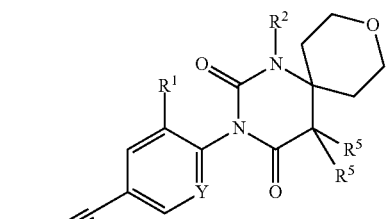

IC-3

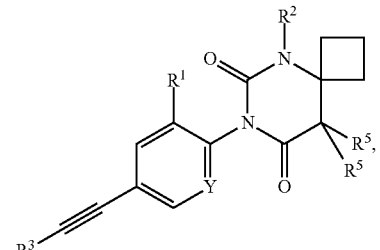

IC-4

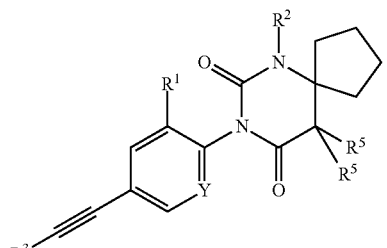

IC-5

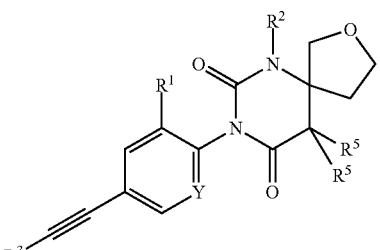

IC-6

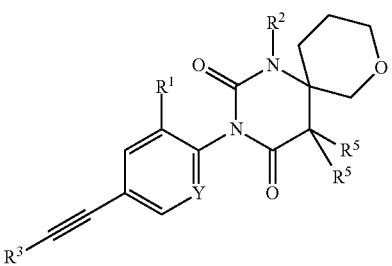

wherein
Y is N or C—R[1'];
R[1']is hydrogen or F;
R[1] is hydrogen, halogen or lower alkyl substituted by halogen;
R[2] is hydrogen or lower alkyl;
R[3] is phenyl or pyridinyl, wherein the N atom in the pyridinyl group may be in different positions; and
R[5] and R[5']are hydrogen or lower alkyl;
or a pharmaceutically acceptable salt or acid addition salt, a racemic mixture, or its corresponding enantiomer and/or optical isomer and/or stereoisomer thereof.

7. A compound of formula IC-1, IC-2, IC-3, IC-4, IC-5 or IC-6 according to claim 6,
wherein the compound is selected from the group consisting of
3-[2-chloro-4-(2-phenylethynyl)phenyl]-1-methyl-1,3-diazaspiro[5.5]undecane-2,4-dione
3-[2-chloro-4-(2-phenylethynyl)phenyl]-1-methyl-9-oxa-1,3-diazaspiro[5.5]undecane-2,4-dione
7-[2-chloro-4-(2-phenylethynyl)phenyl]-5-methyl-5,7-diazaspiro[3.5]nonane-6,8-dione
8-[2,6-difluoro-4-(2-phenylethynyl)phenyl]-6-methyl-6,8-diazaspiro[4.5]decane-7,9-dione
(5RS)-8-[2,6-difluoro-4-(2-phenylethynyl)phenyl]-6-methyl-2-oxa-6,8-diazaspiro[4.5]decane-7,9-dione and
(6RS)-3-[2,6-difluoro-4-(2-phenylethynyl)phenyl]-1-methyl-8-oxa-1,3-diazaspiro[5.5]undecane-2,4-dione.

8. A compound of formula ID according to claim 1

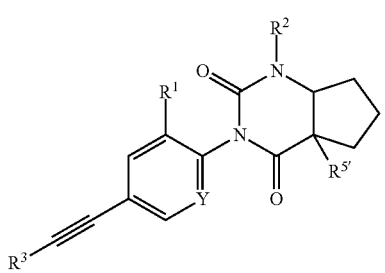

ID wherein
Y is N or C—R$^{1'}$;
R$^{1'}$ is hydrogen or F;
R$^1$ is hydrogen, halogen or lower alkyl substituted by halogen;
R$^2$ is hydrogen or lower alkyl;
R$^3$ is phenyl or pyridinyl, wherein the N atom in the pyridinyl group may be in different positions; and
R$^{5'}$ is hydrogen or lower alkyl;
or a pharmaceutically acceptable salt or acid addition salt, a racemic mixture, or its corresponding enantiomer and/or optical isomer and/or stereoisomer thereof.

9. A compound of formula ID according to claim 8, wherein the compound is
(4aRS,7aSR)-3-[2,6-difluoro-4-(2-phenylethynyl)phenyl]-1-methyl-5,6,7,7a-tetrahydro-4aH-cyclopenta[d]pyrimidine-2,4-dione or
(4aRS,7aRS)-3-[2,6-difluoro-4-(2-phenylethynyl)phenyl]-1,7a-dimethyl-4a,5,6,7-tetrahydrocyclopenta[d]pyrimidine-2,4-dione.

10. A process for the manufacture of a compound of formula I as defined in claim 1, which process comprises
a) alkylating a compound of formula

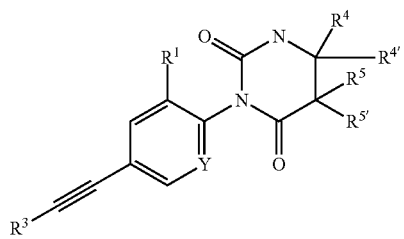

6 with R$^2$-I in the presence of NaH or Cs$_2$CO$_3$ in DMF to form a compound of formula

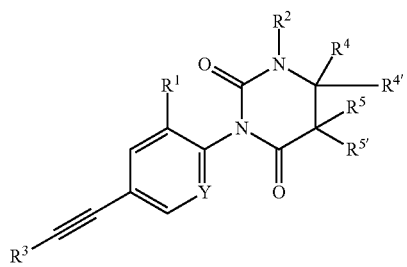

I wherein the substituents are described in claim 1, or
if desired, converting the compounds obtained into a pharmaceutically acceptable acid addition salt.

11. A pharmaceutical composition comprising a compound of formula I as in claim 1 and a pharmaceutically acceptable excipient.

12. A method for the treatment of Parkinson's disease, anxiety, emesis, obsessive compulsive disorder, autism, neuroprotection, depression and diabetes type 2, which method comprises administering an effective amount of a compound of formula I as in claim 1 to a mammal in need.

* * * * *